US009598432B2

(12) United States Patent
Argade et al.

(10) Patent No.: US 9,598,432 B2
(45) Date of Patent: Mar. 21, 2017

(54) 2,4-PYRIMIDINEDIAMINE COMPOUNDS AND USES AS ANTI-PROLIFERATIVE AGENTS

(71) Applicants: Ankush Argade, Foster City, CA (US); Rajinder Singh, Belmont, CA (US); Hui Li, Santa Clara, CA (US); David Carroll, San Francisco, CA (US); Susan Catalano, Hayward, CA (US)

(72) Inventors: Ankush Argade, Foster City, CA (US); Rajinder Singh, Belmont, CA (US); Hui Li, Santa Clara, CA (US); David Carroll, San Francisco, CA (US); Susan Catalano, Hayward, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/324,636

(22) Filed: Jul. 7, 2014

(65) Prior Publication Data
US 2015/0011002 A1    Jan. 8, 2015

Related U.S. Application Data

(63) Continuation of application No. 12/981,094, filed on Dec. 29, 2010, now Pat. No. 8,809,341, which is a continuation of application No. 11/567,820, filed on Dec. 7, 2006, now Pat. No. 7,884,111, which is a continuation of application No. 10/913,270, filed on Aug. 6, 2004, now abandoned.

(60) Provisional application No. 60/494,008, filed on Aug. 7, 2003, provisional application No. 60/572,534, filed on May 18, 2004.

(51) Int. Cl.
| C07D 239/48 | (2006.01) |
| C07D 403/00 | (2006.01) |
| C07D 413/00 | (2006.01) |
| A61K 31/495 | (2006.01) |
| C07D 498/04 | (2006.01) |
| A61K 31/4353 | (2006.01) |
| A61K 31/505 | (2006.01) |
| A61K 31/506 | (2006.01) |
| C07D 401/12 | (2006.01) |
| C07D 401/14 | (2006.01) |
| C07D 403/12 | (2006.01) |
| C07D 405/12 | (2006.01) |
| C07D 413/12 | (2006.01) |
| C07D 413/14 | (2006.01) |
| C07D 417/12 | (2006.01) |
| C07D 417/14 | (2006.01) |

(52) U.S. Cl.
CPC ........ *C07D 498/04* (2013.01); *A61K 31/4353* (2013.01); *A61K 31/505* (2013.01); *A61K 31/506* (2013.01); *C07D 239/48* (2013.01); *C07D 401/12* (2013.01); *C07D 401/14* (2013.01); *C07D 403/12* (2013.01); *C07D 405/12* (2013.01); *C07D 413/12* (2013.01); *C07D 413/14* (2013.01); *C07D 417/12* (2013.01); *C07D 417/14* (2013.01)

(58) Field of Classification Search
None
See application file for complete search history.

(56) References Cited

U.S. PATENT DOCUMENTS

| 5,958,935 | A | 9/1999 | Davis et al. | |
| 6,593,326 | B1 | 7/2003 | Bradbury et al. | |
| 7,514,446 | B2 | 4/2009 | Davis-Ward et al. | |
| 7,754,714 | B2* | 7/2010 | Li | C07D 205/12 514/235.8 |
| 7,884,111 | B2 | 2/2011 | Argade et al. | |
| 8,809,341 | B2* | 8/2014 | Argade | A61K 31/4353 514/228.8 |
| 2005/0113398 | A1 | 5/2005 | Argade et al. | |
| 2006/0276459 | A1 | 12/2006 | Masuda et al. | |
| 2009/0048214 | A1 | 2/2009 | Hitoshi et al. | |
| 2010/0204208 | A1* | 8/2010 | Singh | C07D 401/12 514/217.04 |
| 2011/0130415 | A1* | 6/2011 | Singh | C07D 405/14 514/275 |

FOREIGN PATENT DOCUMENTS

| WO | 00/39101 | 7/2000 | |
| WO | 02/059110 | 8/2002 | |
| WO | 03/026664 | 4/2003 | |
| WO | WO 03026665 A1 * | 4/2003 | ........... C07D 231/12 |
| WO | 03/030909 | 5/2003 | |
| WO | 03/040141 | 5/2003 | |

OTHER PUBLICATIONS

Talmadge, et al., "Murine Models to Evaluate Novel and Conventional Therapeutic Strategies for Cancer," The American Journal of Pathology, 170(3):793-804 (Mar. 2007).
Suggit et al., "50 Years of Preclinical Anticancer Drug Screening: Empirical to Target-Driven Approaches," Clinical Cancer research, 11:971-981 (Feb. 1, 2005).
Vippagunta et al., "Crystalline solids," Advanced Drug Delivery Reviews, 48:3-26 (2001).
Cecil's Textbook of Medicine (Twenty-First Edition, vol. 1), W.B. Saunders Company, 1060-1074 (2000).
International Search Report for PCT/US2004/025409 dated Feb. 24, 2005.
Kamb, Nature Reviews Drug Discovery 4, 161-165 (Feb. 2005).

(Continued)

*Primary Examiner* — Abigail Fisher
(74) *Attorney, Agent, or Firm* — Travis Young; McDonnell Boehnen Hulbert & Berghoff LLP

(57) ABSTRACT

The present invention provides 2,4-pyrimidinediamine compounds having antiproliferative activity, compositions comprising the compounds and methods of using the compounds to inhibit cellular proliferation and to treat proliferative diseases such as tumorigenic cancers.

17 Claims, No Drawings

(56) References Cited

OTHER PUBLICATIONS

Kola, Nature Reviews Drug Discovery 3, 711-715 (2004).
Expert Scientific Group on Phase One Clinical Trials Final Report, Nov. 30, 2006, pp. C1, C35-C38.
Leaf, Clifton, Health Administrator, vol. XVII, No. 1: 172-183, 2005.
Cancer Drug Design and Discovery Neidle, Stephen, ed., (Elsevier/Academic Press, 2008) pp. 427-431.
Roberts, Jr. et al., JAMA 292(17):2130-2140 (2004).
Gura, Science Nov. 7, 1997: vol. 278, No. 5340, pp. 1041-1042.
Grant et al., Advanced Drug Delivery Reviews, 2001, 3-26.

\* cited by examiner

2,4-PYRIMIDINEDIAMINE COMPOUNDS AND USES AS ANTI-PROLIFERATIVE AGENTS

1. CROSS-REFERENCE TO RELATED APPLICATIONS

This application is a continuation of U.S. application Ser. No. 12/981,094, filed Dec. 29, 2010, which is a continuation of U.S. application Ser. No. 11/567,820, filed Dec. 7, 2006, which is a continuation of U.S. patent application Ser. No. 10/913,270, filed Aug. 6, 2004, now abandoned, Which claims benefit to U.S. Provisional Application No. 60/494,008, filed Aug. 7, 2003 and U.S. Provisional Application No. 60/572,534, filed May 18, 2004. Each of the foregoing applications is incorporated by reference in its entirety.

2. FIELD

The present invention relates to 2,4 pyrimidinediamine compounds that exhibit antiproliferative activity, prodrugs of the compounds, intermediates and methods of synthesis for making the compounds and/or prodrugs, pharmaceutical compositions comprising the compounds and the use of the compounds in a variety of contexts, including for the treatment of proliferative disorders, such as, for example, tumors and cancers.

3. BACKGROUND

Cancer is a group of varied diseases characterized by uncontrolled growth and spread of abnormal cells. Generally, all types of cancers involve some abnormality in the control of cell growth and division. The pathways regulating cell division and/or cellular communication become altered in cancer cells such that the effects of these regulatory mechanisms in controlling and limiting cell growth fails or is bypassed. Through successive rounds of mutation and natural selection, a group of abnormal cells, generally originating from a single mutant cell, accumulates additional mutations that provide selective growth advantage over other cells, and thus evolves into a cell type that predominates in the cell mass. This process of mutation and natural selection is enhanced by genetic instability displayed by many types of cancer cells, an instability which is gained either from somatic mutations or by inheritance from the germ line. The enhanced mutability of cancerous cells increases the probability of their progression towards formation of malignant cells. As the cancer cells further evolve, some become locally invasive and then metastasize to colonize tissues other than the cancer cell's tissue of origin. This property along with the heterogeneity of the tumor cell population makes cancer a particularly difficult disease to treat and eradicate.

Traditional cancer treatments take advantage of the higher proliferative capacity of cancer cells and their increased sensitivity to DNA damage. Ionizing radiation, including γ-rays and x-rays, and cytotoxic agents, such as bleomycin, cis-platin, vinblastine, cyclophosphamide, 5'-fluorouracil, and methotrexate rely upon a generalized damage to DNA and destabilization of chromosomal structure which eventually lead to destruction of cancer cells. These treatments are particularly effective for those types of cancers that have defects in cell cycle checkpoint, which limits the ability of these cells to repair damaged DNA before undergoing cell division. The non-selective nature of these treatments, however, often results in severe and debilitating side effects. The systemic use of these drugs may result in damage to normally healthy organs and tissues, and compromise the long term health of the patient.

Although more selective chemotherapeutic treatments have been developed based on knowledge of how cancer cells develop, for example, the anti-estrogen compound tamoxifen, the effectiveness of all chemotherapeutic treatments are subject to development of resistance to the drugs. In particular, the increased expression of cell membrane bound transporters, such as MdrI, produces a multidrug resistance phenotype characterized by increased efflux of drugs from the cell. These types of adaptation by cancer cells severely limit the effectiveness of certain classes of chemotherapeutic agents. Consequently, identification of other chemotherapeutic agents is critical for establishing therapies effective for attacking the heterogeneous nature of proliferative disease and for overcoming any resistance that may develop over the course of therapy with other compounds. Moreover, use of combinations of chemotherapeutic agents with differing properties and cellular targets increases the effectiveness of chemotherapy and limits the generation of drug resistance.

4. SUMMARY

In one aspect, the present invention provides 2,4-pyrimidinediamine compounds that exhibit antiproliferative activity against a variety of different cell types, including a variety of different types of tumor cells. The compounds are generally 2,4-pyrimidinediamine compounds according to structural formula (I):

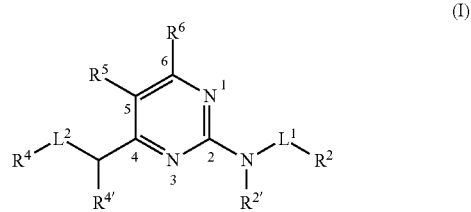

including salts, hydrates, solvates and N-oxides thereof, wherein:
 $L^1$ and $L^2$ are each, independently of one another, selected from a lower alkyldiyl linker, a lower alkylene linker and a covalent bond;
 $R^2$ is selected from the group consisting of lower alkyl optionally substituted with an $R^b$ group.

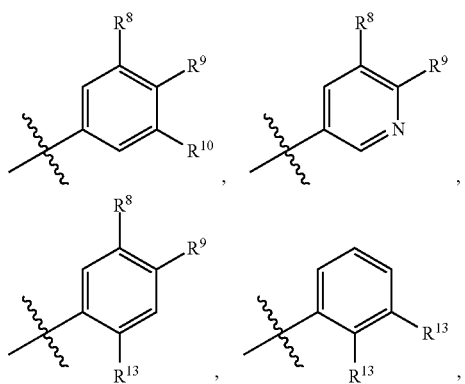

-continued

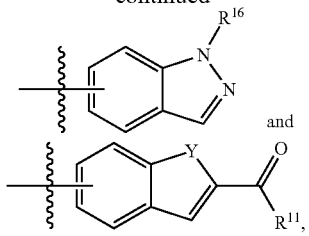
and where Y is NH, O or CH$_2$;

R$^{2'}$ is hydrogen, methyl or lower alkyl;

R$^{4'}$ is hydrogen, methyl or lower alkyl;

R$^4$ is selected from the group consisting of lower alkyl optionally monosubstituted with an R$^a$ or R$^b$ group, lower cycloalkyl optionally monosubstituted with an R$^a$ or R$^b$ group, lower cycloheteroalkyl optionally substituted at one or more ring carbon and/or heteroatoms with an R$^a$ or R$^b$ group, —(CR$^a$R$^a$)$_n$—R$^b$,

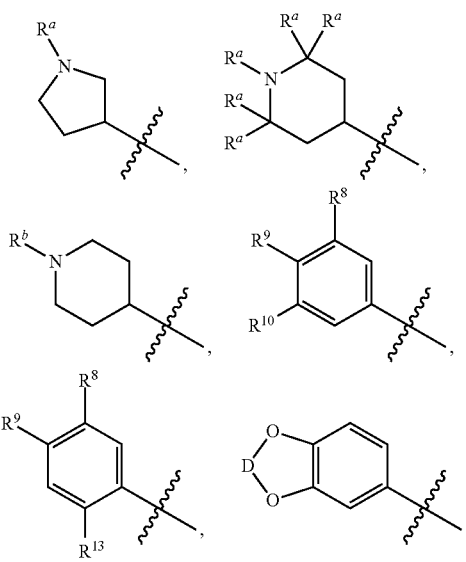

where D is —(CR$^7$R$^7$)$_m$—,

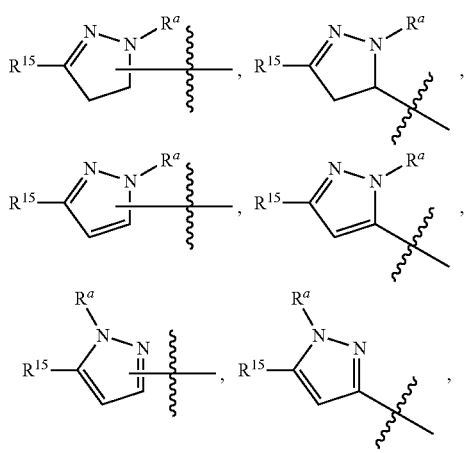

-continued

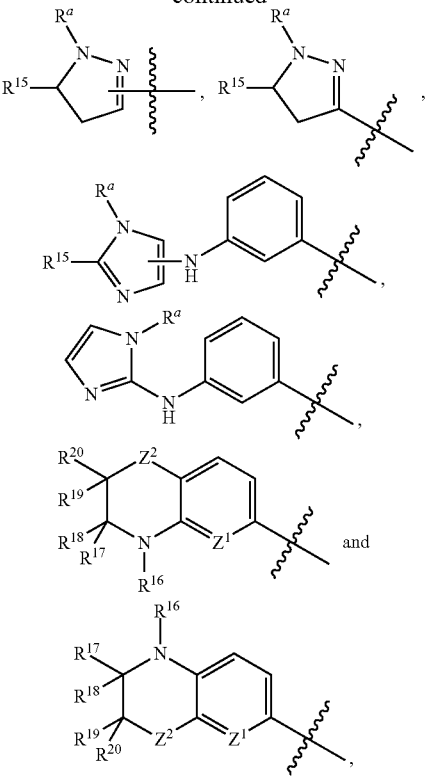

where Z$^1$ is N or CH and Z$^2$ is O, S, NH, S(O) or S(O)$_2$;

R$^5$ is selected from the group consisting of halo, fluoro and —CF$_3$;

R$^6$ is hydrogen;

each R$^7$ is independently selected from the group consisting of hydrogen, methyl, lower alkyl and halo;

each R$^8$ is independently selected from the group consisting of hydrogen, lower alkyl, —(CH$_2$)$_n$—OH, —OR$^a$, —(CH$_2$)$_n$—NR$^c$R$^c$, —O(CH$_2$)$_n$—R$^a$, —O(CH$_2$)$_n$—R$^b$, —C(O)OR$^a$, —C(S)OR$^a$, halo, —CF$_3$ and —OCF$_3$;

each R$^9$ is independently selected from the group consisting of hydrogen, lower alkyl, —OR$^a$, —(CH$_2$)$_n$—NR$^c$R$^c$, —O(CH$_2$)$_n$—R$^a$, —O(CH$_2$)$_n$—R$^b$, —C(O)—NR$^c$R$^c$, —C(S)—NR$^c$R$^c$, —S(O)$_2$—NR$^c$R$^c$, —NHC(O)R$^a$, —NHC(S)R$^a$, —C(O)—NH—(CH$_2$)$_n$—NR$^c$R$^c$, —C(S)—NH—(CH$_2$)$_n$—NR$^c$R$^c$, halo, —CF$_3$, —OCF$_3$,

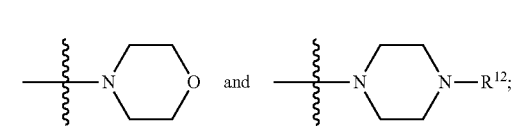

each R$^{10}$ is independently selected from the group consisting of hydrogen, lower alkyl, —(CH$_2$)$_n$—OH, —(CH$_2$)$_n$—NR$^c$R$^c$, —OR$^a$, —O(CH$_2$)$_n$—R$^a$, —O(CH$_2$)$_n$—R$^b$, halo, —CF$_3$, —OCF$_3$,

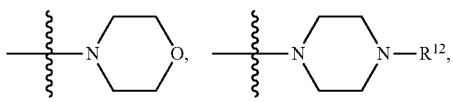

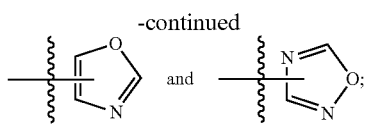

each $R^{11}$ is independently selected from the group consisting of —$OR^a$, —$NR^cR^c$ and —$NR^aR^d$;

each $R^{12}$ is independently selected from the group consisting of lower alkyl, arylalkyl, —$OR^a$, —$NR^cR^c$, —$C(O)R^a$, —$C(O)OR^a$ and —$C(O)NR^cR^c$;

each $R^{13}$ is independently selected from the group consisting of lower alkyl, hydroxy, lower alkoxy, methoxy, —$C(O)NR^cR^c$ and —$C(O)NH_2$;

each $R^{15}$ is independently selected from the group consisting of hydrogen, lower alkyl, lower cycloakyl and phenyl;

each $R^{16}$ is independently selected from the group consisting of hydrogen, methyl, lower alkyl, lower cycloalkyl, lower branched alkyl and lower cycloalkylmethyl;

each $R^{17}$ is independently selected from the group consisting of hydrogen, lower alkyl, methyl and $R^d$ or, alternatively, $R^{17}$ may be taken together with $R^{18}$ to form an oxo (=O) group;

each $R^{18}$ is independently selected from the group consisting of hydrogen, lower alkyl and methyl or, alternatively, $R^{18}$ may be taken together with $R^{17}$ to form an oxo (=O) group;

each $R^{19}$ is independently selected form the group consisting of hydrogen, lower alkyl, methyl and $R^d$;

each $R^{20}$ is independently selected from the group consisting of hydrogen, lower alkyl, methyl and $R^d$;

each m is independently an integer from 1 to 3;

each n is independently an integer from 1 to 3;

each $R^a$ is independently selected from the group consisting of hydrogen, lower alkyl, lower cycloalkyl, lower cycloalkylalkyl, phenyl and benzyl;

each $R^b$ is independently selected from the group consisting of —$OR^a$, —$CF_3$, —$OCF_3$, —$NR^cR^c$, —$C(O)R^a$, —$C(S)R^a$, —$C(O)OR^a$, —$C(S)OR^a$, —$C(O)NR^cR^c$, —$C(S)NR^cR^c$, —$S(O)_2NR^cR^c$, —$C(O)NR^aR^d$, —$C(S)NR^aR^d$ and —$S(O)_2NR^aR^d$;

each $R^c$ is independently selected from the group consisting of hydrogen, lower alkyl and lower cycloalkyl, or, alternatively, two $R^c$s may be taken together with the nitrogen atom to which they are bonded to form a 5-7 membered saturated ring which optionally includes 1-2 additional heteroatomic groups selected from O, $NR^a$, $NR^a$—$C(O)R^a$, $NR^a$—$C(O)OR^a$ and $NR^a$—$C(O)NR^a$; and each $R^d$ is independently selected from lower monohydroxyalkyl and lower di-hydroxyalkyl.

In another aspect, the present invention provides prodrugs of the 2,4-pyrimidinediamine compounds. Such prodrugs may be active in their prodrug form, or may be inactive until converted under physiological or other conditions of use to an active drug form. In the prodrugs, one or more functional groups of the 2,4-pyrimidinediamine compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs include special types of protecting groups, termed "progroups," masking one or more functional groups of the 2,4-pyrimidinediamine compounds that cleave under the conditions of use to yield an active 2,4-pyrimidinediamine drug compound. Functional groups within the 2,4-pyrimidinediamine compounds that may be masked with progroups for inclusion in a promoiety include, but are not limited to, amines (primary and secondary), hydroxyls, sulfanyls (thiols), carboxyls, carbonyls, phenols, catechols, diols, alkynes, phosphates, etc. Myriad progroups suitable for masking such functional groups to yield promoieties that are cleavable under the desired conditions of use are known in the art. All of these progroups, alone or in combinations, may be included in the prodrugs. Specific examples of promoieties that yield primary or secondary amine groups that can be included in the prodrugs include, but are not limited to, amides, carbamates, imines, ureas, phosphenyls, phosphoryls and sulfenyls. Specific examples of promoieties that yield sulfanyl groups that can be included in the prodrugs include, but are not limited to, thioethers, for example S-methyl derivatives (monothio, dithio, oxythio, aminothio acetals), silyl thioethers, thioesters, thiocarbonates, thiocarbamates, asymmetrical disulfides, etc. Specific examples of promoieties that cleave to yield hydroxyl groups that can be included in the prodrugs include, but are not limited to, sulfonates, esters and carbonates. Specific examples of promoieties that yield carboxyl groups that can be included in the prodrugs include, but are not limited to, esters (including silyl esters, oxamic acid esters and thioesters), amides and hydrazides.

In another aspect, the present invention provides compositions comprising one or more 2,4-pyrimidinediamine compounds and/or prodrugs and an appropriate carrier, excipient and/or diluent. The exact nature of the carrier, excipient and/or diluent will depend upon the desired use for the composition, and may range from being suitable or acceptable for veterinary uses to being suitable or acceptable for human use.

The 2,4-pyrimidinediamine compounds are potent inhibitors of proliferation abnormal cells, such as tumor cell proliferation, in in vitro assays. Thus, in still another aspect, the present invention provides methods of inhibiting proliferation of abnormal cells, in particular tumor cells. The method generally involves contacting an abnormal cell such as a tumor cells with an amount of a 2,4-pyrimidinediamine compound or prodrug, or an acceptable salt, hydrate, solvate, N-oxide and/or composition thereof, effective to inhibit its proliferation. The method may be practiced in in vitro contexts or in in vivo contexts as a therapeutic approach towards the treatment or prevention of proliferative disorders, such as tumorigenic cancers.

In still another aspect, the present invention provides methods of treating proliferative disorders. The methods may be practiced in animals in veterinary contexts or in humans. The methods generally involve administering to an animal or human subject an amount of a 2,4-pyrimidinediamine compound or prodrug, or an acceptable salt, hydrate, solvate, N-oxide and/or composition thereof, effective to treat the disorder. Proliferative disorders that can be treated according to the methods include, but are not limited to, tumorigenic cancers.

Other aspects of the present invention include, but are not limited to, intermediates and methods useful for synthesizing the compound and prodrugs, as will be described in more detail herein below.

5. DETAILED DESCRIPTION

5.1 Definitions

As used herein, the following terms are intended to have the following meanings.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to alkyl groups having from 1 to 8 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. A "lower alkyldiyl" is an alkyldiyl group having from 1 to 6 carbon atoms. In preferred embodiments the alkyldiyl groups are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkylene group is (C1-C6) or (C1-C3) alkylene. Also preferred are straight-chain saturated alkano groups, e.g., methano, ethano, propano, butano, and the like.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. "Lower cycloalkyl" refers to a cycloalkyl group having from 3 to 8 ring carbon atoms.

"Cycloalkylalkyl" by itself or as part of another substituent refers to an alkyl group that comprises a linear or branched portion and a cyclic portion. Typical cycloalkylalkyl groups include, but are not limited to, cyclopropylmethyl, 1-cycopropyleth-1-yl, 2-cyclopropyleth-1-yl, cyclobutylmethyl, 1-cycobytyleth-1-yl, 2-cyclobutyleth-1-yl, cyclopentylmethyl, 1-cycopentyleth-1-yl, 2-cyclopentyleth-1-yl, cyclohexylmethyl, 1-cycohexyleth-1-yl, 2-cyclohexleth-1-yl, and the like. "Lower cycloalkylalkyl" refers to a cycloalkylalkyl group in which the linear or branched portion contains from 1 to 4 carbon atoms and the cyclic portion contains from 3 to 8 carbon atoms.

"Heteroalkyl" by itself or as part of another substituent refers to an alkyl group in which at least one of the carbon atoms is replaced with a heteroatom, for example, a heteroatom selected from O, S and N. In heteroalkyl groups including more than one heteroatom, the heteroatoms may be the same or they may be different. Like an alkyl group, a heteroalkyl can be linear, branched or cyclic in structure, and can be saturated or unsaturated. Typical heteroalkyl groups include, but are not limited to, —CH$_2$—O—CH$_2$—, —CH$_2$—S—CH$_2$—, —CH$_2$—NH—CH$_2$—, —CH$_2$—N(CH$_3$)—CH$_2$—,

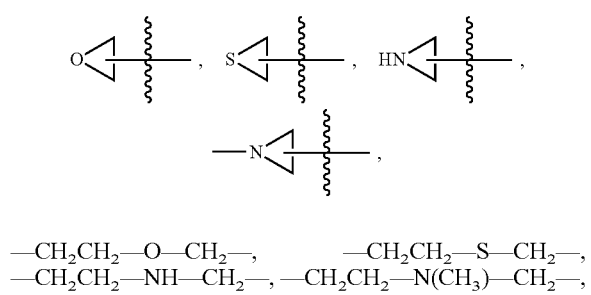

—CH$_2$CH$_2$—O—CH$_2$—, —CH$_2$CH$_2$—S—CH$_2$—, —CH$_2$CH$_2$—NH—CH$_2$—, —CH$_2$CH$_2$—N(CH$_3$)—CH$_2$—,

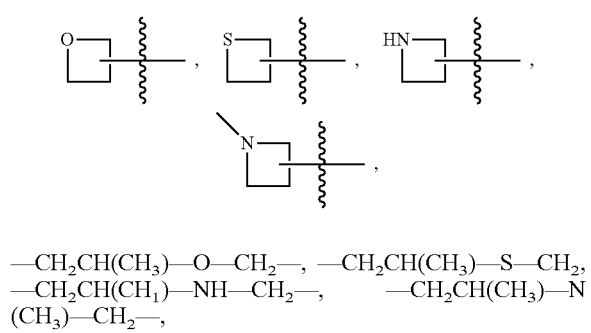

—CH$_2$CH(CH$_3$)—O—CH$_2$—, —CH$_2$CH(CH$_3$)—S—CH$_2$, —CH$_2$CH(CH$_1$)—NH—CH$_2$—, —CH$_2$CH(CH$_3$)—N(CH$_3$)—CH$_2$—,

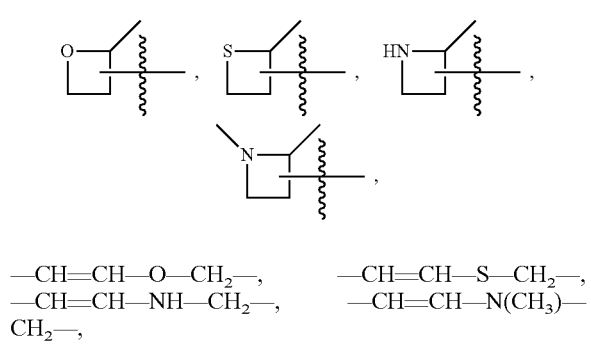

—CH=CH—O—CH$_2$—, —CH=CH—S—CH$_2$—, —CH=CH—NH—CH$_2$—, —CH=CH—N(CH$_3$)—CH$_2$—,

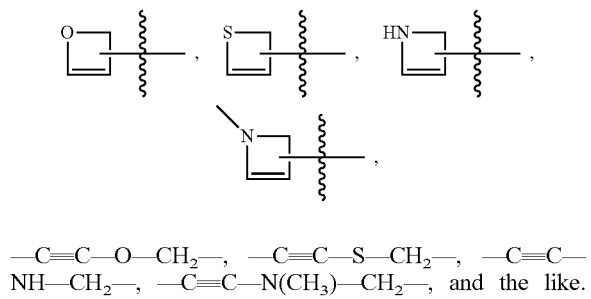

—C≡C—O—CH$_2$—, —C≡C—S—CH$_2$—, —C≡C—NH—CH$_2$—, —C≡C—N(CH$_3$)—CH$_2$—, and the like.

Where specific levels of saturation are intended, the nomenclature "heteroalkanyl," "heteroalkenyl," and heteroalkynyl" is used. "Lower heteroalkyl" refers to a heteroalkyl group having from 1 to 8 carbon and heteroatoms.

"Cycloheteroalkyl" by itself or as part of another substituent refers to a cyclic version of a heteroalkyl. Typical examples of cycloheteroalkyl groups include, but are not limited to,

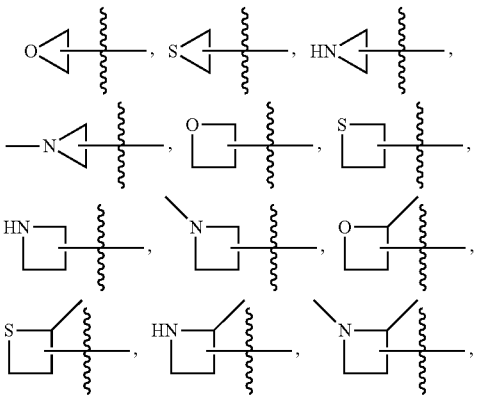

and the like. "Lower cycloheteroalkyl" refers to a cycloheteroalkyl group having from 3 to 8 ring atoms.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are phenyl and naphthyl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As non-limiting examples, "alkyloxy" or "alkoxy" refers to a group of the formula —OR, "alkylamine" refers to a group of the formula —NHR and "dialkylamine" refers to a group of the formula —NRR, where each R is independently an alkyl. As another non-limiting example, "haloalkoxy" or "haloalkyloxy" refers to a group of the formula —OR', where R' is a haloalkyl.

"Prodrug" refers to a derivative of an active 2,4-pyrimidinediamine compound (drug) that may require a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking a functional group in the 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active 2,4-pyrimidinediamines compounds to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Proliferative disorder" refers to a disease or disorder characterized by aberrant cell proliferation, for example where cells divide more than their counterpart normal cells. The aberrant proliferation may be caused by any mechanism of action or combination of mechanisms of action. For example, the cell cycle of one or more cells may be affected such that cell(s) divide more frequently than their counterpart normal cells, or alternatively, one or more cells may bypass inhibitory signals which would normally limit their number of divisions. Proliferative diseases include, but are not limited to, slow or fast growing tumors and cancers.

"Antiproliferative compound" refers to a compound that inhibits the proliferation of a cell as compared to an untreated control cell of a similar type. The inhibition can be brought about by any mechanism or combination of mechanisms, and may operate to inhibit proliferation cytostatically or cytotoxically. As a specific example, inhibition as used herein includes, but is not limited to, arrest of cell division, a reduction in the rate of cell division, proliferation and/or growth and/or induction of cell death.

"Pharmaceutically effective amount" or "therapeutically effective amount" refers to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or to decrease the growth rate of the tumor.

5.2 Antiproliferative 2,4-Pyrimidinediamine Compounds

The antiproliferative compounds are generally 2,4-pyrimidinediamine compounds according to structural formula (I):

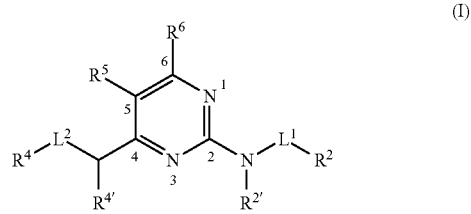

(I)

including salts, hydrates, solvates and N-oxides thereof, wherein:

L$^1$ and L$^2$ are each, independently of one another, selected from a lower alkyldiyl linker, a lower alkylene linker and a covalent bond;

R$^2$ is selected from the group consisting of lower alkyl optionally substituted with an R$^b$ group,

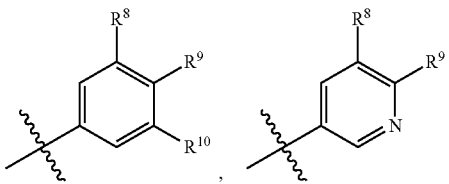

,

-continued

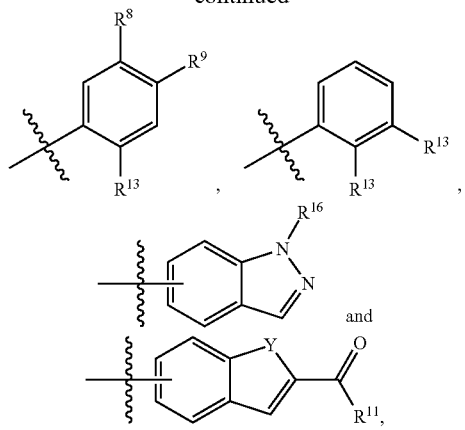

where Y is NH, O or CH$_2$;
R$^{2'}$ is hydrogen, methyl or lower alkyl;
R$^{4'}$ is hydrogen, methyl or lower alkyl;
R$^4$ is selected from the group consisting of lower alkyl optionally monosubstituted with an R$^a$ or R$^b$ group, lower cycloalkyl optionally monosubstituted with an R$^a$ or R$^b$ group, lower cycloheteroalkyl optionally substituted at one or more ring carbon and/or heteroatoms with an R$^a$ or R$^b$ group, —(CR$^a$R$^a$)$_n$—R$^b$,

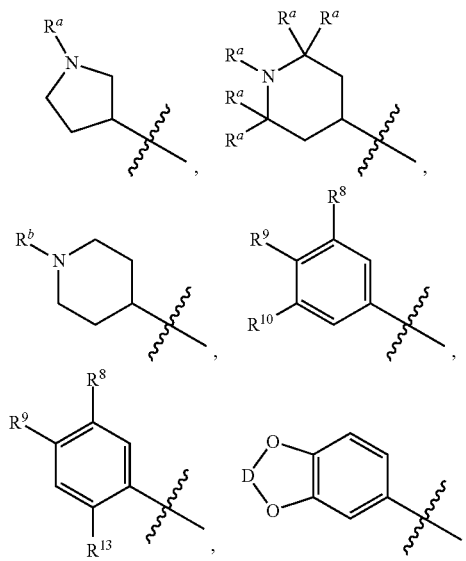

where D is —(CR$^7$R$^7$)$_m$—,

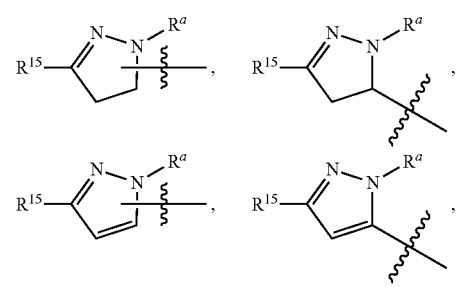

-continued

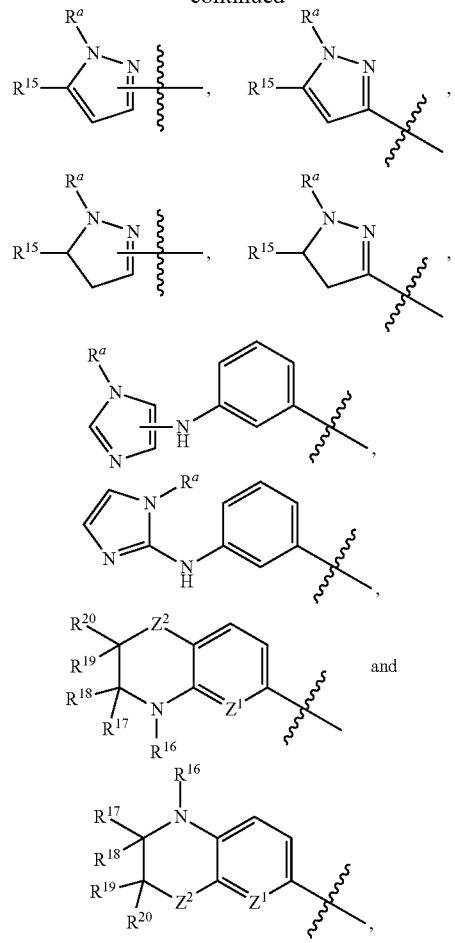

where Z$^1$ is N or CH and Z$^2$ is O, S, NH, S(O) or S(O)$_2$;
R$^5$ is selected from the group consisting of halo, fluoro and —CF$_3$;
R$^6$ is hydrogen;
each R$^7$ is independently selected from the group consisting of hydrogen, methyl, lower alkyl and halo;
each R$^8$ is independently selected from the group consisting of hydrogen, lower alkyl, —(CH$_2$)$_n$—OH, —OR$^a$, —(CH$_2$)$_n$—NR$^c$R$^c$, —O(CH$_2$)$_n$—R$^a$, —O(CH$_2$)$_n$—R$^b$, —C(O)OR$^a$, —C(S)OR$^{a'}$ halo, —CF$_3$ and —OCF$_3$;
each R$^9$ is independently selected from the group consisting of hydrogen, lower alkyl, —OR$^a$, —(CH$_2$)$_n$—NR$^c$R$^c$, —O(CH$_2$)$_n$—R$^a$, —O(CH$_2$)$_n$—R$^b$, —C(O)—NR$^c$R$^c$, —C(S)—NR$^c$R$^c$, —S(O)$_2$—NR$^c$R$^c$, —NHC(O)R$^a$, —NHC(S)R$^a$, —C(O)—NH—(CH$_2$)$_n$—NR$^c$R$^c$, —C(S)—NH—(CH$_2$)$_n$—NR$^c$R$^c$, halo, —CF$_3$, —OCF$_3$,

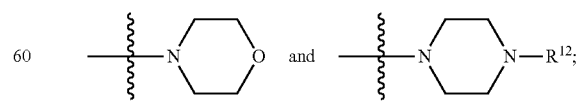

each R$^{10}$ is independently selected from the group consisting of hydrogen, lower alkyl, —(CH$_2$)$_n$—OH, —(CH$_2$)$_n$—NR$^c$R$^c$, —OR$^a$, —O(CH$_2$)$_n$—R$^a$, —O(CH$_2$)$_n$—R$^b$, halo, —CF$_3$, —OCF$_3$,

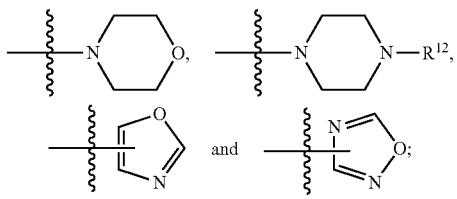

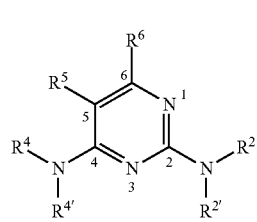

(II)

- each $R^{11}$ is independently selected from the group consisting of —$OR^a$, —$NR^cR^c$ and —$NR^aR^d$;
- each $R^{12}$ is independently selected from the group consisting of lower alkyl, arylalkyl, —$OR^a$, —$NR^cR^c$, —$C(O)R^a$, —$C(O)OR^a$ and —$C(O)NR^cR^c$;
- each $R^{13}$ is independently selected from the group consisting of lower alkyl, hydroxy, lower alkoxy, methoxy, —$C(O)NR^cR^c$ and —$C(O)NH_2$;
- each $R^{15}$ is independently selected from the group consisting of hydrogen, lower alkyl, lower cycloakyl and phenyl;
- each $R^{16}$ is independently selected from the group consisting of hydrogen, methyl, lower alkyl, lower cycloalkyl, lower branched alkyl and lower cycloalkylmethyl;
- each $R^{17}$ is independently selected from the group consisting of hydrogen, lower alkyl, methyl and $R^d$ or, alternatively, $R^{17}$ may be taken together with $R^{18}$ to form an oxo (=O) group;
- each $R^{18}$ is independently selected from the group consisting of hydrogen, lower alkyl and methyl or, alternatively, $R^{18}$ may be taken together with $R^{17}$ to form an oxo (=O) group;
- each $R^{19}$ is independently selected form the group consisting of hydrogen, lower alkyl, methyl and $R^d$;
- each $R^{20}$ is independently selected from the group consisting of hydrogen, lower alkyl, methyl and $R^d$;
- each m is independently an integer from 1 to 3;
- each n is independently an integer from 1 to 3;
- each $R^a$ is independently selected from the group consisting of hydrogen, lower alkyl, lower cycloalkyl, lower cycloalkylalkyl, phenyl and benzyl;
- each $R^b$ is independently selected from the group consisting of —$OR^a$, —$CF_3$, —$OCF_3$, —$NR^cR^c$, —$C(O)R^a$, —$C(S)R^a$, —$C(O)OR^a$, —$C(S)OR^a$, —$C(O)NR^cR^c$, —$C(S)NR^cR^c$, —$S(O)_2NR^cR^c$, —$C(O)NR^aR^d$, —$C(S)NR^aR^d$ and —$S(O)_2NR^aR^d$;
- each $R^c$ is independently selected from the group consisting of hydrogen, lower alkyl and lower cycloalkyl, or, alternatively, two $R^c$s may be taken together with the nitrogen atom to which they are bonded to form a 5-7 membered saturated ring which optionally includes 1-2 additional heteroatomic groups selected from O, $NR^a$, $NR^a$—$C(O)R^a$, $NR^a$—$C(O)OR^a$ and $NR^a$—$C(O)NR^a$; and
- each $R^d$ is independently selected from lower monohydroxyalkyl and lower di-hydroxyalkyl.

An important class of compounds of structural formula (I) includes compounds in which $L^1$ and $L^2$ are each a covalent bond, such that the compound is a 2,4-pyrimidine diamine according to structural formula (II):

including salts, hydrates, solvates and N-oxides thereof, wherein $R_2$, $R^{2'}$, $R^4$, $R^{4'}$, $R^5$ and $R^6$ are as previously defined for structural formula (I).

An important class of compounds of structural formulae (I) and/or (II) and the salts, hydrates, solvates and N-oxides thereof, includes compounds in which $R^5$ is fluoro.

Another important class of compounds of structural formulae (I) and/or (II) and the salts, hydrates, solvates and N-oxides thereof, includes compounds in which $R^{2'}$ is hydrogen.

Another important class of compounds of structural formulae (I) and/or (II) and the salts, hydrates, solvates and N-oxides thereof, includes compounds in which $R^{2'}$ and $R^{4'}$ are each, independently of one another, selected from hydrogen and methyl.

Another important class of compounds of structural formulae (I) and/or (II) and the salts, hydrates, solvates and N-oxides thereof, includes compounds in which $R^{4'}$ is methyl.

Other important classes of compounds of structural formulae (I) and/or (II) include compounds according to structural formulae (III)-(V):

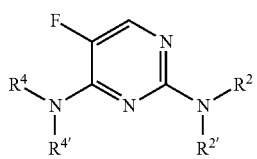

(III)

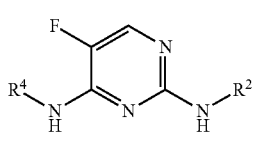

(IV)

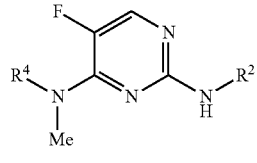

(V)

and salts, hydrates, solvates and N-oxides thereof, wherein $R^2$, $R^{2'}$, $R^4$ and $R^{4'}$, are as previously defined for structural formula (I).

When $R^2$ and/or $R^4$ is

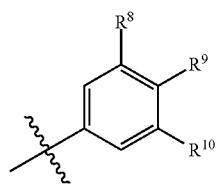

in the compounds described herein, for example, the compounds of structural formulae (I)-(V), in some embodiments, $R^9$ and $R^{10}$ are not both simultaneously lower alkoxy or methoxy. In other embodiments, $R^8$, $R^9$ and $R^{10}$ are not each simultaneously lower alkoxy or methoxy. In still other embodiments $R^8$, $R^9$ and $R^{10}$ are each methoxy or lower alkoxy. In yet other embodiments, $R^8$ is selected from hydrogen, lower alkyl, lower alkoxy, —$OR^a$, halo, —$CF_3$ and —$OCF_3$ and one of $R^9$ or $R^{10}$ is selected from

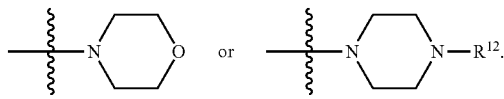

In a specific embodiment, the other one of $R^9$ or $R^{10}$ is other than

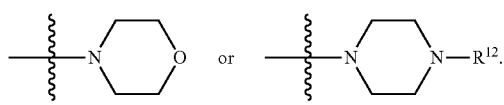

In yet other embodiments, $R^8$ is selected from hydrogen, lower alkyl, —$OR^a$, halo, —$CF_3$ and —$OCF_3$ and one of $R^9$ or $R^{10}$ is selected from —$OCH_2C(O)R^a$, —$OCH_2C(O)OR^a$, —$OCH_2C(O)NHR^a$, —$OCH_2C(O)NHR^d$ and —$OCH_2C(O)NR^cR^c$. In a specific embodiment, the other one of $R^9$ or $R^{10}$ is other than —$OCH_2C(O)R^a$, $OCH_2C(O)OR^a$, —$OCH_2C(O)NHR^a$, —$OCH_2C(O)NHR^d$ or —$OCH_2C(O)NR^cR^c$.

In yet other embodiments, $R^8$ and $R^9$ are each, independently of one another, selected from hydrogen, lower alkyl, —$OR^a$, halo, —$CF_3$ and —$OR^a$ and $R^{10}$ is

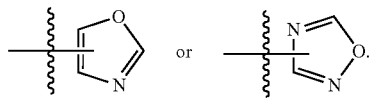

In yet other embodiments $R^9$ is hydrogen and $R^8$ and $R^{10}$ are each, independently of one another, selected from the group consisting of lower alkyl, methyl, lower alkoxy, methoxy, —$CF_3$ and —$OCF_3$. Specific combinations of $R^8$ and $R^{10}$ when $R^9$ is hydrogen are as follows:

$R^8$ and $R^{10}$ are each the same lower alkyl or methyl;
$R^8$ and $R^{10}$ are each the same lower alkoxy or methoxy;
$R^8$ is lower alkyl or methyl and $R^{10}$ is —$CF_3$;
$R^8$ is lower alkoxy or methoxy and $R^{10}$ is —$CF_3$; and
$R^8$ is lower alkyl or methyl and $R^{10}$ is —$OCF_3$.

In still other embodiments, $R^9$ is hydroxy, methoxy or chloro and $R^8$ and $R^{10}$ are each, independently of one another, selected from the group consisting of lower alkyl, methyl, lower alkoxy, methoxy and chloro. Specific combinations of $R^8$, $R^9$ and $R^{10}$ according to this embodiment are as follows:

$R^8$ and $R^{10}$ are each methyl and $R^9$ is hydroxy, methoxy or chloro;
$R^8$ and $R^{10}$ are each chloro and $R^9$ is hydroxy or methoxy; and
$R^8$ is chloro, $R^{10}$ is methyl and $R^9$ is hydroxy or methoxy.

When $R^2$ and $R^4$ are each

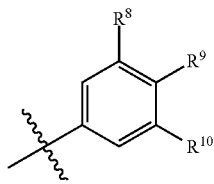

in the compounds described herein, such as, for example, the compounds of structural formulae (I)-(V), in some embodiments no more than one of $R^8$, $R^9$ and $R^{10}$ of the $R^4$ phenyl is hydrogen unless at least one of $R^8$, $R^9$ or $R^{10}$ of the $R^2$ phenyl is —$O(CH_2)_n$—$NR^cR^c$,

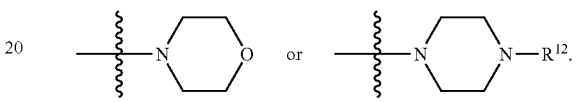

In other embodiments, the substitution patterns of the $R^2$ and $R^4$ phenyl rings are different from each other such that the compound is not a N2,N4-bis(3,4,5-substituted phenyl)pyrimidinediamine.

In still other embodiments, the compound is a compound according to structural formula (VI):

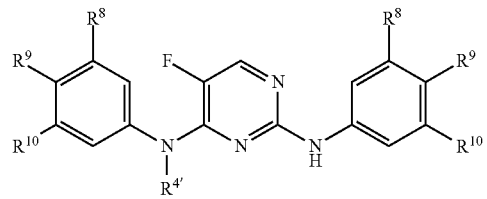

including the salts, hydrates, solvates and N-oxides thereof, wherein $R^{4'}$, $R^8$, $R^9$ and $R^{10}$ are as previously defined for structural formula (I).

In still other embodiments, the compound is a compound according to structural formula (VII):

(VII)

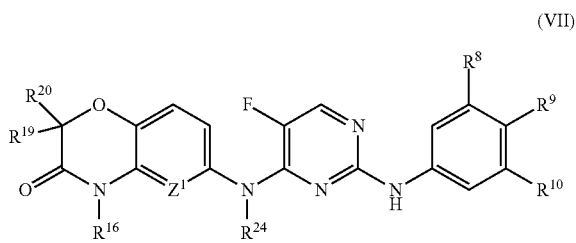

including the salts, hydrates, solvates and N-oxides thereof, wherein
$R^{16}$ and $R^{24}$ are each independently selected from hydrogen and methyl;
$R^8$ is selected from hydrogen, lower alkyl, methyl; hydroxy, lower alkoxy,
methoxy, halo, chloro, trifluoromethyl and —$CH_2OH$;
$R^9$ is selected from hydrogen, lower alkyl, methyl, hydroxy, lower alkoxy, methoxy, halo, chloro, trifluoromethyl, trifluoromethoxy, —$OCH_2C(O)NHR^a$,

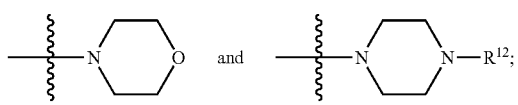 and $R^{10}$ is selected from hydrogen, lower alkyl, methyl, hydroxy, lower alkoxy, methoxy, halo, chloro, trifluoromethyl, trifluoromethoxy, —OCH$_2$C(O)NHR$^a$, —OCH$_2$C(O)OR$^a$,

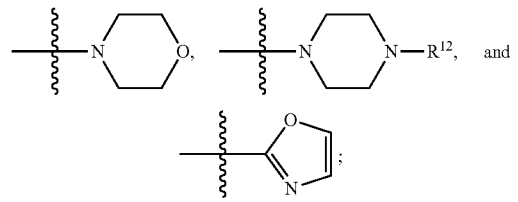

with the provisos that:
(i) when $R^9$ is

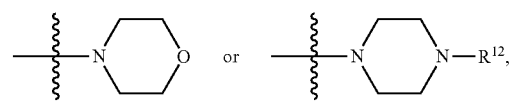

then $R^{10}$ is other than

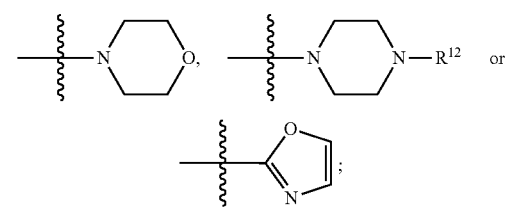

and
(ii) when $R^{10}$

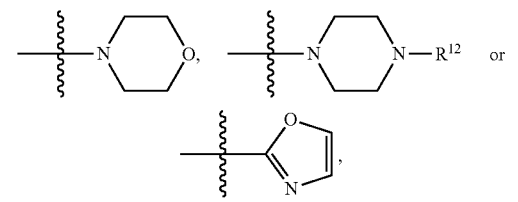

then $R^9$ is other than

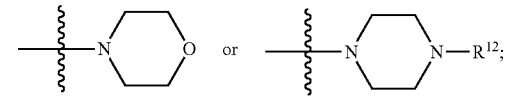

and $Z^1$, $R^{12}$, $R^{19}$, $R^{20}$, $R^a$ are as defined formula (I),

In still other embodiments when $R^2$ and $R^4$ are each

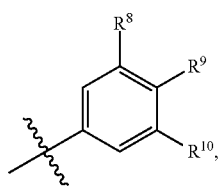

$R^8$, $R^9$ and $R^{10}$ are selected such that each $R^2$ and $R^4$ phenyl ring is mono-substituted.

In yet other embodiments when $R^2$ and $R^4$ are each

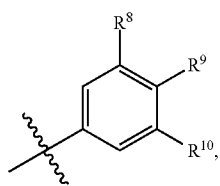

$R^8$, $R^9$ and $R^{10}$ are selected such that each $R^2$ and $R^4$ phenyl ring is di-substituted. In one specific embodiment, each $R^2$ and $R^4$ phenyl ring is substituted with an ethylenedioxy acetal group.

In still other embodiments when $R^2$ and $R^4$ are each

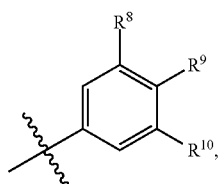

$R^{10}$ of the $R^2$ or $R^4$ ring is other than 1,3-oxazolyl or 1,3-oxazol-5-yl when the $R^8$ and $R^9$ of the same ring are each hydrogen. In one specific embodiment, $R^8$, $R^9$ and $R^{10}$ are as defined in the preceeding sentence when $R^5$ is fluoro and L$^2$ is a lower alkylene. In another specific embodiment, $R^2$ is other than 3-(1,3-oxazolyl)phenyl or 3-(1,3-oxazol-5-yl)phenyl when $R^4$ is 2-(trifluoromethyl)benzyl. In another specific embodiment, the compound is other than N2-[3-(1,3-oxazolyl)phenyl]-N4-[2-trifluoromethy)lbenzyl]-5-fluoro-2,4-pyrimidinediamine. In compounds where $R^{10}$ is an oxazolyl, the oxazolyl is not connected at the 5 position. In a specific embodiment, the oxazole is connected at the 2 position. In still another specific embodiment, the compound is not any compound described in WO 03/040141, the disclosure of which is incorporated herein by reference.

When $R^2$ is

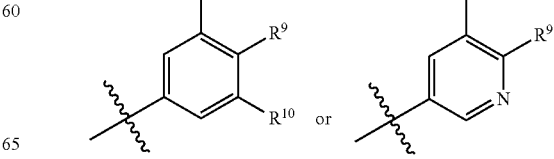

in the compounds described herein, such as, for example, the compounds of structural formulae (I)-(VII), in some embodiments one of $R^9$ or $R^{10}$ is selected from

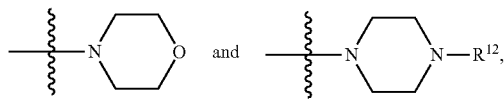

where $R^{12}$ is as previously defined for structural formula (I) and the other one of $R^9$ or $R^{10}$ is other than

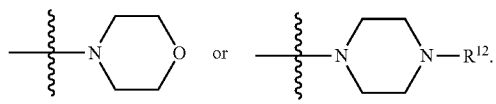

In still other embodiments, $R^8$ is selected from hydrogen, lower alkyl, methyl, lower alkoxy, methoxy and halo and one of $R^9$ or $R^{10}$ is —OCH$_2$—$R^b$, where $R^b$ is selected from —C(O)NR$^a$ and —C(O)NHR$^a$, and the other one of $R^9$ or $R^{10}$ is selected from hydrogen, lower alkyl, methyl, lower alkoxy, methoxy and halo. In still other embodiments $R^2$ is

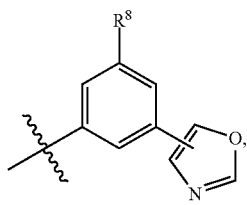

where $R^8$ is hydrogen, fluoro or CF$_3$. In a specific embodiment, $R^2$ is

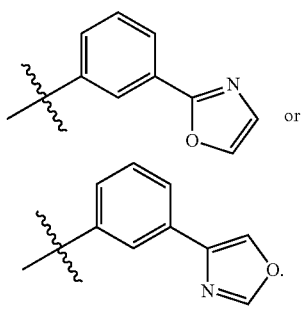

When $R^2$ is

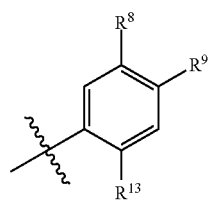

in the compounds described herein, such as, for example, the compounds according to structural formulae (I)-(V), in some embodiments, $R^8$ and $R^9$ are each independently selected from hydrogen, lower alkyl, methyl, lower alkoxy, methoxy, halo and chloro. One specific embodiment, $R^8$, $R^9$ and $R^{13}$ are each independently selected from halo, lower alkyl, methyl, lower alkoxy, and methoxy. In another specific embodiment, $R^2$ is selected from

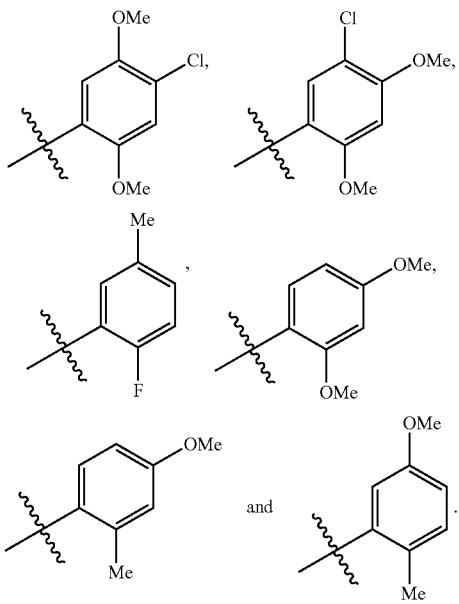

In some embodiments of compounds in which $R^2$ is

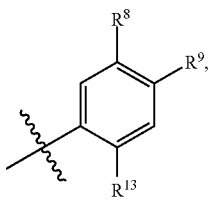

including any of the above-described specific embodiments, $R^4$ is selected from

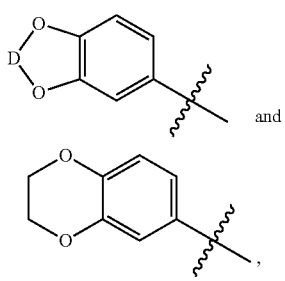

where D is as previously defined for structural formula (I).

When $R^2$ is 3,4,5-trimethoxyphenyl or 3,4,5-tri(loweralkoxy)phenyl in the compounds described herein, such as, for example the compounds of structural formulae (I)-(V), in some embodiments, $R^4$ is

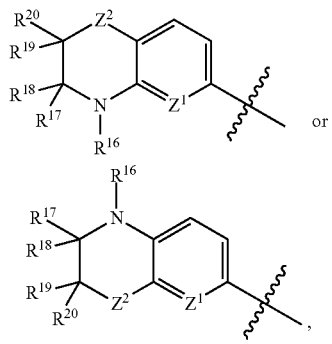

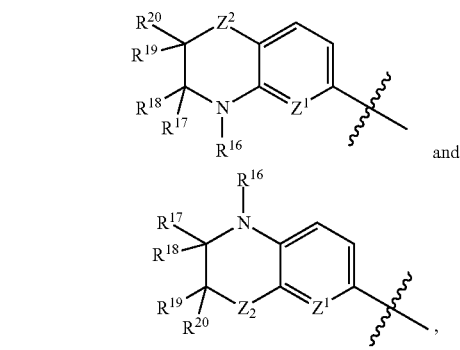

where $Z^1$, $Z^2$ and $R^{16}$, $R^{17}$, $R^{18}$, $R^{19}$ and $R^{20}$ are as previously described for structural formula (I).

When $R^9$ or $R^{10}$ is

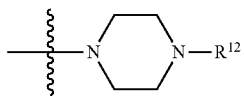

in the compounds described herein, such as, for example, the compounds of structural formulae (I)-(VII), in some embodiments $R^{12}$ is methyl. In other embodiments, $R^{12}$ is —C(O)$R^a$ or —C(O)O$R^a$, where $R^a$ is lower alkyl, ethyl or methyl.

When $R^2$ is

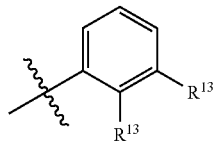

in the compounds described herein, such as, for example, the compounds of structural formulae (I)-(V), in some embodiments (i) each $R^{13}$ is, independently or the other, selected from lower alkyl, methyl, hydroxy, lower alkoxy and methoxy; and/or (ii) $R^4$ is selected from where $Z^1$, $Z^2$ and $R^{16}$, $R^{17}$, $R^{18}$, $R^{19}$ and $R^{20}$ are as previously described for structural formula (I). In a specific embodiment, $R^4$ is

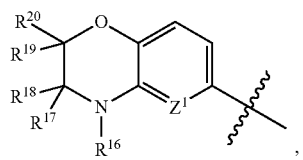

where $Z^1$ is CH, $R^{16}$ is hydrogen, $R^{17}$ and $R^{18}$ are taken together to form an oxo (=O) group and $R^{19}$ and $R^{20}$ are each hydrogen or methyl; and $R^2$ is

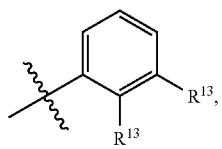

where each $R^{13}$ is, independently of the other, selected from lower alkyl, methyl, hydroxy, lower alkoxy and methoxy.

When $R^2$ is lower alkyl in the compounds described herein, such as, for example, the compounds of structural formulae (I)-(V), in some embodiments, $R^4$ is

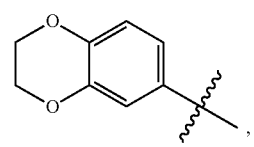

where D is as previously defined for structural formula (I).

When $R^2$ is

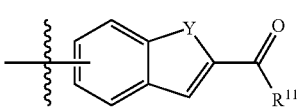

in the compounds described herein, such as, for example, the compounds of structural formulae (I)-(V), in some embodiments, $R^{11}$ is selected from the group consisting of hydroxy, methoxy, ethoxy, —NHCH$_3$, —NHCH$_2$CH$_2$OH, —NHCH$_2$CH(OH)CH$_2$OH, —NHCH$_2$CH(OH)(CH$_3$)$_2$, —N(CH$_3$)CH$_2$CH$_2$OH and —N(CH$_3$)C(CH$_3$)$_2$CH$_2$OH and Y is as previously defined.

When $R^2$ is

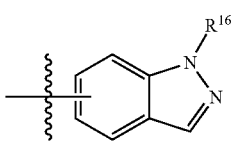

in the compounds described herein, such as the compounds of structural formulae (I)-(V), in some embodiments the ring is connected to the remainder of the molecule at the 5-position

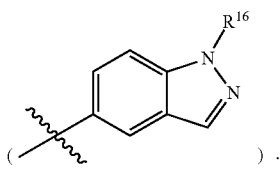

In other embodiments, it is connected to the remainder of the molecule at the 6-position

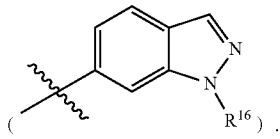

In some embodiments, $R^{16}$ is selected from lower n-alkanyl, lower branched alkanyl, lower cycloalkanyl and lower cycloalkanylmethyl. In some embodiments, $R^4$ is selected from

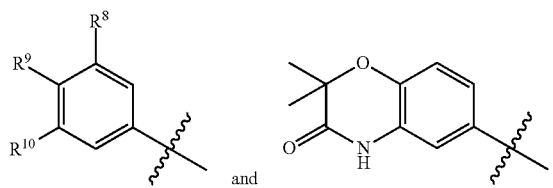

When $R^2$ is

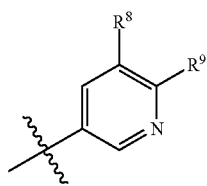

in the compounds described herein, such as, for example, the compound of structural formulae (I)-(V), in some embodiments, $R^4$ is selected from lower cycloalkyl and lower cycloheteroalkyl optionally substituted at one or more ring carbon or heteroatoms with an $R^a$ or an $R^b$ group. In a specific embodiment, $R^4$ is selected from cyclopropyl, cyclobutyl, cyclopentyl, cyclohexyl,

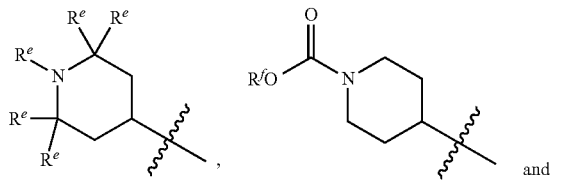

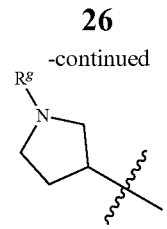

where $R^e$ and $R^f$ are selected from (C1-C3) alkanyl and methyl and $R^g$ is benzyl. In some embodiments, each $R^e$ is methyl. In some embodiments, $R^f$ is ethyl.

When $R^4$ is selected from lower alkyl, isopropyl, t-butyl, lower cycloalkyl,

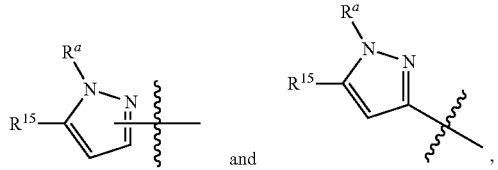

in the compounds described herein, such as, for example, the compounds of structural formulae (I)-(V), in some embodiments $R^2$ is selected from

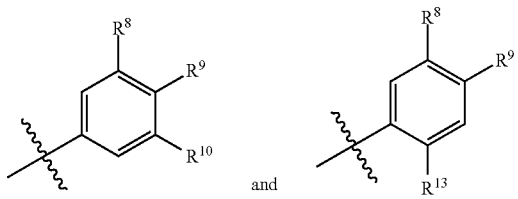

where $R^8$, $R^9$, $R^{10}$ and $R^{13}$ are as previously defined for structural formula (I). In a specific embodiment, $R^2$ is selected from any of the above-described embodiments of these substituted phenyls. In other embodiments, $R^2$ is

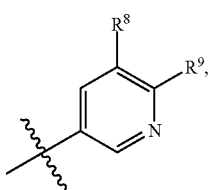

where $R^8$ and $R^9$ are a previously defined for structural formula (I).

When $R^4$ is

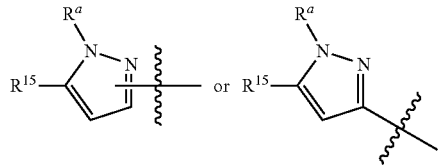

where $R^{15}$ is lower branched alkyl or t-butyl, and $R^2$ is

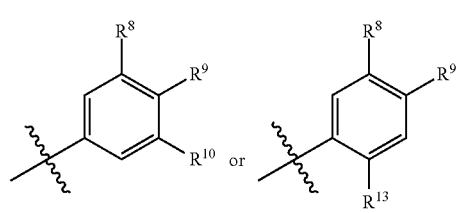

in the compounds described herein, such as, for example, the compounds of structural formulae (I)-(V), in some embodiments at least one of $R^8$ or $R^{10}$ is other than hydrogen. In other embodiments, at least two of $R^8$, $R^9$ and $R^{10}$ are other than hydrogen. In still other embodiments, at least two of $R^8$, $R^9$ and $R^{13}$ are other than hydrogen.

In still other embodiments, either: (i) $R^9$ is

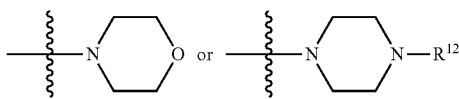

and $R^{10}$ is other than

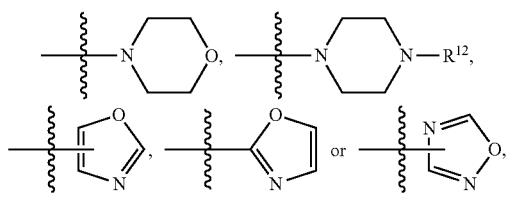

or (ii) $R^{10}$ is

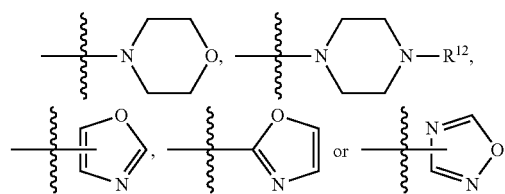

and $R^9$ is other than

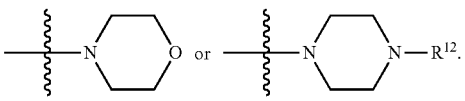

In a specific embodiment of alternative (i), $R^{10}$ is hydrogen.
In a specific embodiment of alternative (ii), $R^9$ is hydrogen.

In still other embodiments, when $R^2$ is

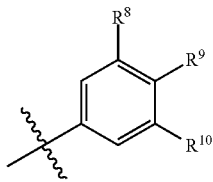

where $R^8$ and $R^9$ are each hydrogen, then $R^{10}$ is other than lower branched alkyl, t-butyl or —O(CH$_2$)$_n$R$^b$, where n is as previously defined for structural formula (I) and $R^b$ is selected from —NR$^c$R$^c$, —C(O)OR$^a$, —C(O)NR$^c$R$^c$ and —C(O)NR$^a$R$^d$.

In still other embodiments, when $R^2$ is

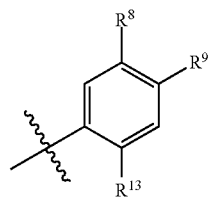

where $R^9$ is hydrogen and $R^{13}$ is selected from hydrogen, lower alkyl and methyl, then $R^8$ is other than —O(CH$_2$)$_n$R$^b$, where n is as previously defined for structural formula (I) and $R^b$ is —NR$^c$R$^c$. In still other embodiments, the compound is not any compound described in WO 01/64656, WO 03/026665 or WO 03/026666, the disclosures of which are incorporated herein by reference.

When $R^4$ is —(CH$_2$)$_n$—R$^b$ in the compounds described herein, such as, for example, the compounds of structural formulae (II)-(V), in some embodiments $R^b$ is selected from the group consisting of —OR$^a$, —NR$^c$R$^c$, —C(O)R$^a$ and —C(O)NR$^c$R$^c$, where each $R^c$ is independently selected from hydrogen and lower alkyl.

When $R^4$ is

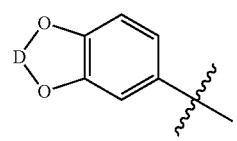

in the compounds described herein, such as, for example, the compounds of structural formulae (I)-(V), in some embodiments $R^2$ is

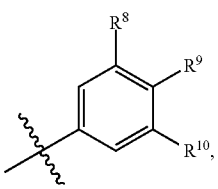

where $R^9$ is selected from the group consisting of —$OR^a$, methoxy, isopropoxy, —$OCH_2C(O)OR^a$, —$OCH_2C(O)NHR^a$, —$OCH_2C(O)NR^aR^a$ and —$OCH_2CH_2NR^aR^a$; and $R^8$ and $R^{10}$ are as previously defined for structural formula (I). In a specific embodiment, $R^8$ and $R^{10}$ are selected from one of the following combinations:

$R^8$ and $R^{10}$ are each the same lower alkyl or methyl;
$R^8$ is lower alkyl or methyl and $R^{10}$ is halo, flouro or chloro; and
$R^8$ and $R^{10}$ are each the same halo, fluoro or chloro.

When $R^4$ is selected from lower alkyl optionally monosubstituted with an $R^b$ group, a lower cycloalkyl optionally monosubstituted with an $R^b$ group and —$C(R^aR^a)_n$—$R^b$, where, $R^a$ and $R^b$ are as previously defined for structural formula (I), and/or $L^2$ is a lower alkylene linker in the compounds described herein, in some embodiments, $R^2$ is other than mono-substituted phenyl, 3-hydroxyphenyl, 3-halophenyl, 3-chlorophenyl, 3-bromophenyl, 4-halophenyl, 4-chlorophenyl, 4-bromophenyl, 3,4-dihalophenyl, 3,4-dichlorophenyl or 3,4-dichlorophenyl. In a specific embodiment, $R^2$ is other than these defined groups in compounds in which $R^5$ is —$CF_3$. In another specific embodiment, the compound is not any compound described in US 2003/0171359 and/or WO 03/032997, the disclosures of which are incorporated herein by reference.

When $R^4$ is

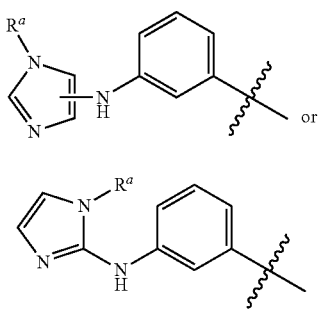

and $R^2$ is

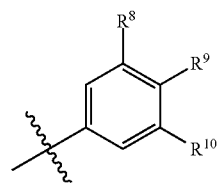

in the compounds described herein, such as, for example, the compounds of structural formulae (I)-(V), in some embodiments, $R^9$ and $R^9$ are non-bulky substitutents. In a specific embodiment, $R^9$ is other than

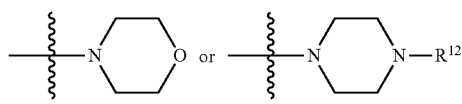

and $R^{10}$ is other than

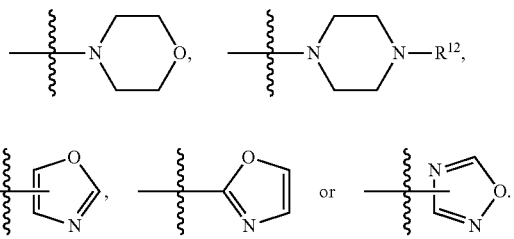

In another specific embodiment, $R^8$, $R^9$ and $R^{10}$ are each, independently of one another, selected from hydrogen lower alkyl, methyl hydroxy, lower alkoxy, methoxy, halo, fluoro and chloro. In another specific embodiment, $R^8$ is selected from hydrogen, lower alkyl, methyl, lower alkoxy and methoxy, $R^9$ is selected from hydrogen, lower alkoxy and methoxy and $R^{10}$ is selected from lower alkyl, methyl, lower alkoxy, methoxy, halo, fluoro and

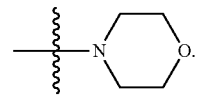

In all of the compounds described herein in which $R^4$ is

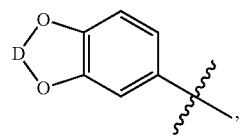

in some embodiments D is selected from the group consisting of —$CH_2$—, —$CF_2$—, —$CH_2CH_2$—, —$CF_2$—$CF_2$— and —$CH_2$—$CH_2$—$CH_2$—.

In all of the compounds described herein having lower alkyl substitutents or substituents including lower alkyl groups (e.g., lower alkoxy groups, etc.), in some embodiments the lower alkyl substituent or group is a saturated straight-chained, branched or cyclic alkyl (i.e., an alkanyl).

Additional exemplary embodiments of the compounds described herein are illustrated in the following TABLES 1-14, below.

TABLE 1A
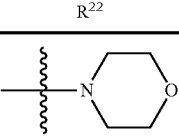
Type A
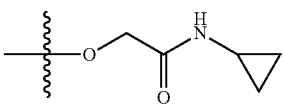
Type B
| No. | Type | n | R²¹ | R²² | R²³ | R⁴' | A549 | H1299 |
|---|---|---|---|---|---|---|---|---|
| 101 | A | 1 | H | 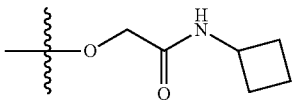 [SMILES: *OCC(=O)NC1CCC1] | H | H | + | + |
| 102 | A | 1 | H | H | 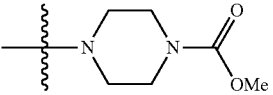 | H | + | + |
| 103 | A | 1 | H | H | 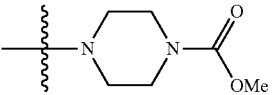 | H | + | + |
| 104 | A | 1 | H | 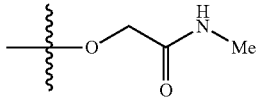 [SMILES: *OCC(=O)NC] | H | H | + | + |
| 105 | A | 1 | H | 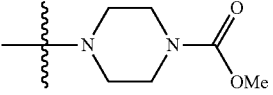 | H | H | + | + |
| 106 | A | 1 | H | H | 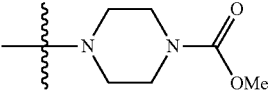 | H | + | + |
| 107 | A | 2 | H | 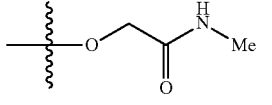 [SMILES: *OCC(=O)NC] | H | H | + | + |
| 108 | A | 2 | H | 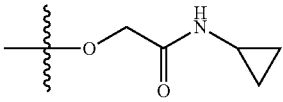 [SMILES: *OCC(=O)NC1CC1] | H | H | + | + |
| 109 | A | 2 | H | H |  | H | + | + |
| 110 | A | 2 | H | H |  | Me | + | + |

TABLE 1A-continued

Type A: 5-fluoro-N4-cyclopropyl-N2-(3,4,5-trisubstituted phenyl)pyrimidine-2,4-diamine scaffold with R21, R22, R23 on phenyl and R4' on N.

Type B: analogous pyridine variant with R21, R22 on pyridine.

| No. | Type | n | R21 | R22 | R23 | R4' | A549 | H1299 |
|---|---|---|---|---|---|---|---|---|
| 111 | A | 2 | H | Cl | Cl | H | + | + |
| 112 | A | 2 | H | OMe | Cl | H | + | + |
| 113 | A | 2 | H | H | -O-CH2-C(=O)-NH-cyclobutyl | H | + | + |
| 114 | A | 2 | H | Cl | Cl | H | + | + |
| 115 | A | 2 | H | H | 4-(methoxycarbonyl)piperazin-1-yl | H | + | + |
| 116 | A | 2 | Me | H | Me | H | + | + |
| 117 | A | 2 | OMe | H | OMe | H | + | + |
| 118 | A | 2 | OMe | H | CF3 | H | − | + |
| 119 | A | 2 | H | H | morpholin-4-yl | H | + | + |
| 120 | A | 2 | H | H | 4-(ethoxycarbonyl)piperazin-1-yl | H | + | + |
| 121 | A | 2 | H | 4-methylpiperazin-1-yl | H | H | + | + |
| 122 | A | 2 | H | 4-(ethoxycarbonyl)piperazin-1-yl | H | H | + | + |
| 123 | A | 2 | H | morpholin-4-yl | H | Me | + | + |
| 124 | A | 2 | H | 4-acetylpiperazin-1-yl | H | Me | + | + |

TABLE 1A-continued
Type A
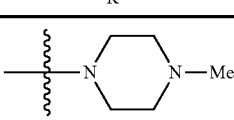
Type B
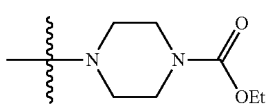
| No. | Type | n | R21 | R22 | R23 | R4' | A549 | H1299 |
|---|---|---|---|---|---|---|---|---|
| 125 | A | 2 | H | 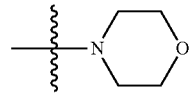 | H | Me | + | + |
| 126 | A | 2 | H | 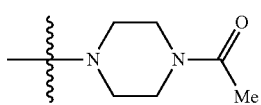 | H | Me | + | + |
| 127 | A | 2 | H | H | 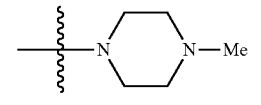 | Me | + | + |
| 128 | A | 2 | H | H | 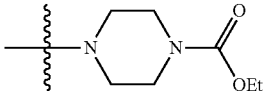 | Me | + | + |
| 129 | A | 2 | H | H | 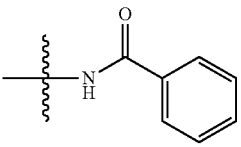 [SMILES: *NC(=O)c1ccccc1] | Me | + | + |
| 130 | A | 2 | H | H | 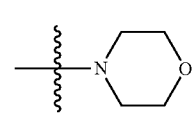 | Me | + | + |
| 131 | A | 2 | H | 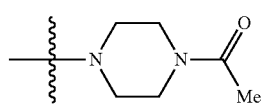 | H | H | + | + |
| 132 | A | 2 | H | 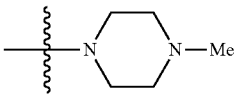 | H | H | + | + |
| 133 | A | 3 | H |  | H | H | + | + |
| 134 | A | 3 | H |  | H | H | + | + |

TABLE 1A-continued
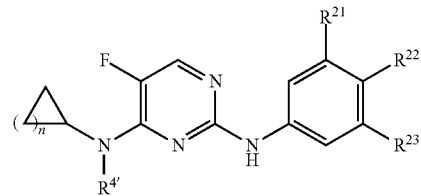
Type A
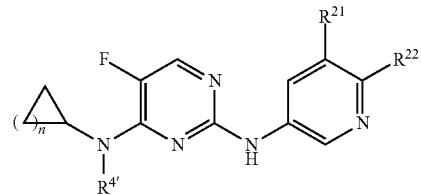
Type B
| No. | Type | n | R²¹ | R²² | R²³ | R⁴' | A549 | H1299 |
|---|---|---|---|---|---|---|---|---|
| 135 | A | 3 | H | H | morpholine | H | + | + |
| 136 | A | 3 | H | H | 4-acetylpiperazine | H | + | + |
| 137 | A | 3 | H | H | 4-methylpiperazine | H | + | + |
| 138 | A | 3 | H | H | 4-(ethoxycarbonyl)piperazine | H | + | + |
| 139 | A | 4 | H | morpholine | H | H | + | + |
| 140 | A | 4 | H | 4-acetylpiperazine | H | H | + | + |
| 141 | A | 4 | H | 4-methylpiperazine | H | H | + | + |
| 142 | A | 4 | H | 4-(ethoxycarbonyl)piperazine | H | H | + | + |
| 143 | A | 4 | H | H | morpholine | H | + | + |
| 144 | A | 4 | H | H | 4-acetylpiperazine | H | + | + |

TABLE 1A-continued
Type A
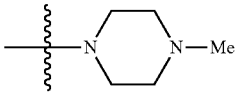
Type B
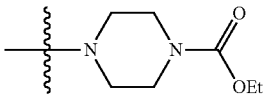
| No. | Type | n | $R^{21}$ | $R^{22}$ | $R^{23}$ | $R^{4'}$ | A549 | H1299 |
|-----|------|---|----------|----------|----------|----------|------|-------|
| 145 | A | 4 | H | H | 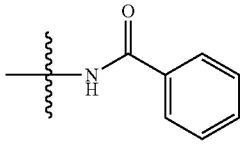 [SMILES: *NC(=O)c1ccccc1] | H | + | + |
| 146 | A | 4 | H | H | 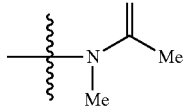 | H | + | + |
| 147 | A | 3 | H | 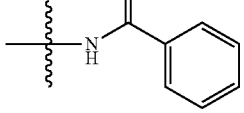 | | H | + | + |
| 148 | A | 3 | H | 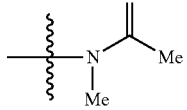 | H | H | + | + |
| 149 | A | 4 | H | 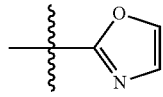 | H | H | + | + |
| 150 | A | 4 | H | 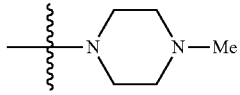 | H | H | + | + |
| 151 | A | 2 | H | H | 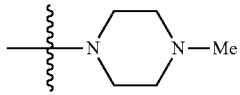 | Me | + | + |
| 152 | A | 2 | H |  | Cl | H | + | + |
| 153 | A | 4 | H |  | Cl | H | + | + |

TABLE 1A-continued

Type A: 5-fluoro-N4-cyclopropyl(alkyl)-N2-(phenyl)pyrimidine-2,4-diamine scaffold with R21, R22, R23 substituents on phenyl and R4' on N.

Type B: 5-fluoro-N4-cyclopropyl(alkyl)-N2-(pyridin-3-yl)pyrimidine-2,4-diamine scaffold with R21, R22 substituents on pyridine and R4' on N.

| No. | Type | n | R21 | R22 | R23 | R4' | A549 | H1299 |
|---|---|---|---|---|---|---|---|---|
| 154 (HCl salt) | A | 2 | H | 4-acetylpiperazin-1-yl | H | H | + | + |
| 155 (TsOH salt) | A | 4 | H | 4-methylpiperazin-1-yl | H | H | + | + |
| 156 (HCl salt) | A | 4 | H | 4-methylpiperazin-1-yl | H | H | + | + |
| 157 | A | 3 | H | 4-methylpiperazin-1-yl | Cl | H | + | + |
| 158 | A | 2 | H | 4-methylpiperazin-1-yl | Cl | H | + | + |
| 159 | A | 4 | H | 4-methylpiperazin-1-yl | Cl | H | + | + |
| 160 | A | 2 | H | 4-methylpiperazin-1-yl | Me | H | + | + |
| 161 | A | 3 | H | 4-methylpiperazin-1-yl | Me | H | + | + |
| 162 | A | 4 | H | 4-methylpiperazin-1-yl | Me | H | + | + |
| 163 | A | 2 | H | 4-methylpiperazin-1-yl | $CF_3$ | H | + | + |

TABLE 1A-continued
Type A
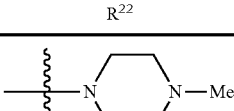
Type B
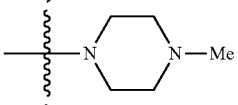
| No. | Type | n | R²¹ | R²² | R²³ | R⁴' | A549 | H1299 |
|---|---|---|---|---|---|---|---|---|
| 164 | A | 2 | H | 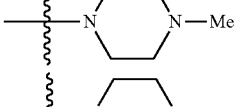 | CF₃ | H | + | + |
| 165 | A | 4 | H | 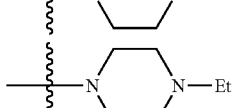 | CF₃ | H | + | + |
| 166 | A | 2 | H | 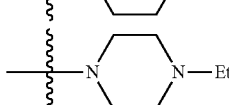 | Me | H | + | + |
| 167 | B | 2 | H | 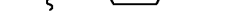 | — | H | + | + |
| 168 | B | 3 | H | 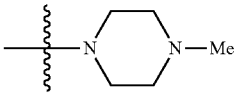 | — | H | + | + |
| 169 | B | 4 | H | 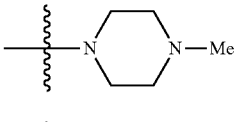 | — | H | + | + |
| 170 | A | 2 | H | 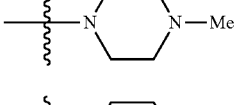 | CH₂OH | H | | |
| 171 | B | 2 | Me | 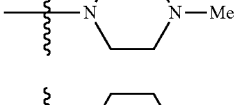 | — | H | + | + |
| 172 | B | 3 | Me | 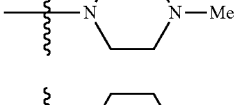 | — | H | + | + |
| 173 | B | 4 | Me | 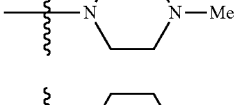 | — | H | + | + |
| 174 | A | 2 | H | 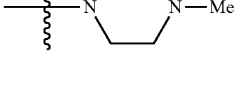 | CH₂OH | H | + | + |

TABLE 1A-continued

Type A: Structure with cyclopropyl-(CH2)n-N(R4')- attached to 4-position of 5-fluoropyrimidine, which is linked at 2-position via NH to a phenyl ring bearing R21, R22, R23.

Type B: Same as Type A but the aniline ring is replaced by a pyridine ring bearing R21, R22.

| No. | Type | n | R21 | R22 | R23 | R4' | A549 | H1299 |
|---|---|---|---|---|---|---|---|---|
| 175 | A | 3 | H | -C(CH3)2-C(O)NH2 | H | H | + | − |
| 176 | A | 3 | H | -C(CH3)2-C(O)NH-CH2CH2-N(Et)2 | H | H | + | + |
| 177 | A | 3 | H | -C(CH3)2-C(O)NH-CH2-C(O)OMe | H | H | + | + |

TABLE 1B

Type A: Structure with 1,2,2,6,6-pentamethylpiperidin-4-yl-N(R4')- attached to 4-position of 5-fluoropyrimidine, which is linked at 2-position via NH to a phenyl ring bearing R21, R22, R23.

Type B: Same as Type A but the aniline ring is replaced by a pyridine ring bearing R21, R22.

| No. | Type | R21 | R22 | R23 | R4' | A549 | H1299 |
|---|---|---|---|---|---|---|---|
| 178 | A | H | 4-methylpiperazin-1-yl | H | H | + | + |
| 179 | A | H | H | 4-methylpiperazin-1-yl | H | + | + |
| 180 | A | H | 4-methylpiperazin-1-yl | Cl | H | + | + |

TABLE 1B-continued

Type A

Type B

| No. | Type | R²¹ | R²² | R²³ | R⁴' | A549 | H1299 |
|-----|------|-----|-----|-----|-----|------|-------|
| 181 | A | H | —N(piperazine)N—Me | Me | H | + | + |
| 182 | A | H | —N(piperazine)N—Me | CF₃ | H | + | + |
| 183 | B | H | —N(piperazine)N—Et | — | H | + | + |
| 184 | B | Me | —N(piperazine)N—Me | — | H | + | + |

TABLE 1C

Type A

Type B

| No. | Type | R²¹ | R²² | R²³ | R⁴' | A549 | H1299 |
|-----|------|-----|-----|-----|-----|------|-------|
| 185 | A | H | —N(piperazine)N—Me | H | H | + | + |
| 186 | A | H | H | —N(piperazine)N—Me | H | + | + |

TABLE 1C-continued

Type A

Type B

| No. | Type | R²¹ | R²² | R²³ | R⁴' | A549 | H1299 |
|---|---|---|---|---|---|---|---|
| 187 | A | H | N-piperazine-N-Me | Cl | H | + | + |
| 188 | A | H | N-piperazine-N-Me | Me | H | + | + |
| 189 | A | H | N-piperazine-N-Me | CF₃ | H | + | + |
| 190 | B | H | N-piperazine-N-Me | — | H | + | + |

TABLE 1D

Type A

Type B

| No. | Type | R²¹ | R²² | R²³ | R⁴' | A549 | H1299 |
|---|---|---|---|---|---|---|---|
| 191 | A | H | morpholine | H | H | | |

TABLE 1D-continued
Type A
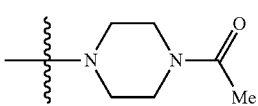
Type B
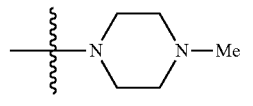
| No. | Type | $R^{21}$ | $R^{22}$ | $R^{23}$ | $R^{4'}$ | A549 | H1299 |
|---|---|---|---|---|---|---|---|
| 192 | A | H | 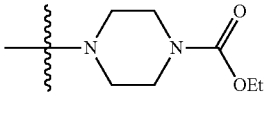 | H | H | | |
| 193 | A | H | 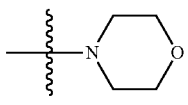 | H | H | | |
| 194 | A | H | 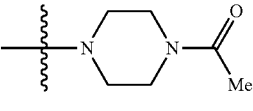 | H | H | | |
| 195 | A | H | H | 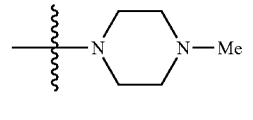 [SMILES: *N1CCN(C)CC1] | H | | |
| 196 | A | H | H |  | H | | |
| 197 | A | H | H |  | H | | |
| 198 | A | H | H |  | H | | |

TABLE 2
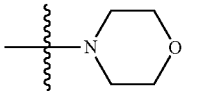
| No. | R15 | R21 | R22 | R23 | A549 | H1299 |
|---|---|---|---|---|---|---|
| 199 | t-butyl | H | H |  | + | |
| 200 | t-butyl | H | H | 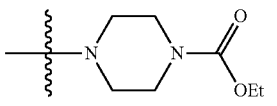 | + | + |
| 201 | t-butyl | H | H | 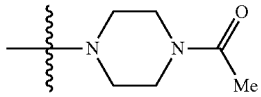 | + | + |
| 202 | t-butyl | H | 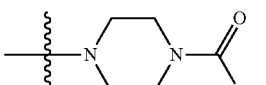 | H | + | + |
| 203 | t-butyl | H | 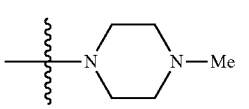 [SMILES: *N1CCN(C)CC1] | H | + | + |
| 204 | t-butyl | H | 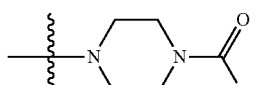 | H | + | + |
| 205 | cyclopropyl | H | H | 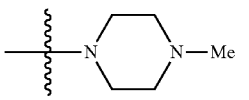 [SMILES: *N1CCN(C)CC1] | + | + |
| 206 | cyclopropyl | H | 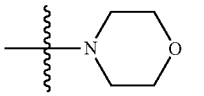 | H | + | + |
| 207 | cyclopropyl | H | H | 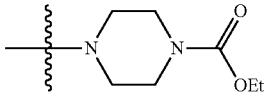 | + | + |
| 208 | cyclopropyl | H | H | 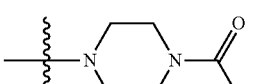 | + | + |
| 209 | cyclopropyl | H | 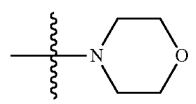 | H | + | + |
| 210 | cyclopropyl | H |  | H | + | − |

TABLE 2-continued
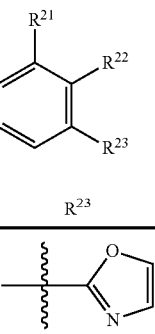
| No. | R15 | R21 | R22 | R23 | A549 | H1299 |
|---|---|---|---|---|---|---|
| 211 | cyclopropyl | H | H | 2-oxazolyl | + | + |
| 212 | cyclopropyl | H | 4-methylpiperazin-1-yl | Cl | + | + |
| 213 | cyclopropyl | H | 4-methylpiperazin-1-yl | Me | + | + |
| 214 | cyclopropyl | H | 4-methylpiperazin-1-yl | $CF_3$ | + | + |
TABLE 3
Type A / Type B
| No. | Type | R4 | R21 | R22 | R23 | A549 | H1299 |
|---|---|---|---|---|---|---|---|
| 215 | A | i-propyl | H | 4-methylpiperazin-1-yl | H | + | + |
| 216 | A | i-propyl | H | 4-methylpiperazin-1-yl | Cl | + | + |
| 217 | A | i-propyl | H | 4-methylpiperazin-1-yl | Me | + | + |

TABLE 3-continued
Type A
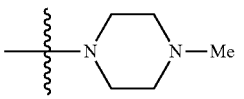 [SMILES: *N1CCN(C)CC1]
Type B
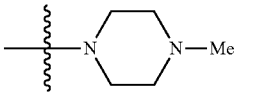 [SMILES: *N1CCN(C)CC1]
| No. | Type | R⁴ | R²¹ | R²² | R²³ | A549 | H1299 |
|---|---|---|---|---|---|---|---|
| 218 | A | i-propyl | H | 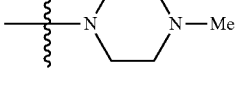 | CF₃ | + | + |
| 219 | A | i-propyl | H | H | 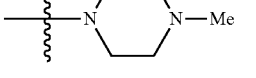 | + | + |
| 220 | A | t-butyl | H | 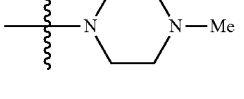 | H | + | + |
| 221 | A | t-butyl | H | H | 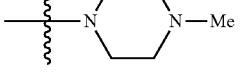 | + | + |
| 222 | A | t-butyl | H | 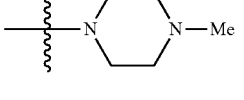 | Cl | + | + |
| 223 | A | t-butyl | H | 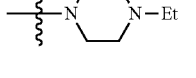 | Me | + | + |
| 224 | A | t-butyl | H | 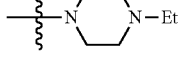 | CF₃ | + | + |
| 225 | B | i-propyl | H | 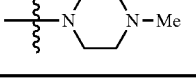 | — | + | + |
| 226 | B | t-butyl | H |  | — | + | + |
| 227 | B | i-propyl | Me |  | — | + | + |

TABLE 4

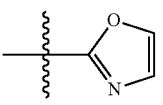

| No. | Z¹ | Z² | R¹⁶ | R¹⁹ | R²⁰ | R²¹ | R²² | R²³ | R⁴' | A549 | H1299 |
|---|---|---|---|---|---|---|---|---|---|---|---|
| 228 | CH | O | H | Me(R) | H | H | OMe | Cl | H | | |
| 229 | CH | O | H | Me(S) | H | Me | H | Me | H | + | + |
| 230 | CH | O | H | Me(R) | H | Me | H | Me | H | − | + |
| 231 | CH | O | H | Me(R) | H | Cl | OMe | H | H | − | − |
| 232 | CH | O | H | Me(R) | H | Cl | OMe | H | H | + | − |
| 236 | CH | O | H | H | H | H | H | 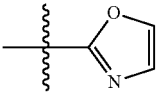 | H | + | + |
| 237 | CH | O | H | CH₂CH₂OH | H | H | H | 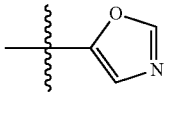 | H | + | + |
| 238 | CH | O | H | CH₂CH₂OH | H | H | H | 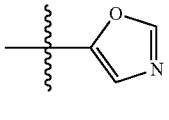 [SMILES: *c1cnco1] | H | + | + |
| 239 | CH | O | H | H | H | H | H | 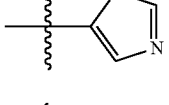 | H | − | + |
| 240 | CH | O | H | Me(S) | H | H | H | 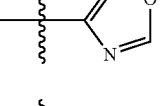 | H | + | − |
| 241 | CH | O | H | Me(R) | H | H | H | 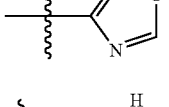 | H | | |
| 242 | CH | O | H | Me(S) | H | H | H | 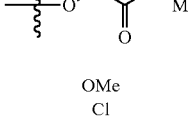 | H | | |
| 243 | CH | S | H | H | H | H | H | 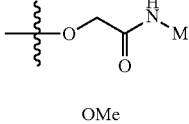 | H | | |
| 244 | CH | S | H | H | H | OMe | H | OMe | H | | |
| 245 | CH | S | H | H | H | H | OMe | Cl | H | | |
| 246 | CH | S | Me | H | H | H | H |  | H | | |
| 247 | CH | S | Me | H | H | OMe | H | OMe | H | | |
| 248 | CH | O | H | H | H | H | H | C(S)NH₂ | H | | |
| 249 | CH | O | H | CH₂CH₂OH | H | H | H | C(S)NH₂ | H | | |
| 250 | CH | S(O)₂ | H | Me | H | OMe | H | OMe | H | + | + |
| 251 | CH | S(O)₂ | H | Me | H | Me | H | Me | H | + | + |
| 252 | CH | S(O)₂ | H | Me | H | OMe | OMe | OMe | H | | |

TABLE 4-continued

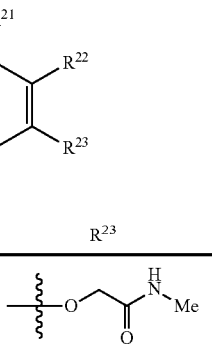

| No. | Z¹ | Z² | R¹⁶ | R¹⁹ | R²⁰ | R²¹ | R²² | R²³ | R⁴' | A549 | H1299 |
|---|---|---|---|---|---|---|---|---|---|---|---|
| 253 | CH | O | H | H | H | H | H | 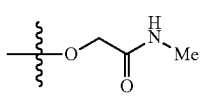 [SMILES: *OCC(=O)NC] | H | | |
| 254 | CH | O | H | H | H | H | H | OH | H | + | |
| 255 | CH | O | Me | H | H | H | H | OH | H | + | + |
| 256 | CH | O | H | Me | H | H | H | 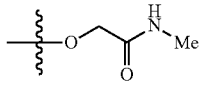 [SMILES: *OCC(=O)NC] | H | + | |
| 257 | CH | O | H | Me(S) | H | Cl | OMe | Cl | H | | |
| 258 | CH | O | H | Me(R) | H | Cl | OMe | Cl | H | | |
| 259 | CH | O | H | CH₂CH₂OH | H | OMe | H | OMe | H | | |
| 260 | CH | O | H | CH₂CH₂OH | H | Cl | OMe | H | H | | |
| 261 | CH | O | H | Me(S) | H | OMe | H | OMe | H | | |
| 262 | CH | O | H | Me(R) | H | OMe | H | OMe | H | | |
| 263 | CH | S(O)₂ | H | Me | Me | OMe | H | OMe | H | − | − |
| 264 | CH | S(O)₂ | H | Me | Me | Me | H | Me | H | − | + |
| 265 | CH | S(O)₂ | H | Me | Me | OMe | OMe | OMe | H | + | + |
| 266 | CH | S | H | Me | H | OMe | H | OMe | H | | |
| 267 | CH | S | H | Me | H | Me | H | Me | H | | |
| 268 | CH | S | H | Me | H | OMe | OMe | OMe | H | | |
| 269 | CH | S(O)₂ | H | Me | Me | H | H | 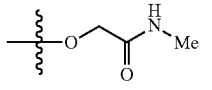 [SMILES: *OCC(=O)NC] | H | | |
| 270 | CH | S(O)₂ | H | Me | Me | H | OMe | Cl | H | | |
| 271 | CH | S | H | Me | H | H | H | 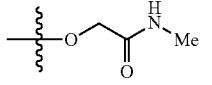 [SMILES: *OCC(=O)NC] | H | | |
| 272 | CH | S | H | Me | H | H | OMe | Cl | H | | |
| 273 | CH | S | H | H | H | H | H | OH | H | | |
| 274 | CH | S | H | Me | H | H | H | OH | H | | |
| 275 | CH | S(O)₂ | H | Me | Me | H | H | OH | H | | |
| 276 | CH | S(O)₂ | H | Me | H | H | H | OH | H | | |
| 277 | CH | S(O)₂ | H | Me | H | H | H | 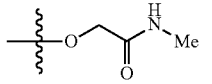 [SMILES: *OCC(=O)NC] | H | | |
| 278 | CH | S(O)₂ | H | Me | H | H | OMe | Cl | H | | |
| 279 | CH | S | H | H | H | OMe | OMe | OMe | H | | |
| 280 | CH | S | H | Me | Me | H | OMe | Cl | H | | |
| 281 | CH | S | H | Me | Me | OMe | H | OMe | H | | |
| 282 | CH | S | H | Me | Me | Me | H | Me | H | | |
| 283 | CH | S | H | Me | Me | OMe | OMe | OMe | H | | |
| 284 | CH | S | H | Me | Me | H | H | OH | H | | |
| 285 | CH | S | H | Me | Me | H | H |  | H | | |
| 286 | CH | S(O)₂ | H | Me | H | H | OMe | F | H | | |
| 287 | CH | S(O)₂ | H | Me | Me | H | OMe | F | H | + | + |
| 288 | CH | S | H | Me | H | H | OMe | F | H | + | + |
| 289 | CH | S | H | Me | Me | H | OMe | F | H | + | + |
| 290 | CH | S | H | H | H | H | OMe | F | H | + | + |
| 291 | CH | S | H | H | H | Me | O | Me | H | − | + |

TABLE 4-continued

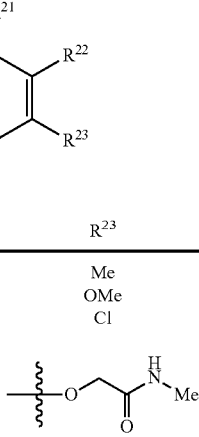

| No. | Z¹ | Z² | R¹⁶ | R¹⁹ | R²⁰ | R²¹ | R²² | R²³ | R⁴' | A549 | H1299 |
|---|---|---|---|---|---|---|---|---|---|---|---|
| 292 | CH | S(O)₂ | H | H | H | Me | O | Me | H | | |
| 293 | CH | S(O)₂ | H | H | H | OMe | H | OMe | H | | |
| 294 | CH | S(O)₂ | H | H | H | H | OMe | Cl | H | | |
| 295 | CH | S(O)₂ | H | H | H | H | H | 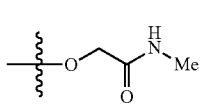 [SMILES: *OCC(=O)NC] | H | | |
| 296 | CH | S(O)₂ | H | H | H | OMe | OMe | OMe | H | | |
| 297 | CH | S(O)₂ | H | H | H | H | H | OH | H | | |
| 298 | CH | S(O)₂ | H | H | H | H | OMe | F | H | | |
| 299 | CH | O | Me | H | H | H | H | 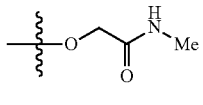 [SMILES: *OCC(=O)NC] | H | + | − |
| 300 | CH | O | H | Me(S) | H | H | H | 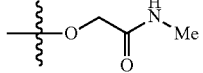 | H | + | |
| 301 | CH | O | H | Me(R) | H | H | H | 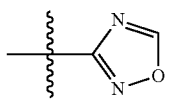 | H | | |
| 302 | CH | O | H | Me(S) | H | Cl | OMe | H | H | | |
| 303 | CH | O | H | Me(R) | H | Cl | OMe | H | H | | |
| 304 | CH | O | H | Me | Me | OMe | Me | Me | H | | |
| 305 | CH | O | H | Me | Me | OMe | H | OMe | H | + | |
| 306 | CH | O | H | Me | Me | Cl | Me | Cl | H | + | + |
| 307 | CH | O | H | Me | Me | Cl | OMe | Cl | H | + | |
| 308 | CH | O | H | Me | Me | Cl | H | Cl | H | + | |
| 309 | CH | O | H | Me | Me | OMe | H | CF₃ | H | + | |
| 310 | CH | O | H | Me | Me | Me | H | Me | H | + | |
| 311 | CH | O | H | Me | Me | OMe | H | OMe | H | + | |
| 316 | CH | O | H | Me | Me | Me | H | Me | H | | |
| 318 | CH | O | H | Me | Me | H | OMe | Cl | H | | |
| 319 | CH | O | H | Me | Me | Me | Cl | Me | H | | |
| 320 | CH | O | H | Me | Me | CH₂OH | H | CH₂OH | H | + | + |
| 321 | CH | O | H | Me | Me | Cl | H | OMe | H | + | + |
| 322 | CH | O | H | Me | Me | H | OMe | Cl | H | | |
| 323 | CH | O | H | Me | Me | OMe | H | OMe | Me | + | |
| 324 | CH | O | Me | Me | Me | Me | H | Me | Me | + | − |
| 325 | CH | O | Me | Me | Me | H | OMe | Cl | Me | + | + |
| 326 | CH | O | Me | Me | Me | OMe | H | OMe | Me | + | + |
| 327 | CH | O | H | Me | Me | H | OMe | Cl | Me | + | + |
| 328 | CH | O | Me | Me | Me | Me | H | Me | H | | |
| 329 | CH | O | Me | Me | Me | OMe | H | OMe | H | | |
| 330 | CH | O | H | Me | Me | H | C(O)NHMe | Cl | H | | |
| 331 | CH | O | H | Me | Me | H | S(O)₂NHMe | OMe | H | | |
| 332 | CH | O | H | Me | Me | H | H | 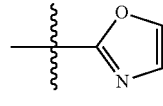 [SMILES: *c1ncco1] | H | | |
| 333 | CH | O | H | Me | Me | C(O)OMe | H |  | H | − | − |

TABLE 4-continued

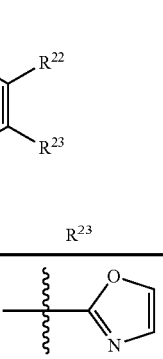

| No. | Z¹ | Z² | R¹⁶ | R¹⁹ | R²⁰ | R²¹ | R²² | R²³ | R⁴' | A549 | H1299 |
|---|---|---|---|---|---|---|---|---|---|---|---|
| 334 | CH | O | H | Me | Me | CF₃ | H |  | H | + | − |
| 335 | N | O | H | Me | Me | Me | OMe | Me | H | | |
| 338 | CH | O | H | Me | Me | OMe | OMe | OMe | H | + | + |
| 339 | CH | O | H | Me | Me | Me | 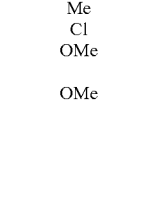 | Me | H | + | + |
| 340 | N | O | H | Me | Me | OMe | OMe | OMe | H | | |
| 350 | N | O | H | Me | Me | Me | Cl | Me | H | | |
| 352 | N | O | H | Me | Me | Cl | OH | Cl | H | + | + |
| 353 | N | O | Me | Me | Me | OMe | OMe | OMe | H | | |
| 354 | N | O | H | Me | Me | OMe | 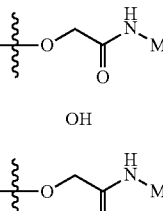 | OMe | H | + | + |
| 355 | CH | O | H | Me | Me | H | H | 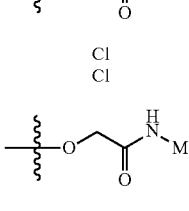 | H | + | + |
| 356 | CH | O | H | Me | Me | H | H | OH | H | + | − |
| 357 | N | O | H | Me | Me | H | H | 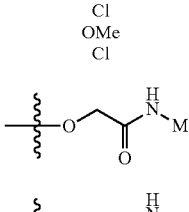 | H | | |
| 358 | CH | O | H | Me | Me | Me | OH | Cl | H | + | |
| 359 | CH | O | H | Me | Me | Me | OMe | Cl | H | + | + |
| 360 | N | O | H | Me | Me | H | H | 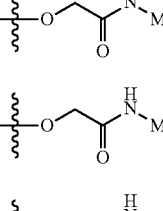 | H | | |
| 362 | N | O | H | Me | Me | H | OMe | Cl | H | | |
| 363 | N | O | H | Me | Me | OMe | H | OMe | H | | |
| 364 | N | O | H | Me | Me | H | Cl | Cl | H | | |
| 365 (HCl salt) | N | O | H | Me | Me | H | H | 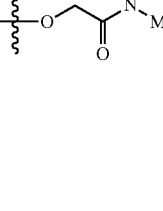 | H | | |
| 366 (bis HCl salt) | N | O | H | Me | Me | H | H |  | H | | |
| 367 (nitrate salt) | N | O | H | Me | Me | H | H |  | H | | |
| 368 (bis nitrate salt) | N | O | H | Me | Me | H | H |  | H | | |

TABLE 4-continued

| No. | Z¹ | Z² | R¹⁶ | R¹⁹ | R²⁰ | R²¹ | R²² | R²³ | R⁴' | A549 | H1299 |
|---|---|---|---|---|---|---|---|---|---|---|---|
| 369 (mesylate salt) | N | O | H | Me | Me | H | H | ~O-CH₂-C(=O)-NH-Me | H | | |
| 370 | N | O | H | Me | Me | H | H | ~O-CH₂-C(=O)-NH-Me | H | | |
| 371 | N | O | H | Me | Me | H | H | t-butyl | H | + | + |
| 372 | N | O | H | Me | Me | H | H | OH | H | – | – |
| 374 | N | O | H | Me | Me | H | OMe | F | H | – | – |
| 375 | N | O | H | Me | Me | H | H | Cl | H | – | – |
| 376 | N | O | H | Me | Me | Cl | H | Cl | H | + | + |
| 377 | CH | O | H | Me | Me | Me | OMe | Cl | H | | |
| 378 | N | O | H | Me | Me | H | OCF₃ | Cl | H | – | – |
| 379 | N | O | H | Me | Me | Me | OMe | Cl | H | | |
| 380 | N | O | H | Me | Me | H | H | ~O-CH₂-C(=O)-OMe | H | | |
| 381 | N | O | H | Me | Me | Me | OH | Cl | H | | |
| 382 | N | O | H | Me | Me | Me | OMe | Me | H | – | – |
| 383 | N | O | H | Me | Me | H | H | i-propyl | H | | |
| 385 | CH | O | H | Me | Me | Cl | OEt | Me | H | + | – |
| 386 | N | O | Me | Me | Me | Me | OMe | Cl | H | | |
| 387 | N | O | H | Me | Me | Cl | OEt | Me | H | – | – |
| 388 | N | O | Me | Me | Me | H | H | oxazol-2-yl | H | + | + |
| 389 | CH | O | H | Me | Me | Me | ~O-CH₂-C(=O)-OEt | Cl | H | | |
| 390 | N | O | Me | Me | Me | H | H | ~O-CH₂-C(=O)-NH-Me | H | | |
| 391 | CH | O | H | Me | Me | H | H | oxazol-2-yl | H | + | + |
| 392 | N | O | Me | Me | Me | H | H | oxazol-5-yl | H | | |
| 393 | CH | O | H | Me | Me | Me | ~O-cyclopentyl | Cl | H | | |
| 394 | CH | O | Me | Me | Me | H | H | oxazol-2-yl | H | + | – |

TABLE 4-continued

| No. | $Z^1$ | $Z^2$ | $R^{16}$ | $R^{19}$ | $R^{20}$ | $R^{21}$ | $R^{22}$ | $R^{23}$ | $R^{4'}$ | A549 | H1299 |
|---|---|---|---|---|---|---|---|---|---|---|---|
| 395 | CH | O | H | Me | Me | H | H | -O-CH2-C(=O)-NH-Me | Me | − | + |
| 396 | CH | O | H | Me | Me | H | H | oxazol-5-yl | H | | |
| 397 | CH | O | Me | Me | Me | H | H | oxazol-2-yl | Me | + | + |
| 398 | N | O | H | Me | Me | Me | -O-cyclopentyl | Cl | H | − | − |
| 399 | N | O | H | Me | Me | H | H | oxazol-2-yl | H | | |
| 400 | N | O | H | Me | Me | H | H | oxazol-4-yl | H | | |
| 401 | CH | O | Me | Me | Me | H | H | oxazol-4-yl | Me | + | + |
| 402 | CH | O | Me | Me | Me | Me | OMe | Me | Me | + | − |
| 403 | CH | O | Me | Me | Me | Me | -O-cyclopentyl | Cl | Me | + | − |
| 404 | N | O | Me | Me | Me | Me | OMe | Me | H | | |
| 405 | N | O | Me | Me | Me | Me | -O-cyclopentyl | Cl | H | + | + |
| 406 | N | O | H | Me | Me | H | H | oxazol-5-yl | H | | |
| 407 | CH | O | H | Me | Me | H | H | oxazol-4-yl | H | + | + |

TABLE 4-continued

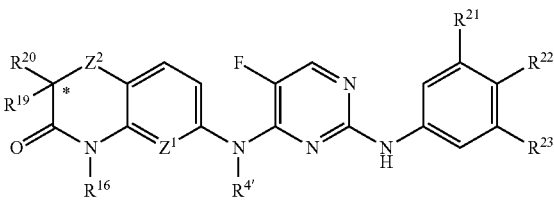

| No. | Z¹ | Z² | R¹⁶ | R¹⁹ | R²⁰ | R²¹ | R²² | R²³ | R⁴' | A549 | H1299 |
|---|---|---|---|---|---|---|---|---|---|---|---|
| 408 | N | O | H | Me | Me | Me | ⁓O-CH₂-C(O)NHMe | Cl | H | | |
| 409 | N | O | H | Me | Me | Me | ⁓O-CH₂-C(O)OEt | Me | H | | |
| 410 | CH | O | H | Me | Me | Me | i-propoxy | Cl | H | | |
| 411 | N | O | H | Me | Me | Me | i-propoxy | Cl | H | | |
| 412 | N | O | H | Me | Me | Me | ⁓O-CH₂-C(O)NHMe | Me | H | | |
| 413 | N | O | H | Me | Me | Me | ⁓O-CH₂-C(O)OEt | Cl | H | | |
| 414 | N | O | H | Me | Me | Me | ⁓O-CH₂-C(O)-CH(OH)-CH₂OH | Cl | H | — | — |
| 415 | N | O | H | Me | Me | Me | ⁓O-CH₂-C(O)NH-cyclopentyl | Me | H | | |
| 416 | CH | O | H | Me | Me | H | H | ⁓O-CH₂-C(O)NHMe | H | | |
| 417 | N | O | H | Me | Me | H | C(O)NHMe | Cl | H | | |
| 418 | N | O | H | H | H | H | H | ⁓O-CH₂-C(O)NHMe | H | | |
| 419 | N | O | H | H | H | H | ⁓N(piperazine)C(O)Me | H | H | | |
| 421 | N | O | H | H | H | H | Cl | Cl | H | | |
| 422 | N | O | H | H | H | H | OMe | Cl | H | | |
| 423 | N | O | H | H | H | Cl | OMe | Cl | H | | |
| 424 | N | O | H | H | H | OMe | H | OMe | H | | |
| 425 | N | O | H | H | H | H | OMe | F | H | | |
| 426 | N | O | H | H | H | H | OMe | H | H | | |
| 427 | N | O | H | H | H | H | OCF₃ | H | H | | |
| 428 | N | O | H | H | H | H | OEt | H | H | | |
| 429 | N | O | H | H | H | H | OBu | H | H | | |
| 430 | N | O | H | H | H | H | ⁓N-morpholine | H | H | | |
| 431 | N | O | H | H | H | H | O-iPr | H | H | | |

TABLE 4-continued

Core structure: R20, R19 on C3* of a ring with Z2, fused; N-R16; carbonyl; Z1; linked to pyrimidine (F at 5-position) with N(R4') and NH-aryl bearing R21, R22, R23.

| No. | Z1 | Z2 | R16 | R19 | R20 | R21 | R22 | R23 | R4' | A549 | H1299 |
|---|---|---|---|---|---|---|---|---|---|---|---|
| 432 | N | O | H | Me | Me | H | 4-acetylpiperazin-1-yl | H | H | | |
| 433 | N | O | H | H | H | H | OMe | OMe | H | | |
| 434 | N | O | H | Me | Me | H | morpholin-4-yl | H | H | | |
| 435 | N | O | H | H | H | H | 4-methylpiperazin-1-yl | H | H | + | + |
| 436 | N | O | H | Me | Me | H | 4-methylpiperazin-1-yl | H | H | + | |
| 437 | N | O | H | H | H | Me | H | Me | M | | |
| 438 | N | O | H | Me | Me | Me | H | Me | H | | |
| 439 | N | O | H | H | H | H | H | i-propyl | H | − | − |
| 440 | N | O | H | H | H | H | Me | Cl | H | | |
| 441 | N | O | H | H | H | CF3 | H | OMe | H | − | − |
| 442 | N | O | H | H | H | Cl | H | Cl | H | − | − |
| 443 | N | O | H | H | H | H | H | Br | H | | |
| 444 | N | O | H | H | H | H | H | t-butyl | H | | |
| 445 | N | O | H | H | H | OMe | OMe | OMe | H | | |
| 446 | N | O | H | H | H | H | F | F | H | − | − |
| 447 | N | O | H | H | H | Me | OMe | Me | H | | |
| 448 | N | O | H | H | H | Me | OH | Me | H | + | + |
| 449 | N | O | H | H | H | H | H | 4-(ethoxycarbonyl)piperazin-1-yl | H | + | + |
| 450 | N | O | H | H | H | H | H | 4-acetylpiperazin-1-yl | H | + | + |
| 451 | N | O | H | H | H | H | 4-(ethoxycarbonyl)piperazin-1-yl | H | H | − | − |
| 452 | N | O | H | H | H | H | H | morpholin-4-yl | H | | |
| 453 | N | O | H | H | H | H | H | 4-methylpiperazin-1-yl | H | + | + |
| 454 | N | O | H | Me | Me | H | H | 4-(ethoxycarbonyl)piperazin-1-yl | H | − | − |

TABLE 4-continued

| No. | Z¹ | Z² | R¹⁶ | R¹⁹ | R²⁰ | R²¹ | R²² | R²³ | R⁴' | A549 | H1299 |
|---|---|---|---|---|---|---|---|---|---|---|---|
| 455 | N | O | H | Me | Me | H | H | piperazine-N-C(O)OEt | H | + | + |
| 456 | N | O | H | Me | Me | H | piperazine-N-C(O)OEt | H | H | + | + |
| 457 | N | O | H | Me | Me | H | H | morpholine | H | | |
| 458 | N | O | H | Me | Me | H | H | N-methylpiperazine | H | + | + |
| 459 | N | O | H | Me(S) | H | H | OMe | Cl | H | | |
| 460 | N | O | H | Me(S) | H | OMe | OMe | OMe | H | | |
| 461 | N | O | H | Me(S) | H | Me | H | Me | H | | |
| 462 | CH | O | H | Me(R) | H | H | C(O)NH₂ | H | H | — | + |
| 463 | CH | O | H | Me(S) | H | CH₂NHBOC | H | H | H | | |
| 464 | CH | O | H | Me(R) | H | CH₂NHBOC | H | H | H | | |
| 465 | CH | O | H | Me(S) | H | CH₂NH₂ | H | H | H | | |
| 466 | CH | O | H | Me(R) | H | CH₂NH₂ | H | H | H | | |
| 467 | CH | O | H | Me | Me | H | H | oxazol-2-yl | H | | |
| 468 | CH | O | H | Me(S) | H | H | H | oxazol-2-yl | H | | |
| 469 | CH | O | H | Me(R) | H | H | H | oxazol-2-yl | N | H | |
| 470 | CH | O | H | Me | Me | H | C(O)NHCH₂C(O)NHMe | H | H | − | − |
| 471 | CH | O | H | Me(S) | H | H | C(O)NHCH₂C(O)NHMe | H | H | + | − |
| 472 | N | O | H | Me | Me | H | C(O)NH₂ | H | H | + | + |
| 473 | N→O | O | H | Me | Me | OMe | OMe | OMe | H | + | + |

[††]In TABLE 4, compounds having chirality at the carbon labeled with an asterisk (*) that, through substituent R¹⁹, designate a specified stereochemistry were synthesized and tested as the substantially pure enantiomer; compounds that do not designate a specified stereochemistry at this carbon atom were synthesized and, if tested, were tested as the racemate.

TABLE 5
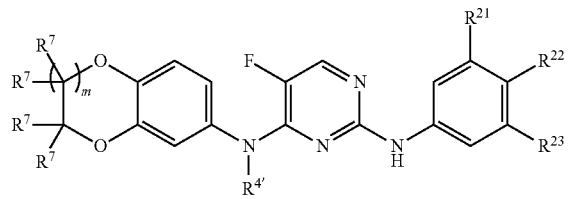
| No. | m | R⁷ | R²¹ | R²² | R²³ | R⁴' | A549 | H1299 |
|---|---|---|---|---|---|---|---|---|
| 474 | 1 | H | H | 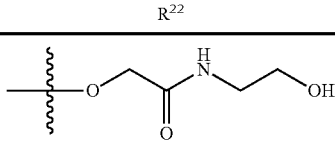 | H | H | − | |
| 475 | 1 | H | H | 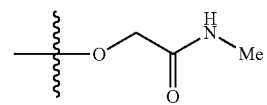 [SMILES: *OCC(=O)NC] | H | H | − | |
| 476 | 0 | F | H | H | 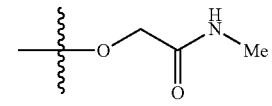 [SMILES: *OCC(=O)NC] | H | | |
| 477 | 1 | H | H | hexoxy | H | H | − | |
| 478 | 1 | H | H | OEt | H | H | + | |
| 479 | 1 | H | H | butoxy | H | H | − | |
| 480 | 1 | H | H | 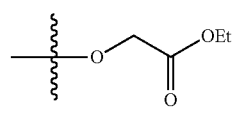 [SMILES: *OCC(=O)OCC] | H | H | − | |
| 481 | 1 | H | H | H | 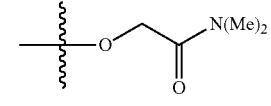 | H | − | |
| 482 | 1 | H | H | H | OH | H | − | |
| 483 | 1 | H | H | OE | H | H | − | |
| 484 | 1 | H | H | OMe | OMe | H | | |
| 485 | 1 | H | H | F | Cl | H | − | |
| 486 | 1 | H | H | t-butyl | H | H | | |
| 487 | 1 | H | H | F | H | H | − | |
| 488 | 1 | H | H | H | F | H | | |
| 489 | 1 | H | H | Et | H | H | | |
| 490 | 1 | H | H | 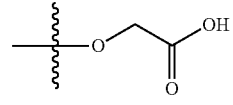 [SMILES: *OCC(=O)O] | H | H | − | |
| 491 | 1 | H | H | H | 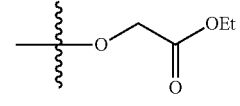 [SMILES: *OCC(=O)OCC] | H | − | + |
| 492 | 1 | H | H | H | 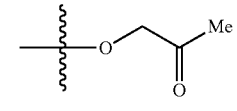 [SMILES: *OCC(C)=O] | H | − | |
| 493 | 1 | H | H | H | 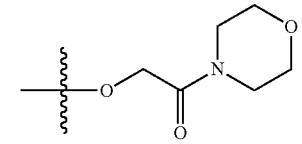 [SMILES: *OCC(=O)N1CCOCC1] | H | −/+ | + |

TABLE 5-continued
| No. | m | R⁷ | R²¹ | R²² | R²³ | R⁴' | A549 | H1299 |
|---|---|---|---|---|---|---|---|---|
| 494 | 1 | H | H | H | 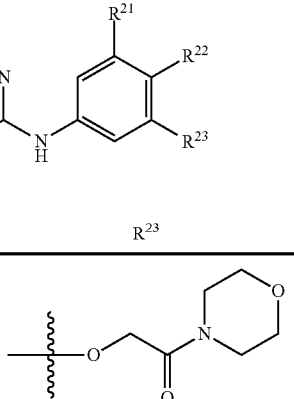 | H | + | + |
| 495 | 1 | H | H | H | 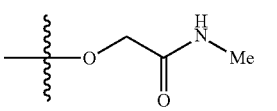 [SMILES: *OCC(=O)NC] | H | −/+ | + |
| 496 | 1 | H | H | H | 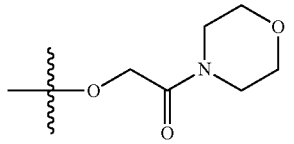 [SMILES: *OCC(=O)N1CCOCC1] | H | + | |
| 497 | 1 | H | H | H | 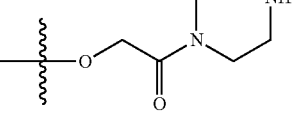 | H | + | |
| 498 | 1 | H | H | H | 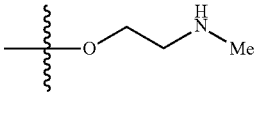 | H | − | |
| 499 | 1 | H | H | H | 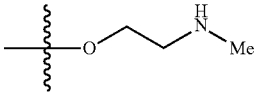 [SMILES: *OCCNC] | H | | |
| 500 | 1 | H | H | H | 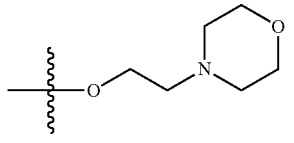 [SMILES: *OCCN1CCOCC1] | H | + | |
| 501 | 1 | H | H | 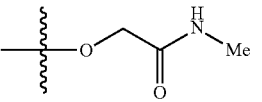 [SMILES: *OCC(=O)NC] | H | H | − | |
| 502 | 1 | H | H | 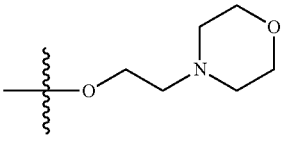 [SMILES: *OCCN1CCOCC1] | H | H | − | |
| 503 | 1 | F | H | H | 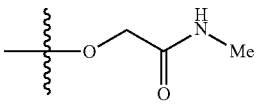 [SMILES: *OCC(=O)NC] | H | −/+ | |

TABLE 5-continued

[Structure: benzodioxine-NR4'-pyrimidine(F)-NH-phenyl(R21,R22,R23)]

| No. | m | R⁷ | R²¹ | R²² | R²³ | R⁴' | A549 | H1299 |
|---|---|---|---|---|---|---|---|---|
| 504 | 1 | H | H | H | -O-CH₂-C(=O)-NH₂ | H | + | |
| 505 | 1 | H | H | Me | -O-CH₂-C(=O)-NH-Me | H | | |
| 506 | 1 | H | OMe | OMe | OMe | H | + | |
| 507 | 1 | H | Cl | OH | Cl | H | + | |
| 508 | 1 | H | H | H | -O-CH₂-C(=O)-NH-cyclohexyl | H | − | |
| 509 | 1 | H | H | H | -O-CH₂-C(=O)-N(Me)-CH₂CH₂-OH | H | − | |
| 510 | 1 | H | H | H | -O-CH₂CH₂-N(Me)₂ | H | − | |
| 511 | 1 | H | H | i-propyl | H | H | − | |
| 512 | 1 | H | OMe | H | OMe | H | + | + |
| 513 | 0 | F | H | H | Cl | H | + | + |
| 514 | 1 | H | H | H | CF₃ | H | − | |
| 515 | 1 | H | H | H | -oxazol-2-yl | H | + | + |
| 516 | 1 | H | H | H | -O-CH₂-C(=O)-NH-Me | H | + | |
| 517 | 1 | H | H | H | -O-CH₂-C(=O)-NH-Me | H | | |
| 518 | 1 | H | H | OMe | -O-CH₂-C(=O)-NH-Me | H | | |
| 519 | 1 | H | H | H | -O-CH₂-C(=O)-NH-iPr | H | | |

TABLE 5-continued

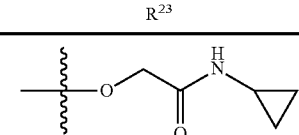

| No. | m | R⁷ | R²¹ | R²² | R²³ | R⁴' | A549 | H1299 |
|---|---|---|---|---|---|---|---|---|
| 520 | 1 | H | H | H |  | H | + | |
| 521 | 1 | H | Me | H | OH | H | + | − |
| 522 | 1 | H | F | H | $CF_3$ | H | − | − |
| 523 | 1 | H | Me | H | $CF_3$ | H | − | + |
| 524 | 1 | H | F | H | F | H | − | − |
| 525 | 1 | H | H | OMe | Cl | H | | |
| 526 | 1 | H | H | $OCF_2$ | Cl | H | + | − |
| 527 | 1 | H | Me | H | Me | H | + | |
| 528 | 1 | H | Me | Cl | Me | H | + | |
| 529 | 1 | H | $CH_2OH$ | H | $CH_2OH$ | H | + | + |
| 530 | 1 | H | Cl | H | Cl | H | + | + |
| 531 | 1 | H | OMe | H | $CF_3$ | H | − | + |
| 532 | 1 | F | OMe | H | OMe | H | + | + |
| 533 | 1 | F | Me | Cl | Me | H | − | + |
| 534 | 1 | F | $CH_2OH$ | H | $CH_2OH$ | H | + | |
| 535 | 1 | F | Cl | H | Cl | H | + | + |
| 536 | 1 | F | OMe | H | $CF_3$ | H | + | + |
| 537 | 1 | F | Me | H | Me | H | + | + |
| 538 | 1 | F | Me | H | $CF_3$ | H | + | − |
| 539 | 1 | H | Cl | H | OMe | H | + | + |
| 540 | 0 | H | OMe | H | OMe | H | | |
| 541 | 0 | H | OMe | H | $CF_3$ | H | + | + |
| 542 | 0 | H | Me | H | $CF_3$ | H | − | − |
| 543 | 0 | H | Cl | H | Cl | H | + | + |
| 544 | 0 | H | Me | H | Me | H | − | − |
| 545 | 0 | H | H | H |  | Me | | |
| 546 | 1 | H | OMe | H | OMe | Me | + | − |
| 547 | 1 | H | Me | H | Me | Me | + | + |
| 548 | 1 | H | H | H |  | Me | | |
| 549 | 1 | H | H | H |  | Me | + | + |
| 550 | 1 | H | H | H |  | H | + | + |
| 551 | 1 | H | H | H | H | H | + | + |
| 552 | 1 | F | H | H |  | H | + | + |
| 553 | 1 | F | H |  | H | H | + | + |

TABLE 5-continued

| No. | m | R⁷ | R²¹ | R²² | R²³ | R⁴' | A549 | H1299 |
|---|---|---|---|---|---|---|---|---|
| 554 | 1 | H | H | C(O)NHMe | Cl | H | + | + |
| 555 | 1 | H | H | C(O)NHMe | Cl | Me | | |
| 556 | 1 | H | H | S(O)₂NHMe | OMe | H | | |
| 557 | 1 | H | H | H | 1,2,4-oxadiazol-3-yl | H | | |
| 558 | 1 | H | C(O)OMe | H | oxazol-2-yl | H | + | + |
| 559 | 1 | H | CF₃ | H | oxazol-2-yl | H | + | + |
| 560 | 0 | F | OMe | OMe | OMe | H | + | + |
| 561 | 0 | F | OMe | H | OMe | H | + | + |
| 562 | 0 | F | Me | H | Me | H | + | + |
| 563 | 0 | F | Cl | OH | Cl | H | + | + |
| 564 | 0 | F | Cl | H | Cl | H | + | + |
| 565 | 0 | F | Me | Cl | Me | H | − | − |
| 566 | 0 | F | Me | OH | Cl | H | + | + |
| 567 | 0 | F | OMe | H | CF₃ | H | + | + |
| 568 | 0 | F | Me | H | CF₃ | H | − | + |
| 569 | 1 | H | Me | -OCH₂C(O)NHMe | Me | H | + | + |
| 570 | 0 | H | Me | -OCH₂C(O)NHMe | Me | H | + | + |
| 571 | 1 | F | H | H | oxazol-2-yl | H | + | + |
| 572 | 1 | F | H | H | oxazol-2-yl | Me | + | + |
| 573 | 1 | H | Me | -OCH₂C(O)NHMe | Me | Me | + | + |
| 574 | 1 | F | Me | -OCH₂C(O)NHMe | Me | Me | + | + |

TABLE 5-continued
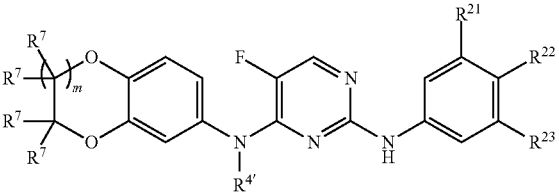
| No. | m | R⁷ | R²¹ | R²² | R²³ | R⁴' | A549 | H1299 |
|---|---|---|---|---|---|---|---|---|
| 575 | 1 | F | Me | 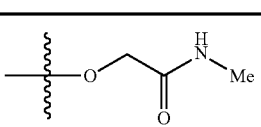 | Me | H | + | + |
| 576 | 1 | H | H | H | 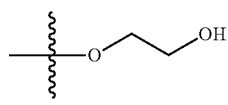 [SMILES: *OCCO] | H | + | |
| 577 | 2 | H | H | 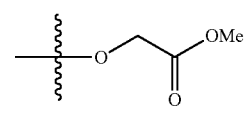 [SMILES: *OCC(=O)OC] | H | H | | |
| 578 | 2 | H | H | 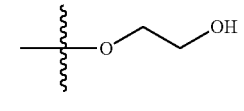 [SMILES: *OCCO] | H | H | | |
| 579 | 2 | H | H | 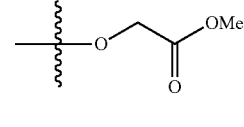 [SMILES: *OCC(=O)OC] | H | H | | |
| 580 | 2 | H | H | H | 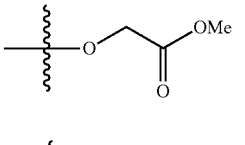 | H | − | |
| 581 | 2 | H | H | H | 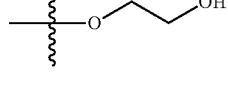 | H | + | |
| 582 | 2 | H | H | H | 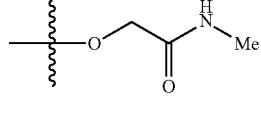 | H | | |
| 583 | 1 | H | Me | OH | Cl | H | | |
| 584 | 1 | H | Me | OMe | Me | H | | |
| 585 | 1 | H | Me | OMe | Cl | H | | |
| 586 | 1 | H | H | H | 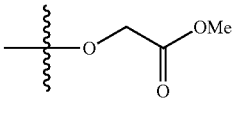 | H | − | |
| 587 | 1 | H | H | 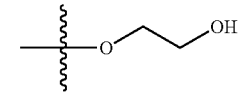 [SMILES: *OCCO] | H | H | + | |

TABLE 6
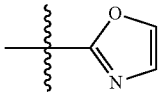 [SMILES: *c1ncco1]
| No. | Y¹ | Y² | Z³ | R¹⁷ | R¹⁸ | R¹⁹ | R²⁰ | R²¹ | R²² | R²³ | R⁴' | A549 | H1299 |
|---|---|---|---|---|---|---|---|---|---|---|---|---|---|
| 588 | N | O | CH | Me | Me | H | H | OMe | H | OMe | H | + | + |
| 589 | N | O | CH | H | H | H | H | H | H | 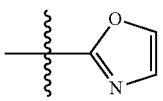 [SMILES: *c1ncco1] | H | + | + |
| 590 | N | O | CH | Me | Me | H | H | H | H | 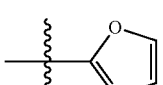 | H | + | + |
| 591 | N | O | CH | H | H | H | H | H | H | 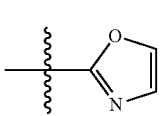 | H | + | + |
| 592 | N | O | CH | Me | Me | H | H | H | H | 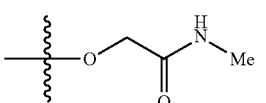 | H | — | — |
| 593 | N | O | CH | H | H | H | CH₂CH₂OH | OMe | H | OMe | H | | |
| 594 | N | O | CH | H | H | H | CH₂CH₂OH | Me | H | Me | H | | |
| 595 | N | S | CH | H | H | H | H | H | H | 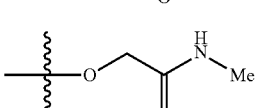 | H | | |
| 596 | N | O | CH | H | H | Me | Me | H | H | 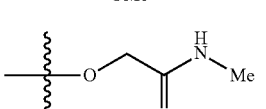 | H | | |
| 597 | N | O | CH | H | H | Me | Me | Me | OMe | Cl | H | + | + |
| 598 | N | O | CH | H | H | Me | Me | OMe | H | OMe | H | | |
| 599 | N | O | N | H | H | Me | Me | H | H | 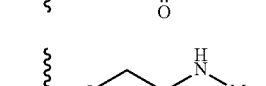 | H | | |
| 600 | N | O | N | H | H | H | H | H | H | 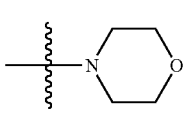 | H | | |
| 601 | N | O | N | H | H | H | H | 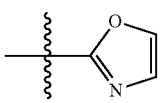 [SMILES: *c1ncco1] | H | H | H | | |
| 602 | N | O | N | H | H | H | H | H | H | 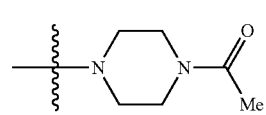 | H | | |
| 603 | N | O | N | H | H | H | H | H | H |  | H | + | + |

TABLE 6-continued

| No. | Y¹ | Y² | Z³ | R¹⁷ | R¹⁸ | R¹⁹ | R²⁰ | R²¹ | R²² | R²³ | R⁴' | A549 | H1299 |
|---|---|---|---|---|---|---|---|---|---|---|---|---|---|
| 604 | N | O | N | H | H | H | H | H | 4-(ethoxycarbonyl)piperazin-1-yl | H | H | − | + |
| 605 | N | O | N | H | H | H | H | H | H | morpholin-4-yl | H | + | + |
| 606 | N | O | N | H | H | H | H | H | H | 4-acetylpiperazin-1-yl | H | + | + |
| 607 | N | O | N | H | H | H | H | H | H | 4-(ethoxycarbonyl)piperazin-1-yl | H | + | + |
| 608 | N | O | N | H | H | H | H | H | 4-methylpiperazin-1-yl | H | H | + | + |
| 609 | N | O | N | H | H | H | H | H | H | 4-methylpiperazin-1-yl | H | + | + |
| 610 | N | O | N | H | H | H | H | H | H | oxazol-2-yl | H | + | + |
| 611 | N | O | N | H | H | H | H | OMe | OMe | OMe | H | + | + |
| 612 | N | O | N | H | H | H | H | H | OMe | Cl | H | − | − |
| 613 | N | O | N | H | H | H | H | H | H | 4-methylpiperazin-1-yl | H | + | + |
| 614 | N | O | N | H | H | H | H | H | H | 4-methylpiperazin-1-yl | H | + | + |
| 615 | N | O | N | H | H | H | H | H | 4-methylpiperazin-1-yl | Cl | H | + | + |
| 616 | N | O | N | H | H | H | H | H | 4-methylpiperazin-1-yl | Me | H | + | + |

TABLE 7

| No. | Type | R4' | R4 | Y | R11 | A549 | HTC116 | H1299 |
|-----|------|-----|-----|---|-----|------|--------|-------|
| 617 | A | H | 4-tert-butylphenyl | NH | OEt | − | | |
| 618 | A | H | 2,3-dihydro-1,4-benzodioxin-6-yl | NH | OEt | + | | |
| 619 | A | H | 4-tert-butylphenyl | O | OMe | − | | |
| 620 | A | H | 3-hydroxyphenyl | O | OMe | | | |
| 621 | A | H | 3-hydroxyphenyl | NH | OH | − | | |
| 622 | A | H | 4-tert-butylphenyl | O | OH | − | | |
| 623 | A | H | 3-isopropoxyphenyl | O | OMe | − | | |
| 624 | A | H | 3-hydroxyphenyl | O | morpholino | − | | |
| 625 | A | H | 3-isopropoxyphenyl | O | morpholino | + | + | |

TABLE 7-continued

| No. | Type | R4' | R4 | Y | R11 | A549 | HTC116 | H1299 |
|---|---|---|---|---|---|---|---|---|
| 626 | A | H | 2,3-dihydrobenzo[1,4]dioxin-6-yl | O | morpholino | −/+ | + | |
| 627 | A | H | 3-hydroxyphenyl | O | NHMe | − | | |
| 628 | A | H | 4-tert-butylphenyl | O | NHMe | − | | |
| 629 | A | H | 2,3-dihydrobenzo[1,4]dioxin-6-yl | O | NHMe | + | + | |
| 630 | A | H | 3-hydroxyphenyl | O | NH(CH2)2OH | − | | |
| 631 | A | H | 2,3-dihydrobenzo[1,4]dioxin-6-yl | O | NH(CH2)2OH | + | + | |
| 632 | A | H | 2,3-dihydrobenzo[1,4]dioxin-6-yl | O | piperazin-1-yl | + | + | |
| 633 | A | H | 3-hydroxyphenyl | O | piperazin-1-yl | + | + | |
| 634 | A | H | 2,3-dihydrobenzo[1,4]dioxin-6-yl | O | piperazin-1-yl | + | − | |

TABLE 7-continued

| No. | Type | R⁴' | R⁴ | Y | R¹¹ | A549 | HTC116 | H1299 |
|---|---|---|---|---|---|---|---|---|
| 635 | A | H | 3-HO-phenyl | O | piperazin-1-yl | + | | |
| 636 | A | H | 3-HO-phenyl | O | OMe | + | − | |
| 637 | A | H | 3-HO-phenyl | NH | OEt | | | |
| 638 | A | H | 2,3-dihydrobenzo[1,4]dioxin-6-yl | O | OMe | − | | |
| 639 | A | H | 2,3-dihydrobenzo[1,4]dioxin-6-yl | O | OH | − | | |
| 640 | A | H | 4-isopropoxyphenyl | O | pyrrolidin-1-yl | − | | |
| 641 | A | H | 4-isopropoxyphenyl | O | OMe | − | | |
| 642 | A | H | 4-tert-butylphenyl | O | NHMe | + | | |
| 643 | A | H | 3-HO-phenyl | O | N(Me)₂ | − | | |

TABLE 7-continued

| No. | Type | R⁴' | R⁴ | Y | R¹¹ | A549 | HTC116 | H1299 |
|---|---|---|---|---|---|---|---|---|
| 644 | A | H | 2,3-dihydrobenzo[1,4]dioxin-6-yl | O | homopiperazin-1-yl | + | + | |
| 645 | A | H | 2,3-dihydrobenzo[1,4]dioxin-6-yl | O | homopiperazin-1-yl | + | + | |
| 646 | B | H | 3,5-dimethylphenyl | NH | OEt | + | + | + |
| 647 | B | H | 2,3-dihydrobenzo[1,4]dioxin-6-yl | NH | OEt | + | + | |
| 648 | B | H | 3-hydroxyphenyl | NH | OEt | + | + | |
| 649 | B | H | 2,3-dihydrobenzo[1,4]dioxin-6-yl | NH | NHMe | + | + | |
| 650 | A | H | 3-chloro-4-methoxyphenyl | O | OMe | | | |
| 651 | A | H | 4-chlorophenyl | O | OMe | − | | |

TABLE 7-continued

Type A, Type B structures (as shown)

| No. | Type | R4' | R4 | Y | R11 | A549 | HTC116 | H1299 |
|---|---|---|---|---|---|---|---|---|
| 652 | A | H | 3,4-dichlorophenyl | O | OMe | | − | |
| 653 | B | H | 2,2,3,3-tetrafluoro-1,4-benzodioxin-6-yl | NH | NHMe | + | | + |
| 654 | B | H | 3,5-dimethoxyphenyl | NH | NHMe | + | | + |
| 655 | B | H | 1,3-benzodioxol-5-yl | NH | NHMe | + | | + |
| 656 | A | H | 3,5-dimethoxyphenyl | O | OMe | − | | − |
| 657 | A | H | 3,5-dimethoxyphenyl | O | OH | − | | − |
| 658 | A | H | 3,5-dimethoxyphenyl | NH | Me | − | | + |

TABLE 7-continued

| No. | Type | R⁴' | R⁴ | Y | R¹¹ | A549 | HTC116 | H1299 |
|---|---|---|---|---|---|---|---|---|
| 659 | B | H | 3,5-diOMe-phenyl | NH | N(Me)CH₂CH₂OH | + | + | + |
| 660 | B | H | 3,5-diOMe-phenyl | NH | NHC(Me)₂CH₂OH | + | + | + |
| 661 | B | Me | (structure shown) | O | OMe | − | | − |
| 662 | A | Me | 3,5-diOMe-phenyl | O | OMe | − | | + |
| 663 | B | Me | 3,5-diOMe-phenyl | NH | NHMe | + | | + |
| 664 | B | H | 3,4-diOMe-phenyl | NH | OEt | + | | + |
| 665 | B | H | 3,4-diOMe-phenyl | NH | NHMe | + | | + |

TABLE 7-continued

| | | | | Type A | | | | Type B | |
|---|---|---|---|---|---|---|---|---|---|

| No. | Type | R⁴' | R⁴ | Y | R¹¹ | A549 | HTC116 | H1299 |
|---|---|---|---|---|---|---|---|---|
| 666 | B | Me | 3,4-dimethoxyphenyl | NH | OEt | | + | + |
| 667 | B | H | CH₂CH₂OH | NH | OEt | − | − | − |
| 668 | B | H | 3,5-dimethylphenyl | NH | NHMe | | − | + |
| 669 | B | H | 3-CF₃-5-MeO-phenyl | NH | NHMe | | + | + |
| 670 | B | H | 2,2-difluoro-1,3-benzodioxol-5-yl | NH | NHMe | − | | − |
| 671 | A | Me | 3-Cl-4-MeO-phenyl | O | OMe | − | | − |
| 672 | A | Me | 4-Cl-3,5-dimethylphenyl | O | OMe | − | | − |
| 673 | A | H | 3-tert-butylphenyl | O | OMe | | | |

TABLE 7-continued

| No. | Type | R⁴' | R⁴ | Y | R¹¹ | A549 | HTC116 | H1299 |
|---|---|---|---|---|---|---|---|---|
| 674 | A | H | 3-isopropoxyphenyl | O | OMe | | | |
| 675 | A | H | 3-tert-butylphenyl | O | NHMe | – | | |
| 676 | A | H | 2,2-difluoro-3-oxo-3,4-dihydro-2H-benzo[b][1,4]oxazin-6-yl | O | OMe | + | | |
| 677 | A | H | 2,2-dimethyl-3-oxo-3,4-dihydro-2H-benzo[b][1,4]oxazin-6-yl | O | OMe | + | – | |
| 678 | B | H | cyclobutylmethyl | NH | OEt | – | – | |

TABLE 8
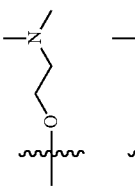
| No. | R⁴' | R²¹ | R²² | R²³ | R³¹ | R³² | R³³ | A549 | H1299 |
|---|---|---|---|---|---|---|---|---|---|
| 679 | H | Cl | H | H | Cl | H | H | | |
| 680 | H | Me | Me | H | Me | Me | H | | |
| 681 | H | H | H | Br | H | H | Br | | |
| 682 | H | Cl | H | H | Cl | H | H | | |
| 683 | H | Me | Me | H | Me | Me | H | | |
| 684 | H | H | Cl | H | H | Cl | H | | |
| 685 | H | H | OEt | H | H | OEt | H | | |
| 686 | H | H | OMe | H | H | OMe | H | | |
| 687 | H | Me | H | H | Me | H | H | | |
| 688 | H | H | Br | H | H | Br | H | | |
| 689 | H | H | H | Br | H | H | Br | | |
| 690 | H | H | H | H | H | H | H | | |
| 691 | H | H | H | H | H | H | H | | |
| 692 | H | Me | H | H | Me | H | H | | |
| 693 | H | H | 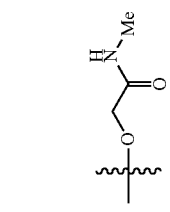 | H | H | H | OH | | |
| 694 | H | H |  | H | H | H | 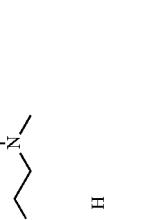 | + | + |
| 695 | H | H | H | 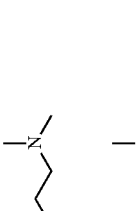 | H | F | F | + | |
| 696 | H | H | H | 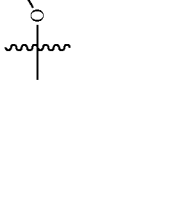 | H | Cl | H | + | |
| 697 | H | H | H |  | H | Cl | Cl | + | + |

TABLE 8-continued

| No. | R⁴' | R²¹ | R²² | R²³ | R³¹ | R³² | R³³ | A549 | H1299 |
|---|---|---|---|---|---|---|---|---|---|
| 698 | H | H | H | —O-CH₂-C(=O)-NHMe | H | H | OCF₃ | + | |
| 699 | H | H | H | —O-CH₂-C(=O)-NHMe | H | OCF₃ | Cl | | |
| 700 | H | H | H | Me | H | OCF₃ | Cl | − | |
| 701 | H | H | CF₃ | H | H | CF₃ | H | + | |
| 702 | H | H | OMe | F | H | OMe | F | + | |
| 703 | H | H | CF₃ | H | H | CF₃ | H | − | |
| 704 | H | H | OEt | H | H | OEt | H | + | + |
| 705 | H | H | H | OCF₃ | H | H | OCF₃ | − | |
| 706 | H | H | Cl | CF₃ | H | Cl | CF₃ | + | + |
| 707 | H | H | H | OEt | H | H | OEt | − | |
| 708 | H | H | H | OMe | H | OEt | OMe | − | |
| 709 | H | H | OMe | OMe | H | H | H | + | |
| 710 | H | H | OMe | OH | H | OMe | OH | − | |
| 711 | H | H | OMe | OH | H | H | OH | + | + |
| 712 | H | H | OEt | H | H | OMe | OMe | − | |
| 713 | H | H | H | H | H | OEt | H | + | |
| 714 | H | H | H | OH | H | OMe | H | − | |
| 715 | H | H | Cl | H | H | Cl | H | + | − |
| 716 | H | H | Cl | Cl | H | H | Cl | − | − |
| 717 | H | H | H | H | H | H | Cl | + | − |
| 718 | H | H | t-butyl | H | H | t-butyl | H | − | − |
| 719 | H | H | F | H | H | F | H | + | − |
| 720 | H | H | F | H | H | F | H | − | |
| 721 | H | H | Me | H | H | Me | H | | |
| 722 | H | H | Et | H | H | Et | H | | |
| 723 | H | H | —O-CH₂-C(=O)-OMe | H | H | —O-CH₂-C(=O)-OMe | H | + | |

TABLE 8-continued

| No. | R4' | R21 | R22 | R23 | R31 | R32 | R33 | A549 | H1299 |
|---|---|---|---|---|---|---|---|---|---|
| 724 | H | H | H | —OCH₂C(=O)OMe | H | H | —OCH₂C(=O)OMe | − | + |
| 725 | H | H | OMe | OH | H | OMe | OH | + | |
| 726 | H | H | Me | OH | H | Me | OH | | |
| 727 | H | H | —OCH₂CH₂OMe | H | H | —OCH₂CH₂OMe | H | + | |
| 728 | H | H | —OCH₂CH₂OH | H | H | H | OH | − | |
| 729 | H | H | —OCH₂C(=O)OEt | H | H | H | OH | | |
| 730 | H | H | OH | H | H | OH | H | + | |
| 731 | H | H | OH | Me | H | OH | Me | − | |
| 732 | H | H | H | —OCH₂C(=O)NHMe | H | H | OH | + | |
| 733 | H | H | —OCH₂C(=O)OH | H | H | —OCH₂C(=O)OH | H | − | |
| 734 | H | H | —OCH₂C(=O)NHMe | H | H | —OCH₂C(=O)OH | H | − | |

TABLE 8-continued

| No. | R4' | R21 | R22 | R23 | R31 | R32 | R33 | A549 | H1299 |
|---|---|---|---|---|---|---|---|---|---|
| 735 | H | H | pyrrolidin-1-yl-C(O)-CH$_2$-O- | H | H | pyrrolidin-1-yl-C(O)-CH$_2$-O- | H | — | — |
| 736 | H | H | HOOC-CH$_2$-O- | H | H | H | Cl | — | — |
| 737 | H | H | EtO$_2$C-CH$_2$-O- | H | H | EtO$_2$C-CH$_2$-O- | H | — | — |
| 738 | H | H | MeO$_2$C-CH$_2$-O- | H | H | t-BuO$_2$C-CH$_2$-O- | H | — | — |
| 739 | H | H | t-BuO$_2$C-CH$_2$-O- | H | H | t-BuO$_2$C-CH$_2$-O- | H | — | — |
| 740 | H | H | OH | Cl | H | OH | Cl | — | — |
| 741 | H | H | EtO$_2$C-CH$_2$-O- | Cl | H | | Cl | — | — |
| 742 | H | H | OH | F | H | H | F | — | — |
| 743 | H | OMe | OMe | OMe | OMe | | OMe | | — |
| 744 | H | H | morpholin-4-yl-CH$_2$CH$_2$-O- | H | H | OH | H | + | — |
| 745 | H | H | i-propoxy | H | H | i-propoxy | H | — | — |

TABLE 8-continued

| No. | R⁴' | R²¹ | R²² | R²³ | R³¹ | R³² | R³³ | A549 | H1299 |
|---|---|---|---|---|---|---|---|---|---|
| 746 | H | H | H | OH | H | 2-morpholinoethoxy | H | – | |
| 747 | H | H | -OCH₂C(O)NHMe | H | H | t-Bu | H | – | |
| 748 | H | H | H | -OCH₂C(O)NHMe | H | t-Bu | H | – | |
| 749 | H | H | H | -OCH₂C(O)OH | H | t-Bu | H | – | |
| 750 | H | H | H | -OCH₂CH₂OH | H | t-Bu | H | – | |
| 751 | H | H | H | -OCH₂C(O)NHMe | H | i-propoxy | H | –/+ | |
| 752 | H | H | H | -OCH₂C(O)OH | H | i-propoxy | H | – | |
| 753 | H | H | H | -OCH₂C(O)NHMe | H | OMe | OMe | – | |

TABLE 8-continued
| No. | R⁴' | R²¹ | R²² | R²³ | R³¹ | R³² | R³³ | A549 | H1299 |
|---|---|---|---|---|---|---|---|---|---|
| 754 | H | H | H |  | H | OMe | OMe | − | |
| 755 | H | H | H |  | H | H | OMe | + | |
| 756 | H | H | H |  | H | Me | OH | | |
| 757 | H | H | Me |  | H | H | OH | | |
| 758 | H | H | Me |  | H | Me | OH | | |
| 759 | H | H | Me |  | H | Me |  | + | + |
| 760 | H | OMe | OMe | OMe | H | H | OH | + | − |
| 761 | H | H | H |  | H | H | OH | | |

TABLE 8-continued

Structure: A pyrimidine core with fluorine, bearing two arylamine groups. The top aniline has R21, R22, R23 substituents; the bottom aniline (N-R4') has R31, R32, R33 substituents.

| No. | R4' | R21 | R22 | R23 | R31 | R32 | R33 | A549 | H1299 |
|---|---|---|---|---|---|---|---|---|---|
| 762 | H | H | H | –O-CH$_2$-C(=O)-morpholine | H | H | OH | – | – |
| 763 | H | H | H | OH | H | H | –O-CH$_2$-C(=O)-OEt | – | + |
| 764 | H | H | i-pr | H | H | H | OH | – | + |
| 765 | H | OMe | H | –O-CH$_2$-C(=O)-OMe | H | H | OH | + | + |
| 766 | H | H | H | –O-CH$_2$-C(=O)-OMe | OMe | H | OMe | – | + |
| 767 | H | H | H | –O-CH$_2$-C(=O)-NHMe | OMe | H | OMe | – | – |
| 768 | H | H | H | OH | OMe | H | –O-CH$_2$-C(=O)-OEt | + | + |
| 769 | H | OMe | H | OMe | H | H | –O-CH$_2$-C(=O)-OEt | – | – |
| 770 | H | H | H | –O-CH$_2$-C(=O)-NHMe | H | H | CF$_3$ | + | + |
| 771 | H | OMe | H | OMe | H | H | –O-CH$_2$-C(=O)-NHMe | + | + |

TABLE 8-continued

| No. | R⁴' | R²¹ | R²² | R²³ | R³¹ | R³² | R³³ | A549 | H1299 |
|-----|-----|-----|-----|-----|-----|-----|-----|------|-------|
| 772 | H | H | H | ~O-CH₂-C(O)-NHMe | H | OEt | H | + | + |
| 773 | H | H | OMe | ~O-CH₂-C(O)-NHMe | H | H | OH | | |
| 774 | H | H | H | oxazole | H | H | OH | | |
| 775 | H | H | H | ~O-CH₂-C(O)-NHMe | H | H | Cl | | |
| 776 | H | H | H | ~O-CH₂-C(O)-NHMe | CF₃ | H | OMe | | |
| 777 | H | H | H | ~O-CH₂-C(O)-NHMe | H | OMe | OH | | |
| 778 | H | H | H | ~O-CH₂-C(O)-NHMe | H | OMe | CF₃ | | |
| 779 | H | H | H | ~O-CH₂-C(O)-NHMe | H | F | CF₃ | | |

TABLE 8-continued

| No. | R4' | R21 | R22 | R23 | R31 | R32 | R33 | A549 | H1299 |
|---|---|---|---|---|---|---|---|---|---|
| 780 | H | H | H | -O-CH$_2$-C(=O)-NHMe | H | Me | Cl | | |
| 781 | H | H | OCF$_3$ | -O-CH$_2$-C(=O)-NHMe (Cl) | H | H | OH | | |
| 782 | H | Br | H | -O-CH$_2$-C(=O)-NHMe (CF$_3$) | H | H | OH | + | + |
| 783 | H | H | H | -O-CH$_2$-C(=O)-NHMe | H | OCF$_3$ | H | | |
| 784 | H | H | H | -O-CH$_2$-C(=O)-NHMe | H | CF$_3$ | H | | |
| 785 | H | H | H | -O-CH$_2$-C(=O)-NHMe | H | Cl | CF$_3$ | | |
| 786 | H | H | H | -O-CH$_2$-C(=O)-NHMe (OH) | H | H | OCF$_3$ | | |
| 787 | H | Cl | OH | -O-CH$_2$-C(=O)-NHMe (Me) | H | H | OH | | |
| 788 | H | H | H | -O-CH$_2$-C(=O)-NHMe | H | OMe | Cl | + | |
| 789 | H | H | H | -O-CH$_2$-C(=O)-NHMe | H | OMe | F | | |
| 790 | H | H | H | -O-CH$_2$-C(=O)-NHMe | H | Me | OMe | + | |

TABLE 8-continued

[Structure: pyrimidine core with F, two aryl amine substituents bearing R21/R22/R23 and R31/R32/R33, and R4']

| No. | R4' | R21 | R22 | R23 | R31 | R32 | R33 | A549 | H1299 |
|---|---|---|---|---|---|---|---|---|---|
| 791 | H | H | H | -O-CH2-C(=O)-NHMe | H | H | | + | + |
| 792 | H | H | H | -O-CH2-C(=O)-NHMe | H | H | CF3 | + | + |
| 793 | H | H | H | -O-CH2-C(=O)-NHMe | H | Me | Me | | |
| 794 | H | H | H | -O-CH2-C(=O)-NHMe | H | F | OH | | |
| 795 | H | -O-CH2-C(=O)-OMe | H | OMe | H | H | OH | | |
| 796 | H | OH | H | OMe | H | H | OH | | |
| 797 | H | OH | H | -O-CH2-C(=O)-NHMe | H | H | OH | + | − |
| 798 | H | -O-CH2-C(=O)-NHMe | H | -O-CH2-C(=O)-NHMe | H | H | OH | − | − |
| 799 | H | H | H | OH | H | OMe | Cl | − | − |
| 800 | H | H | OMe | Cl | H | OMe | Cl | + | − |

TABLE 8-continued

| No. | R4' | R21 | R22 | R23 | R31 | R32 | R33 | A549 | H1299 |
|---|---|---|---|---|---|---|---|---|---|
| 801 | H | Me | OH | Cl | H | OMe | Cl | − | − |
| 802 | H | Me | OMe | Cl | H | OMe | Cl | | |
| 803 | H | H | H | -C(Me)₂-CH₂-O-C(O)-NH-Me | H | O-iPr | Cl | | |
| 804 | H | H | H | -C(Me)₂-CH₂-O-C(O)-NH-Me | Me | OMe | Cl | | |
| 805 | H | OMe | H | OMe | H | morpholino | Cl | | |
| 806 | H | CF₃ | H | OMe | H | morpholino | Cl | + | + |
| 807 | H | H | H | -C(Me)₂-CH₂-O-C(O)-NH-Me | H | OMe | Cl | | |
| 808 | H | Cl | H | Cl | H | OMe | Cl | + | + |
| 809 | H | Me | H | Me | H | OMe | Cl | + | − |
| 810 | H | CF₃ | Me | OMe | H | OMe | Cl | + | + |
| 811 | H | Me | H | Me | H | H | Cl | + | + |
| 812 | H | OMe | H | OMe | Me | H | OCF₃ | − | − |
| 813 | H | Me | H | Me | Me | H | OCF₃ | + | + |
| 814 | H | OMe | H | OMe | CF₃ | H | Me | + | + |
| 815 | H | OMe | H | CF₃ | CF₃ | H | Me | + | +/− |
| 816 | H | Me | H | CF₃ | CF₃ | H | OMe | +/− | + |
| 817 | H | Me | H | Me | CF₃ | H | OMe | + | + |
| 818 | H | OMe | H | OMe | CF₃ | H | OMe | + | + |
| 819 | H | CF₃ | H | OMe | CF₃ | H | OMe | +/− | + |
| 820 | H | Me | H | CF₃ | CF₃ | H | OMe | +/− | + |
| 821 | H | OMe | OMe | OMe | CF₃ | H | OMe | + | + |

TABLE 8-continued

| No. | R⁴' | R²¹ | R²² | R²³ | R³¹ | R³² | R³³ | A549 | H1299 |
|---|---|---|---|---|---|---|---|---|---|
| 822 | H | Me | OH | Cl | CF₃ | H | OMe | + | + |
| 823 | H | Cl | H | CH₂OH | CF₃ | H | OMe | + | + |
| 824 | H | CH₂OH | H | Me | CF₃ | H | OMe | + | -/+ |
| 825 | H | Me | Cl |  | CF₃ |  | OMe | + | + |
| 826 | H | H | H | -OCH₂C(O)NHMe | H | Cl |  |  |  |
| 827 | H | H | H | -OCH₂C(O)NHMe | H | -OCH₂C(O)NHMe | Cl |  |  |
| 828 | H | Cl | OH | Cl | H | OMe | Cl | + | + |
| 829 | H | Cl | OH | Cl | H | OCF₃ | Cl | + | + |
| 830 | H | H | H | -OCH₂C(O)NHMe | H | -OCH₂CH₂OH | Cl |  |  |
| 831 | H | Cl | OMe | Cl | H | OMe | Cl | - | - |
| 832 | H | Cl | OMe | Cl | H | OCF₃ | Cl | + | - |
| 833 | H | H | H | -OCH₂C(O)NHMe | Cl | OMe | Cl |  |  |
| 834 | H | Cl | OMe | Cl | H | Cl | Cl | + | + |
| 835 | H | OMe | H | OMe | H | Cl | Cl | + | + |
| 836 | H | OMe | H | OMe | H | OMe | Cl |  |  |
| 837 | H | Me | H | Me | H | OCF₃ | Cl | - | - |
| 838 | H | OMe | H | OMe | OMe | Cl | OMe | + | + |
| 839 | H | OMe | H | OMe | OMe | H | OMe | + | + |
| 840 | H | Me | H | Me | Me | H | Me |  |  |
| 841 | H | CH₂OH | H | CH₂OH | OMe | H | OMe | + | + |
| 842 | H | CH₂OH | H | CH₂OH | H | OMe | Cl | + | + |
| 843 | H | CH₂OH | H | CH₂OH | H | OMe | Cl | + | + |
| 844 | H |  | H |  | H | Cl | Cl | + | + |

TABLE 8-continued

| No. | R4' | R21 | R22 | R23 | R31 | R32 | R33 | A549 | H1299 |
|---|---|---|---|---|---|---|---|---|---|
| 845 | H | Me | Me | Me | OMe | H | OMe | + | + |
| 846 | H | Me | H | H | OMe | H | OMe | + | + |
| 847 | H | Cl | H | Cl | OMe | H | OMe | + |  |
| 848 | H | Me | H | CF$_3$ | OMe | H | OMe | + | + |
| 849 | H | OMe | H | CF$_3$ | OMe | H | OMe |  |  |
| 850 | Me | H | H | -CH$_2$-O-C(Me)$_2$-C(=O)-NHMe | OMe | H | OMe | − | − |
| 851 | Me | Me | H | Me | OMe | H | OMe | + | + |
| 852 | Me | OMe | H | OMe | OMe | H | OMe | + | + |
| 853 | Me | H | OMe | Cl | OMe | H | OMe | − | − |
| 854 | H | H | Cl | Me | OMe | H | OMe | − | − |
| 855 | H | Me | H | OMe | OMe | H | OMe | + | + |
| 856 | H | OMe | H |  | H | OMe | OMe | + | + |
| 857 | H | H | H | 5-oxazolyl-methyl | H | OMe | OMe | + | + |
| 858 | H | H | H | 2-oxazolyl-methyl | H | OMe | OMe | + | + |
| 859 | H | H | H | 2-oxazolyl-methyl | H | OMe | OMe | + | + |
| 860 | H | H | OMe | Cl | H | OMe | OMe | + |  |
| 861 | H | H | H | 4-acetyl-piperazin-1-yl-methyl | OMe | H | OMe | + | + |

TABLE 8-continued

| No. | R4' | R21 | R22 | R23 | R31 | R32 | R33 | A549 | H1299 |
|---|---|---|---|---|---|---|---|---|---|
| 862 | H | H | H | 4-acetylpiperazin-1-yl | H | OMe | OMe | + | + |
| 863 | H | H | H | H | H | OMe | OMe | + | ++ |
| 864 | Me | Me | H | Me | H | OMe | OMe | ++ | ++ |
| 865 | Me | OMe | H | OMe | H | OMe | OMe | + | + |
| 866 | H | H | H | H | OMe | H | OMe | + | + |
| 867 | Me | H | 4-acetylpiperazin-1-yl | H | H | OMe | OMe | – | + |
| 868 | Me | H | H | oxazol-5-yl | H | OMe | OMe | + | + |
| 869 | Me | H | H | oxazol-2-yl | H | OMe | OMe | + | + |
| 870 | Me | H | oxazol-2-yl | H | H | OMe | OMe | – | – |
| 871 | H | H | C(O)NHMe | Cl | H | OMe | OMe | ++ | ++ |
| 872 | H | H | C(O)NHMe | Cl | OMe | H | OMe | + | + |
| 873 | H | H | C(O)NHMe | Cl | H | OMe | Cl | | |
| 874 | Me | H | C(O)NHMe | Cl | H | H | OH | | |
| 875 | H | OMe | C(O)NHMe | OMe | H | OMe | OMe | + | + |
| 876 | H | Me | H | OMe | H | C(O)NHMe | Cl | | |
| 877 | H | | H | Me | H | C(O)NHMe | Cl | + | + |

Core structure: 5-fluoro-N2-(3,4,5-trisubstituted-phenyl)-N4-(3,4,5-trisubstituted-phenyl)-pyrimidine-2,4-diamine, where the N4-nitrogen bears the R4' substituent.

TABLE 8-continued

| No. | R⁴' | R²¹ | R²² | R²³ | R³¹ | R³² | R³³ | A549 | H1299 |
|---|---|---|---|---|---|---|---|---|---|
| 878 | H | H | H | morpholine-CH₂C(O)-O-C(CH₃)₂- | H | C(O)NHMe | Cl | | |
| 879 | H | H | S(O)₂NHMe | OMe | H | OMe | OMe | + | + |
| 880 | H | H | S(O)₂NHMe | OMe | OMe | H | OMe | + | + |
| 881 | H | H | S(O)₂NHMe | OMe | H | Cl | CF₃ | + | + |
| 882 | H | H | S(O)₂NHMe | OMe | H | OCF₃ | Cl | | + |
| 883 | H | H | S(O)₂NHMe | OMe | H | H | Cl | + | + |
| 884 | H | OMe | H | OMe | H | S(O)₂NHMe | OMe | + | + |
| 885 | H | H | H | oxazole | H | H | OH | + | + |
| 886 | H | H | H | isoxazole | H | OMe | OMe | + | + |
| 887 | H | C(O)OMe | H | oxazole | H | OMe | OMe | + | + |
| 888 | H | C(O)OMe | H | oxazole | H | H | OH | + | + |
| 889 | H | CF₃ | H | oxazole | H | OMe | OMe | + | + |
| 890 | H | H | H | oxadiazole | H | H | OH | + | + |

TABLE 8-continued

| No. | R4' | R21 | R22 | R23 | R31 | R32 | R33 | A549 | H1299 |
|---|---|---|---|---|---|---|---|---|---|
| 891 | H | C(=O)OMe | H | oxazol-2-yl | C(=O)OMe | H | oxazol-2-yl | − | |
| 892 | H | CF₃ | H | oxazol-2-yl | CF₃ | H | oxazol-2-yl | + | + |
| 893 | H | Cl | OH | Cl | Cl | OMe | Cl | + | |
| 894 | H | H | 4-methylpiperazin-1-yl | Me | H | 4-methylpiperazin-1-yl | Me | + | + |
| 895 | H | OMe | OMe | OMe | Me | H | Me | + | + |
| 896 | H | Me | Cl | Cl | Me | H | Me | + | + |
| 897 | H | CH₂OH | H | CH₂OH | Me | H | Me | + | + |
| 898 | H | Cl | H | Cl | Me | H | Me | − | − |
| 899 | H | Cl | Cl | Cl | Me | H | Me | + | + |
| 900 | H | Me | Cl | Me | Me | H | Me | − | − |
| 901 | H | Me | OCH₂C(=O)NHMe | Me | H | OMe | Cl | + | + |
| 902 | H | Me | OCH₂C(=O)NHMe | Me | OMe | H | OMe | | + |
| 903 | Me | OMe | H | OMe | H | OMe | Cl | + | + |
| 904 | Me | OMe | OMe | Cl | H | OMe | Cl | − | − |
| 905 | Me | Me | OCH₂C(=O)NHMe | Me | H | OMe | Cl | + | + |

TABLE 8-continued
| No. | R⁴' | R²¹ | R²² | R²³ | R³¹ | R³² | R³³ | A549 | H1299 |
|---|---|---|---|---|---|---|---|---|---|
| 906 | Me | H | H |  | H | OMe | Cl | + | + |
| 907 | Me | H | Me | H | H | OMe | Cl | − | + |
| 908 | Me | OMe | H | OMe | H | Cl | OMe | + | + |
| 909 | Me | Me | H | Me | H | Cl | OMe | + | + |
| 910 | Me | H | H |  | H | Cl | OMe | + | − |
| 911 | Me | OMe | H | OMe | Me | Cl | Me | − | − |
| 912 | Me | Me | H | Me | Me | Cl | Me | + | + |
| 913 | Me | H | H |  | Me | Cl | Me | | |
| 914 | Me | H | H |  | Me | Cl | Me | − | − |
| 915 | H | Me | H | Me | H |  | Cl | | |
| 916 | H | OMe | H | OMe | H |  | Cl | | |
| 917 | H | H | OMe | Cl | H |  | Cl | + | + |

TABLE 8-continued

| No. | R4' | R21 | R22 | R23 | R31 | R32 | R33 | A549 | H1299 |
|---|---|---|---|---|---|---|---|---|---|
| 918 | H | Me | Cl | Me | H | OCH₂C(O)NHMe | Cl | | |
| 919 | H | H | C(O)NHMe | Cl | H | Cl | OMe | | |
| 920 | H | H | C(O)NHMe | Cl | H | Cl | CF3 | + | + |
| 921 | Me | H | C(O)NHMe | Cl | Me | Cl | Me | | |
| 922 | H | Me | H | Me | H | OCH₂C(O)OMe | Cl | | |
| 923 | H | OMe | H | OMe | H | OCH₂C(O)OMe | Cl | | |
| 924 | H | H | OMe | Cl | H | OCH₂C(O)OMe | Cl | | |
| 925 | H | Me | Cl | Me | H | OCH₂C(O)OMe | Cl | | |
| 926 | H | Me | H | Me | H | OCH₂CH₂OH | Cl | | |
| 927 | H | OMe | H | OMe | H | OCH₂CH₂OH | Cl | | |
| 928 | H | OMe | Cl | H | H | OCH₂CH₂OH | Cl | | |

TABLE 8-continued

| No. | R⁴' | R²¹ | R²² | R²³ | R³¹ | R³² | R³³ | A549 | H1299 |
|---|---|---|---|---|---|---|---|---|---|
| 929 | H | Me | Cl | Me | H | ⟿OCH₂CH₂OH | Cl | + | + |
| 930 | H | H | Cl | OMe | H | ⟿OCH₂CH₂OH | Cl | + | + |
| 931 | H | Me | ⟿OCH₂C(O)NHMe | Me | OMe | H | OMe | + | + |
| 932 | H | H | H | ⟿(oxazole)-OMe | OMe | OMe | OMe | + |  |
| 933 | H | H | H | ⟿OCH₂CH₂OMe | OH | OH | ⟿OCH₂CH₂OMe | + |  |
| 934 | H | H | ⟿OCH₂CH₂OH | H | H | H | OH | − |  |
| 935 | H | H | ⟿OCH₂C(O)OMe | H | H | i-pr | H | − |  |
| 936 | H | H | ⟿OCH₂CH₂OH | H | H | i-pr | H | + |  |
| 937 | H | H | F | Cl | H | i-pr | H | + |  |
| 938 | H | H | F | Cl | H | F | Cl | − |  |

TABLE 8-continued

| No. | R[4'] | R[21] | R[22] | R[23] | R[31] | R[32] | R[33] | A549 | H1299 |
|---|---|---|---|---|---|---|---|---|---|
| 939 | H | H | H | OH | H | H | 2-hydroxyethoxy | − | + |
| 940 | H | H | H | 2-hydroxyethoxy | OMe | H | OMe | + | + |
| 941 | H | Cl | OH | Cl | Cl | OH | Cl | − | + |
| 942 | H | Me | OH | Cl | Me | H | Cl | + | + |
| 943 | H | Cl | OH | Me | H | H | OH | + | + |
| 944 | H | H | H | OH | Cl | OH | Me | | |
| 945 | H | H | OMe | OMe | H | 3-morpholinopropoxy | Me | + | + |
| 946 | H | Me | OH | Cl | H | OH | H | − | + |
| 947 | H | H | H | ethoxycarbonylmethoxy | Me | OH | Me | − | |
| 948 | H | H | H | (morpholin-4-yl)carbonylmethoxy | Me | OH | Me | − | |
| 949 | H | H | H | 2-morpholinoethoxy | Me | OH | Me | + | + |
| 950 | H | H | H | 2-morpholinoethoxy | Me | OH | Me | + | + |
| 951 | H | H | H | t-Bu | H | H | OH | − | |

TABLE 8-continued

| No. | R⁴' | R²¹ | R²² | R²³ | R³¹ | R³² | R³³ | A549 | H1299 |
|---|---|---|---|---|---|---|---|---|---|
| 952 | H | H | H | -O-CH₂-C(=O)-OEt | Cl | OH | Me | − | + |
| 953 | H | H | H | t-Bu | H | OMe | OMe | − | − |
| 954 | H | H | H | -O-CH₂-C(=O)-morpholine | Cl | OH | Me | − | − |
| 955 | H | H | H | t-Bu | H | H | -O-CH₂-C(=O)-OEt | − | − |
| 956 | H | H | H | t-Bu | H | H | -O-CH₂-C(=O)-NHMe | − | − |
| 957 | H | H | H | -CH₂CH₂-morpholine | Cl | OH | Me | + | + |
| 958 | H | H | H | -O-CH₂-C(=O)-OEt | H | H | t-Bu | − | − |
| 959 | H | Me | OH | Cl | H | H | t-Bu | − | − |
| 960 | H | H | H | -O-CH₂-C(=O)-NHMe | H | H | t-Bu | − | − |

TABLE 8-continued

| No. | R4' | R21 | R22 | R23 | R31 | R32 | R33 | A549 | H1299 |
|---|---|---|---|---|---|---|---|---|---|
| 961 | H | H | H | -CH2-O-) | H | H | t-Bu | −/+ | |
| 962 | H | H | H | | H | H | t-Bu | − | − |
| 963 | H | H | H | | H | H | t-Bu | − | − |
| 964 | H | H | H | -CH2-O-, OEt) | H | H | i-pr | − | − |
| 965 | H | H | H | | H | H | i-pr | − | − |
| 966 | H | H | H | | H | H | i-pr | + | + |
| 967 | H | H | H | | H | CH2OH | CH2OH | − | |
| 968 | H | H | H | ![](i-pr, OMe) | H | H | i-pr | − | + |
| 969 | H | H | OMe | | H | H | OH | + | + |
| 970 | H | H | H | -CH2-O-) | H | H | CH2NH2 | + | + |

TABLE 8-continued

| No. | R⁴' | R²¹ | R²² | R²³ | R³¹ | R³² | R³³ | A549 | H1299 |
|---|---|---|---|---|---|---|---|---|---|
| 971 | H | H | -OCH₂C(O)NH₂ | H | H | -OCH₂C(O)NH₂ | H | − | |
| 972 | H | H | -OCH₂C(O)OMe | H | H | -OCH₂C(O)NH₂ | H | − | |
| 973 | H | H | -OCH₂C(O)NH₂ | H | H | -OCH₂C(O)OMe | H | + | + |
| 974 | H | H | -OCH₂C(O)NH₂ | OH | H | -OCH₂C(O)NH₂ | H | + | |
| 975 | H | H | H | H | H | H | OH | − | |
| 976 | H | H | H | -OCH₂C(O)OMe | H | H | OH | − | |
| 977 | H | H | H | -OCH₂C(O)OMe | H | i-propoxy | H | | |
| 978 | H | H | H | -OCH₂C(O)OH | H | H | OH | − | |

TABLE 8-continued
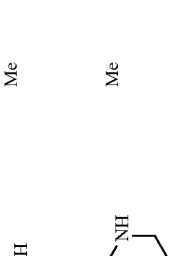
| No. | R⁴' | R²¹ | R²² | R²³ | R³¹ | R³² | R³³ | A549 | H1299 |
|---|---|---|---|---|---|---|---|---|---|
| 979 | H | H | H | | Me | OH | Me | − | + |
| 980 | H | H | H | piperazine-C(O)-CH2-O- | Me | OH | Me | + | |
| 981 | H | H | H | morpholine-CH2CH2-O- | Me | OH | Me | + | |
| 982 | H | H | H | MeOOC-CH2-O- | Me | OH | Me | − | |
| 983 | H | H | H | piperazine-C(O)-CH2-O- | Cl | OH | Me | + | |
| 984 | H | H | H | piperazine-CH2CH2-O- | Cl | OH | Me | + | |
| 985 | H | H | H | MeOOC-CH2-O- | Me | OMe | Me | − | |
| 986 | H | H | H | piperazine-C(O)-CH2-O- | Me | OMe | Me | − | |

TABLE 8-continued

| No. | R4' | R21 | R22 | R23 | R31 | R32 | R33 | A549 | H1299 |
|---|---|---|---|---|---|---|---|---|---|
| 987 | H | H | H | piperazinyl-ethoxy-methyl | Me | OMe | Me | − | + |
| 988 | H | H | H | cyclopropylaminocarbonyl-methoxy-methyl | H | morpholino-methyl | H | + | + |
| 989 | H | H | H | methoxycarbonyl-methoxy-methyl | H | morpholino-methyl | H | + | + |
| 990 | H | H | H | cyclobutylaminocarbonyl-methoxy-methyl | H | morpholino-methyl | H | + | + |
| 991 | H | H | H | N-methylaminocarbonyl-methoxy-methyl | Me | OH | Cl | + | − |
| 992 | H | H | H | N-methylaminocarbonyl-methoxy-methyl | H | morpholino-methyl | H | − | − |
| 993 | H | H | H | N-methylaminocarbonyl-methoxy-methyl | H | 4-(methoxycarbonyl)piperazin-1-yl-methyl | H | + | + |
| 994 | H | H | H | N-methylaminocarbonyl-methoxy-methyl | H | H | N-methylaminocarbonyl-methoxy-methyl | | |

TABLE 8-continued

| No. | R⁴' | R²¹ | R²² | R²³ | R³¹ | R³² | R³³ | A549 | H1299 |
|---|---|---|---|---|---|---|---|---|---|
| 995 | H | H | H | oxazol-2-yl | H | H | oxazol-2-yl | + | + |
| 996 | H | H | OH | CF₃ | H | OH | CF₃ | −/+ | |
| 997 | H | H | H | Me | H | H | Me | + | |
| 998 | H | H | Me | H | H | Me | H | − | |
| 999 | H | H | H | CH₂C(O)OEt | Cl | OH | Cl | − | − |
| 1000 | H | H | H | CH₂C(O)-morpholinyl | Cl | OH | Cl | − | |
| 1001 | H | H | H | CH₂C(O)-piperazinyl | Cl | OH | Cl | − | |
| 1002 | H | H | H | CH₂C(O)NHMe | H | CH₂C(O)OMe | H | − | |
| 1003 | H | H | H | CH₂C(O)NHMe | H | CH₂C(O)OEt | H | − | |
| 1004 | H | H | H | CH₂CH₂C(O)OEt | H | OH | H | − | |

TABLE 8-continued

| No. | R4' | R21 | R22 | R23 | R31 | R32 | R33 | A549 | H1299 |
|---|---|---|---|---|---|---|---|---|---|
| 1005 | H | H | H | [–OCH$_2$C(O)NHMe structure] | H | OMe | CH$_2$OH | | |
| 1006 | H | H | H | [–OCH$_2$C(O)NHMe structure] | H | Cl | Cl | + | + |
| 1007 | Me | Me | H | Me | H | Cl | Cl | | |
| 1008 | Me | H | OMe | Cl | H | Cl | Cl | | |
| 1009 | Me | OMe | H | OMe | H | Cl | Cl | | |
| 1010 | Me | Cl | OMe | Cl | H | Cl | Cl | − | − |
| 1011 | H | H | OCF$_3$ | Cl | H | Cl | Cl | − | − |
| 1012 | H | H | CH$_2$NHBoc | H | H | CH$_2$NHBoc | H | + | + |
| 1013 | H | H | CH$_2$NH$_2$ | H | H | CH$_2$NH$_2$ | H | + | + |
| 1014 | H | H | [–OCH$_2$C(O)NHMe structure] | H | H | Cl | Cl | | |
| 1015 | H | H | H | CH$_2$NHBoc | H | H | CH$_2$NHBoc | + | + |
| 1016 | H | H | H | CH$_2$NHBoc | H | H | CH$_2$NHBoc | + | + |
| 1017 | H | H | H | CH$_2$NHBoc | H | Cl | Cl | | |
| 1018 | H | H | H | CH$_2$NHBoc | H | Cl | Cl | | |
| 1019 | H | H | [–OCH$_2$C(O)NHMe structure] | H | H | Cl | Cl | | |
| 1020 | Me | H | [–NHC(O)CH$_2$NHMe structure] | H | H | Cl | Cl | | |

TABLE 8-continued

| No. | R4' | R21 | R22 | R23 | R31 | R32 | R33 | A549 | H1299 |
|---|---|---|---|---|---|---|---|---|---|
| 1021 | H | H | ![amide-CH2-NHEt group] | H | H | OMe | Cl | + | + |
| 1022 | H | H | C(O)NH$_2$ | H | H | OMe | Cl | + | + |
| 1023 | H | H | CH$_2$NHBoc | H | H | OMe | Cl | + | + |
| 1024 | H | H | CH$_2$NHBoc | H | H | OMe | Cl | + | + |
| 1025 | H | H | ![amide-CH2-O-NHMe group] | H | H | OMe | Cl | − | + |
| 1026 | H | H | H | OH | H | C(O)NH$_2$ | H | − | + |
| 1027 | H | Cl | OH | Cl | H | C(O)NH$_2$ | H | + | + |
| 1028 | H | H | OMe | Cl | H | C(O)NH$_2$ | H | + | + |
| 1029 | H | H | C(O)NH$_2$ | H | H | C(O)NH$_2$ | H | − | − |
| 1030 | Me | H | C(O)NH$_2$ | H | H | Cl | Cl | + | + |
| 1031 | Me | H | ![amide-CH2-NHEt group] | H | H | Cl | Cl | + | + |
| 1032 | H | H | C(O)NH$_2$ | H | H | Cl | OMe | − | − |
| 1033 | H | H | C(O)NH$_2$ | Cl | H | OMe | Cl | + | + |
| 1034 | H | H | C(O)NH$_2$ | Cl | H | Cl | OMe | − | + |
| 1035 | H | H | ![amide-CH2-NHEt group] | H | H | Cl | OMe | + | + |
| 1036 | H | H | C(O)NH$_2$ | H | H | H | H | + | + |

TABLE 9
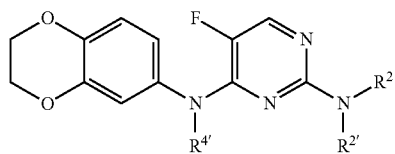
| No. | R⁴' | R²' | R² | A549 | H1299 |
| --- | --- | --- | --- | --- | --- |
| 1037 | H | H | CH₂CH=CH₂ | − | |
| 1038 | Me | H | Me | + | + |
| 1039 | Me | Me | Me | + | + |
| 1040 | Me | H | CH₂CH₂OH | + | + |
| 1041 | Me | H | i-propyl | + | + |
| 1042 | Me | CH₂CH₂OH | CH₂CH₂OH | − | + |
| 1043 | Me | H | CH₂CH=CH₂ | + | + |
| 1044 | H | H | Me | − | − |
TABLE 10
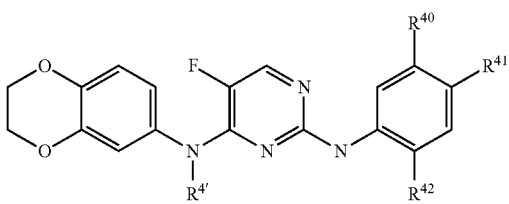
| No. | R⁴' | R⁴⁰ | R⁴¹ | R⁴² | A549 | H1299 |
| --- | --- | --- | --- | --- | --- | --- |
| 1045 | H | H | OMe | OMe | − | |
| 1046 | H | H | OMe | Me | + | + |
| 1047 | H | OMe | H | Me | + | + |
| 1048 | H | Me | H | F | + | + |
| 1049 | H | OMe | Cl | OMe | + | + |
TABLE 11
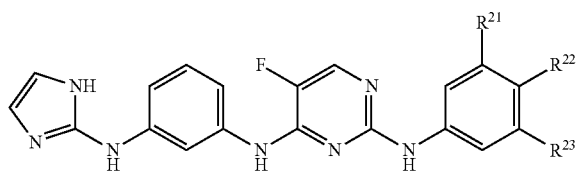
| No. | R²¹ | R²² | R²³ | A549 | H1299 |
| --- | --- | --- | --- | --- | --- |
| 1050 | Me | OMe | Me | + | + |
| 1051 | H | OMe | F | + | + |
| 1052 | Me | H | Me | + | + |
| 1053 | OMe | H | OMe | + | + |
| 1054 | H | H | 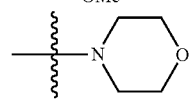 | + | + |
| 1055 | H | H | 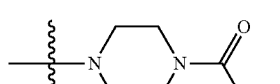 | − | − |
| 1056 | H | 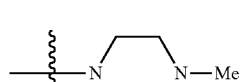 | H | − | − |
| 1057 | H | 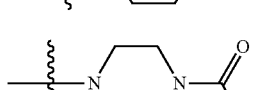 | H | − | − |
| 1058 | H | 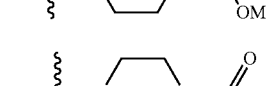 | H | − | − |
| 1059 | H | H | 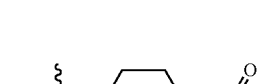 | − | − |

TABLE 12

| No. | R13a | R13b | R19 | R20 | A549 | H1299 |
|---|---|---|---|---|---|---|
| 1060 | Me | OH | Me | Me | + | + |
| 1061 | Me | OMe | Me | Me | + | + |
| 1062 | Me | OMe | H | H | + | + |
| 1063 | Me | OH | H | H | + | + |

TABLE 12-continued

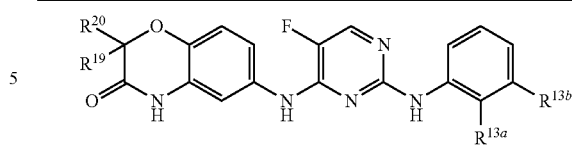

| No. | R13a | R13b | R19 | R20 | A549 | H1299 |
|---|---|---|---|---|---|---|
| 1064 | Me | OH | Me | Me | + | + |
| 1065 | Me | OMe | Me | Me | + | − |

TABLE 13

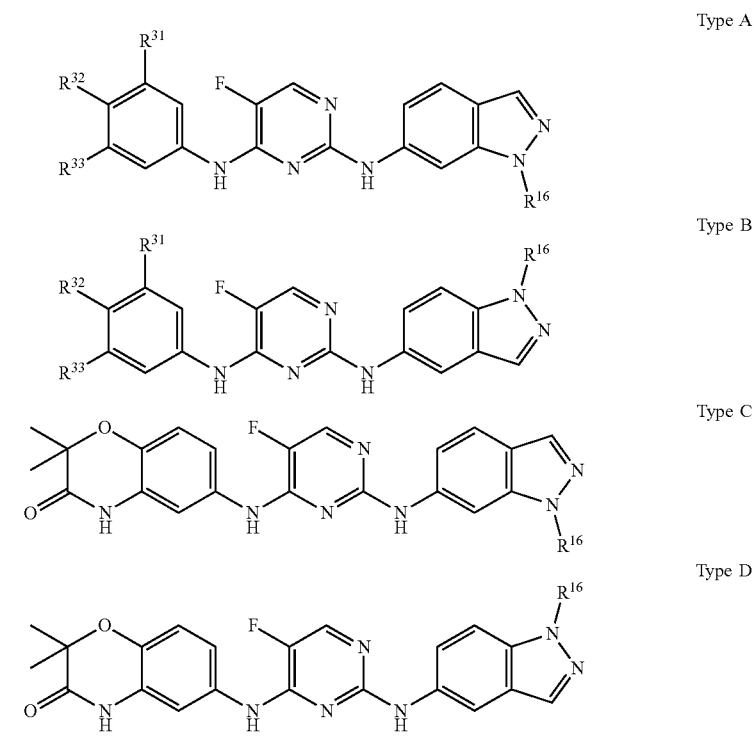

| No. | Type | R16 | R31 | R32 | R33 | A549 | H1299 |
|---|---|---|---|---|---|---|---|
| 1066 | B | ethyl | H | OMe | Cl | | |
| 1067 | B | ethyl | H | Cl | Cl | | |
| 1068 | B | ethyl | — | — | — | | |
| 1069 | B | ethyl | H | F | OMe | | |
| 1070 | A | ethyl | H | OMe | Cl | | |
| 1071 | A | ethyl | H | Cl | Cl | | |
| 1072 | C | ethyl | — | — | — | | |
| 1073 | A | ethyl | H | F | OMe | | |
| 1074 | B | n-propyl | H | OMe | Cl | + | + |
| 1075 | B | n-propyl | H | Cl | Cl | − | − |
| 1076 | D | n-propyl | — | — | — | + | + |
| 1077 | A | n-propyl | H | F | OMe | + | + |
| 1078 | B | n-propyl | H | OMe | Cl | + | + |
| 1079 | B | n-propyl | H | Cl | Cl | + | + |
| 1080 | C | n-propyl | — | — | — | + | + |
| 1081 | A | n-propyl | H | F | OMe | + | + |
| 1082 | B | n-butyl | H | OMe | Cl | + | − |
| 1083 | B | n-butyl | H | Cl | Cl | + | + |
| 1084 | D | n-butyl | — | — | — | + | + |
| 1085 | B | n-butyl | H | F | OMe | + | + |
| 1086 | A | n-butyl | H | OMe | Cl | + | + |
| 1087 | A | n-butyl | H | Cl | Cl | + | + |
| 1088 | C | n-butyl | — | — | — | + | + |
| 1089 | A | n-butyl | H | F | OMe | + | + |

TABLE 13-continued
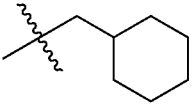 [SMILES: *CC1CCCCC1]
Type A
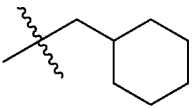 [SMILES: *CC1CCCCC1]
Type B
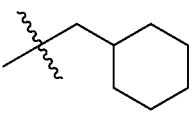 [SMILES: *CC1CCCCC1]
Type C
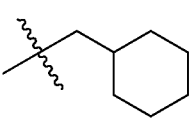 [SMILES: *CC1CCCCC1]
Type D
| No. | Type | R$^{16}$ | R$^{31}$ | R$^{32}$ | R$^{33}$ | A549 | H1299 |
|---|---|---|---|---|---|---|---|
| 1090 | B | 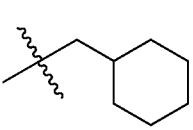 [SMILES: *CC1CCCCC1] | H | OMe | Cl | + | + |
| 1091 | B | 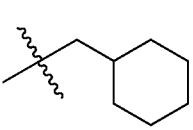 [SMILES: *CC1CCCCC1] | H | Cl | Cl | − | − |
| 1092 | D | 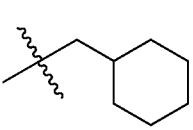 [SMILES: *CC1CCCCC1] | — | — | — | + | + |
| 1093 | B | 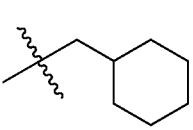 [SMILES: *CC1CCCCC1] | H | F | OMe | + | + |
| 1094 | A | 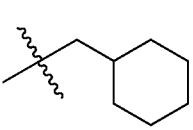 [SMILES: *CC1CCCCC1] | H | OMe | Cl | + | + |
| 1095 | A | 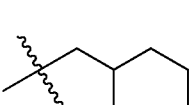 | H | Cl | Cl | + | + |
| 1096 | C | 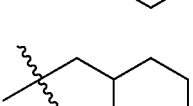 | — | — | — | + | + |

TABLE 13-continued
Type A
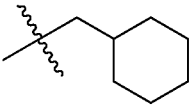 [SMILES: *CC1CCCCC1]
Type B
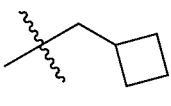 [SMILES: *CC1CCC1]
Type C
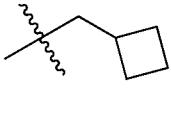 [SMILES: *CC1CCC1]
Type D
| No. | Type | $R^{16}$ | $R^{31}$ | $R^{32}$ | $R^{33}$ | A549 | H1299 |
|---|---|---|---|---|---|---|---|
| 1097 | A |  | H | F | OMe | − | + |
| 1098 | B |  | H | OMe | Cl | − | + |
| 1099 | B |  | H | Cl | Cl | + | + |
| 1100 | D |  | — | — | — | + | + |
| 1101 | B |  | H | F | OMe | + | + |
| 1102 | A |  | H | OMe | Cl | + | + |
| 1103 | A |  | H | Cl | Cl | ° | − |
| 1104 | C |  | — | — | — | + | + |

TABLE 13-continued
Type A
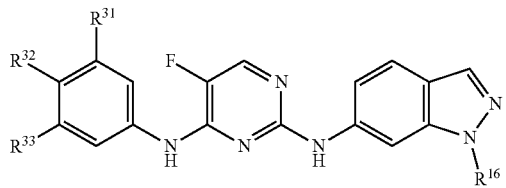
Type B
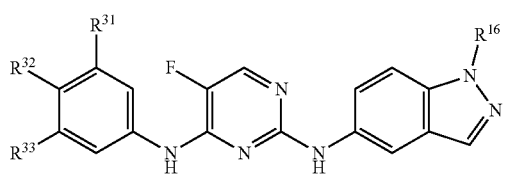
Type C
Type D
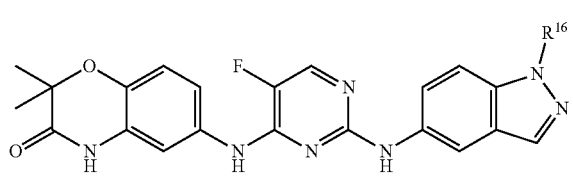
| No. | Type | $R^{16}$ | $R^{31}$ | $R^{32}$ | $R^{33}$ | A549 | H1299 |
|---|---|---|---|---|---|---|---|
| 1105 | A | ![cyclobutylmethyl] | H | F | OMe | + | + |
| 1106 | B | ![cyclopropylmethyl] | H | OMe | Cl | + | + |
| 1107 | B | ![cyclopropylmethyl] | H | Cl | Cl | − | − |
| 1108 | D | ![cyclopropylmethyl] | — | — | — | + | + |
| 1109 | B | ![cyclopropylmethyl] | H | F | OMe | + | + |
| 1110 | A | ![cyclopropylmethyl] | H | OMe | Cl | + | + |
| 1111 | A | ![cyclopropylmethyl] | H | Cl | Cl | + | + |
| 1112 | C | ![cyclopropylmethyl] | — | — | — | + | + |

TABLE 13-continued
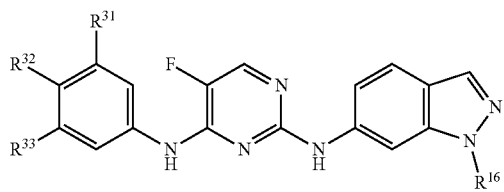
Type A
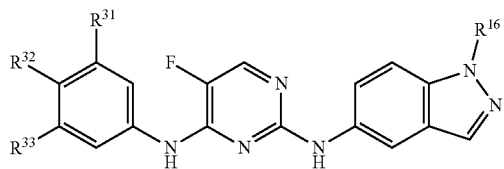
Type B
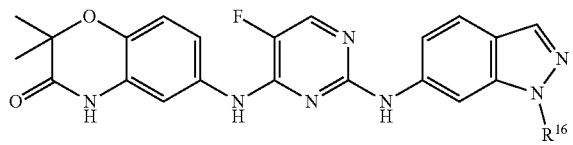
Type C
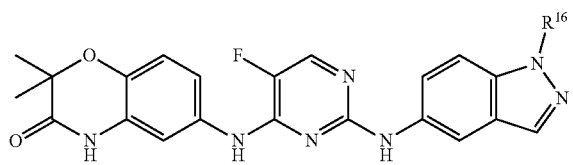
Type D
| No. | Type | R¹⁶ | R³¹ | R³² | R³³ | A549 | H1299 |
|---|---|---|---|---|---|---|---|
| 1113 | A | cyclopropylmethyl | H | F | OMe | + | + |
| 1114 | B | cyclohexyl | H | OMe | Cl | | |
| 1115 | B | cyclohexyl | H | Cl | Cl | + | + |
| 1116 | D | cyclohexyl | — | — | — | | |
| 1117 | B | cyclohexyl | H | F | OMe | + | + |
| 1118 | A | cyclohexyl | H | OMe | Cl | + | + |
| 1119 | A | cyclohexyl | H | Cl | Cl | + | + |
| 1120 | C | cyclohexyl | — | — | — | | |

TABLE 13-continued
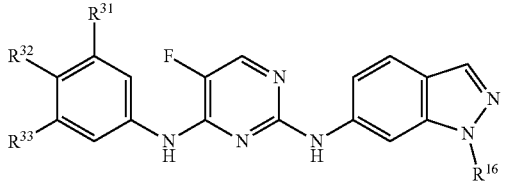
Type A
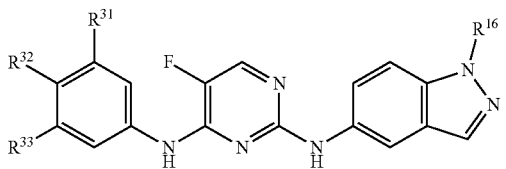
Type B
Type C
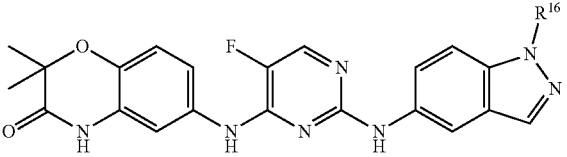
Type D
| No. | Type | R$^{16}$ | R$^{31}$ | R$^{32}$ | R$^{33}$ | A549 | H1299 |
|---|---|---|---|---|---|---|---|
| 1121 | A | 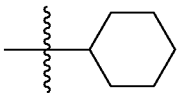 | H | F | OMe | + | + |
| 1122 | C | methyl | — | — | — | | |
| 1123 | C | methyl | — | — | — | | |
| 1124 | C | methyl | — | — | — | | |
| 1125 | C | methyl | — | — | — | | |
| 1126 | C | methyl | — | — | — | | |
| 1127 | B | i-propyl | H | OMe | Cl | | |
| 1128 | B | i-propyl | H | Cl | Cl | | |
| 1129 | D | i-propyl | — | — | — | | |
| 1130 | B | i-propyl | H | F | OMe | | |
| 1131 | A | i-propyl | H | OMe | Cl | | |
| 1132 | A | i-propyl | H | Cl | Cl | | |
| 1133 | C | i-propyl | — | — | — | | |
| 1134 | C | methyl | — | — | — | | |
| 1135 | C | H | — | — | — | | |
| 1136 | C | H | — | — | — | | |
| 1137 | C | ethyl | — | — | — | | |
| 1138 | C | i-propyl | — | — | — | | |
TABLE 14
| No. | Structure | A549 | H1299 |
|---|---|---|---|
| 1139 | 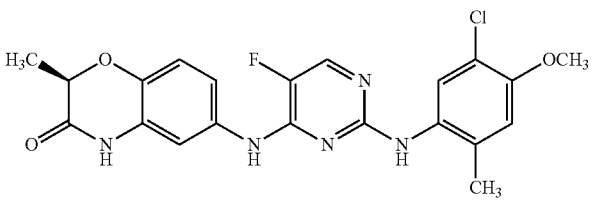 [SMILES: COc1cc(C)c(Nc2ncc(F)c(Nc3ccc4c(c3)NC(=O)[C@@H](C)O4)n2)cc1Cl] | + | − |

TABLE 14-continued

| No. | Structure | A549 | H1299 |
|---|---|---|---|
| 1140 | 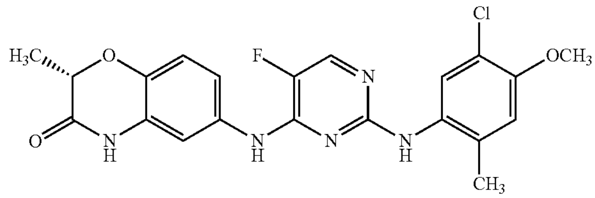 [SMILES: COc1cc(C)c(Nc2ncc(F)c(Nc3ccc4c(c3)NC(=O)[C@H](C)O4)n2)cc1Cl] | − | − |
| 1141 | 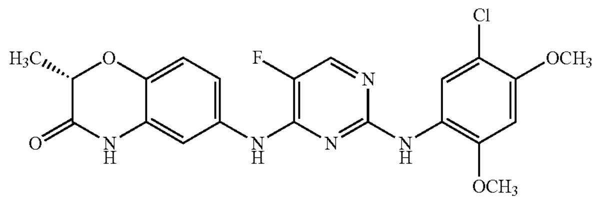 [SMILES: COc1cc(OC)c(Nc2ncc(F)c(Nc3ccc4c(c3)NC(=O)[C@H](C)O4)n2)cc1Cl] | − | − |
| 1142 | 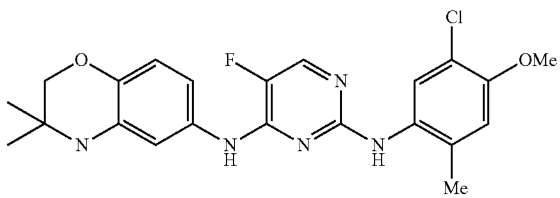 [SMILES: COc1cc(C)c(Nc2ncc(F)c(Nc3ccc4c(c3)NC(C)(C)CO4)n2)cc1Cl] | + | − |
| 1143 | 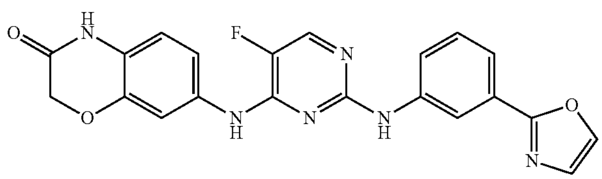 [SMILES: O=C1COc2cc(Nc3nc(Nc4cccc(-c5ncco5)c4)ncc3F)ccc2N1] | | |
| 1144 | 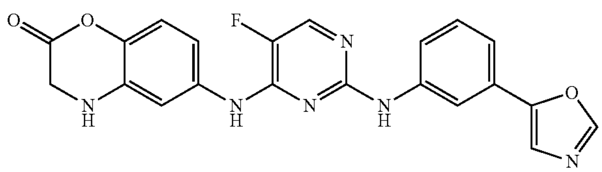 [SMILES: O=C1CNc2cc(Nc3nc(Nc4cccc(-c5cnco5)c4)ncc3F)ccc2O1] | | |
| 1145 | 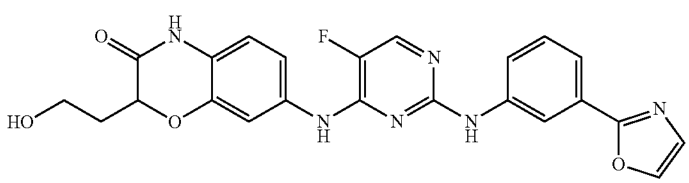 [SMILES: O=C1Nc2ccc(Nc3nc(Nc4cccc(-c5ncco5)c4)ncc3F)cc2OC1CCO] | + | + |
| 1146 | 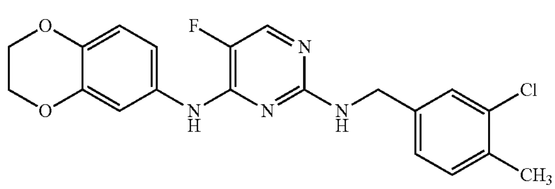 [SMILES: Cc1ccc(CNc2ncc(F)c(Nc3ccc4c(c3)OCCO4)n2)cc1Cl] | + | − |
| 1147 | 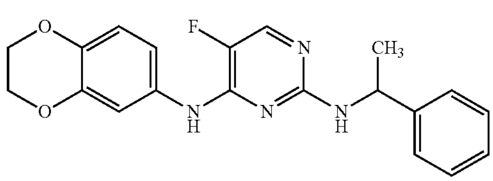 [SMILES: CC(Nc1ncc(F)c(Nc2ccc3c(c2)OCCO3)n1)c1ccccc1] | + | + |

TABLE 14-continued

| No. | Structure | A549 | H1299 |
|-----|-----------|------|-------|
| 1148 | 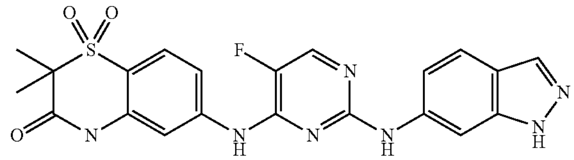 [SMILES: CC1(C)C(=O)Nc2cc(Nc3nc(Nc4ccc5cn[nH]c5c4)ncc3F)ccc2S1(=O)=O] | | |
| 1149 | 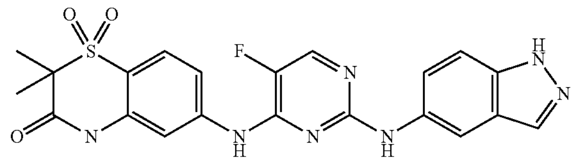 [SMILES: CC1(C)C(=O)Nc2cc(Nc3nc(Nc4ccc5[nH]ncc5c4)ncc3F)ccc2S1(=O)=O] | | |
| 1150 | 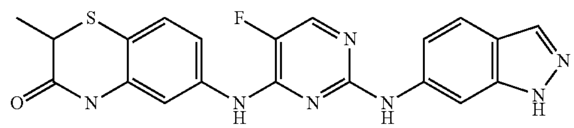 [SMILES: CC1Sc2ccc(Nc3nc(Nc4ccc5cn[nH]c5c4)ncc3F)cc2NC1=O] | | |
| 1151 | 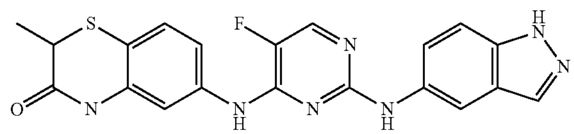 [SMILES: CC1Sc2ccc(Nc3nc(Nc4ccc5[nH]ncc5c4)ncc3F)cc2NC1=O] | | |
| 1152 | 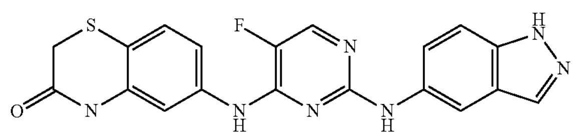 [SMILES: O=C1CSc2ccc(Nc3nc(Nc4ccc5[nH]ncc5c4)ncc3F)cc2N1] | | |
| 1153 | 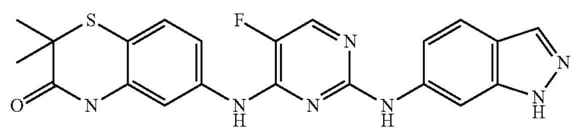 [SMILES: CC1(C)Sc2ccc(Nc3nc(Nc4ccc5cn[nH]c5c4)ncc3F)cc2NC1=O] | | |
| 1154 | 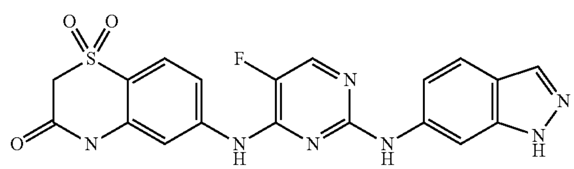 [SMILES: O=C1CS(=O)(=O)c2ccc(Nc3nc(Nc4ccc5cn[nH]c5c4)ncc3F)cc2N1] | | |
| 1155 | 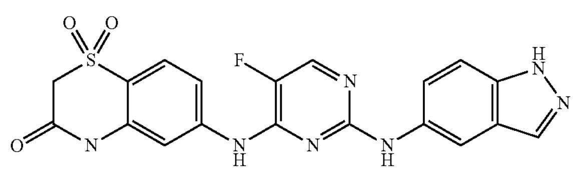 [SMILES: O=C1CS(=O)(=O)c2ccc(Nc3nc(Nc4ccc5[nH]ncc5c4)ncc3F)cc2N1] | | |
| 1156 | 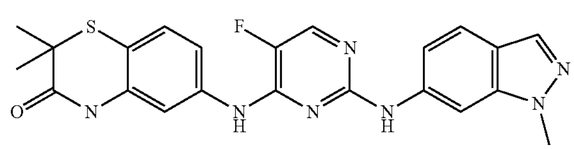 [SMILES: Cn1ncc2ccc(Nc3ncc(F)c(Nc4ccc5c(c4)NC(=O)C(C)(C)S5)n3)cc21] | | |
| 1157 | 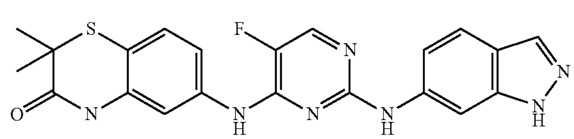 [SMILES: CC1(C)Sc2ccc(Nc3nc(Nc4ccc5cn[nH]c5c4)ncc3F)cc2NC1=O] | | |

TABLE 14-continued

| No. | Structure | A549 | H1299 |
|---|---|---|---|
| 1158 | 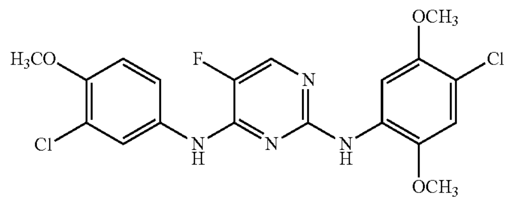 [SMILES: COc1ccc(Nc2nc(Nc3cc(OC)c(Cl)cc3OC)ncc2F)cc1Cl] | + | + |
| 1159 | 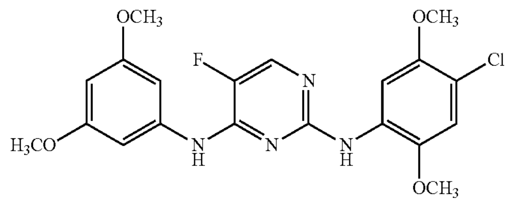 [SMILES: COc1cc(Nc2nc(Nc3cc(OC)c(Cl)cc3OC)ncc2F)cc(OC)c1] | + | + |
| 1160 | 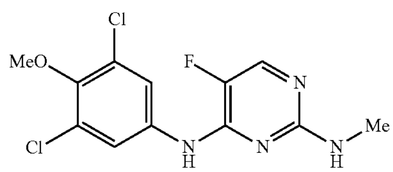 [SMILES: CNc1ncc(F)c(Nc2cc(Cl)c(OC)c(Cl)c2)n1] | + | + |
| 1161 | 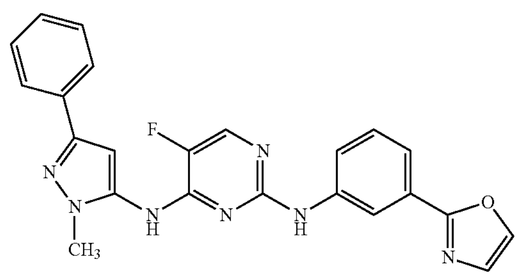 [SMILES: Cn1nc(-c2ccccc2)cc1Nc1nc(Nc2cccc(-c3ncco3)c2)ncc1F] | + | |
| 1162 | 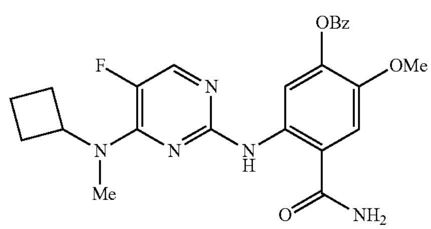 | + | + |
| 1163 | 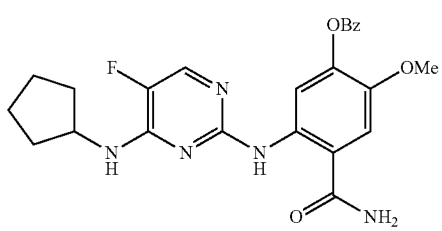 | + | + |
| 1164 | 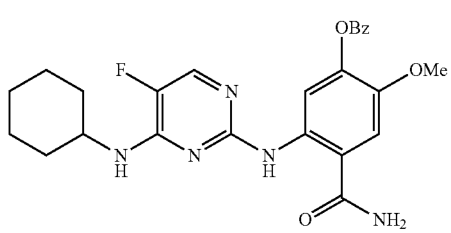 | + | + |

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-pyrimidinediamines that include ester moieties may be considered prodrugs of their corresponding carboxylic acid, regardless of whether the ester form is pharmacologically active.

In the prodrugs of the invention, any available functional moiety may be masked with a progroup to yield a prodrug. Functional groups within the 2,4-pyrimidinediamine compounds that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the prodrugs of the invention.

In one illustrative embodiment, the prodrugs are compounds according to structural formulae (I)-(VI) in which $R^a$, $R^b$ and $R^c$ may be, in addition to their previously-defined alternatives, a progroup.

In another illustrative embodiment, the prodrugs are compounds according to structural formulae (I)-(VI) in which $R^{2'}$ and $R^{4'}$ are each, independently of one another, a progroup. Specific examples of progroups according to this embodiment of the invention include, but are not limited to, —C(O)CH$_3$, —C(O)NHR$^h$ and —S(O)$_2$R$^h$, where R$^h$ is selected from the group consisting of lower alkyl, (C5-C15) aryl and (C3-C8) cycloalkyl.

Those of skill in the art will appreciate that many of the compounds and prodrugs described herein, as well as the various compound species specifically described and/or illustrated herein, may exhibit the phenomena of tautomerism, conformational isomerism, geometric isomerism and/or optical isomerism. For example, the compounds and prodrugs may include one or more chiral centers and/or double bonds and as a consequence may exist as stereoisomers, such as double-bond isomers (i.e., geometric isomers), enantiomers and diasteromers and mixtures thereof, such as racemic mixtures. As another example, the compounds and prodrugs may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms. In cases of limited rotation around the 2,4-pryimidinediamine core structure, atrop isomers are also possible and are also specifically included in the compounds and/or prodrugs of the invention.

Depending upon the nature of the various substituents, the 2,4-pyrimidinediamine compounds and prodrugs may be in the form of salts. Such salts include salts suitable for pharmaceutical uses ("pharmaceutically-acceptable salts"), salts suitable for veterinary uses, etc. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The 2,4-pyrimidinediamine compounds and prodrugs, as well as the salts thereof, may also be in the form of hydrates, solvates and N-oxides, as are well-known in the art.

5.3 Methods of Synthesis

The 2,4-pyrimidinediamine compounds and prodrugs may be synthesized via a variety of different synthetic routes using commercially available starting materials and/or starting materials prepared by conventional synthetic methods. Suitable exemplary methods that may be routinely adapted to synthesize the 2,4-pyrimidinediamine compounds and prodrugs are found in U.S. Pat. No. 5,958,935, the disclosure of which is incorporated herein by reference. Specific examples describing the synthesis of numerous 2,4-pyrimidinediamine compounds and prodrugs, as well as intermediates therefor, are described in copending U.S. application Ser. No. 10/355,543, filed Jan. 31, 2003 (US 2004-0029902 published Feb. 12, 2004), WO 03/63794, copending U.S.

application Ser. No. 10/631,029, filed Jul. 29, 2003, WO 2004/014312, copending application Ser. No. 10/903,263, filed Jul. 30, 2004 and international application Ser. No. PCT/US04/024716, filed Jul. 30, 2004, the contents of which are incorporated herein by reference. All of the compounds described herein (including prodrugs) can be prepared according to, or by routine adaptation of, these various methods.

A variety of exemplary synthetic routes that can be used to synthesize the 2,4-pyrimidinediamine compounds and prodrugs are described in Schemes (I)-(XI), below. In Schemes (I)-(XI), like-numbered compounds have similar structures. These methods may be routinely adapted to synthesize the corresponding N2- and/or N4-alkylated compounds and prodrugs, as illustrated in Scheme (XII).

In one exemplary embodiment, the compounds can be synthesized from substituted or unsubstituted uracils or thiouracils as illustrated in Scheme (I), below:

tions to yield 2,4-bishalo pyrimidine 4. Depending upon the $R^5$ substituent, in pyrimidine 4, the halide at the C4 position is more reactive towards nucleophiles than the halide at the C2 position. This differential reactivity can be exploited to synthesize 2,4-pyrimidinediamines according structural formulae (I) by first reacting 2,4-bishalopyrimidine 4 with one equivalent of amine 10, yielding 4N-substituted-2-halo-4-pyrimidineamine 8, followed by amine 6 to yield a 2,4-pyrimidinediamine according structural formulae (I). 2N,4N-bis(substituted)-2,4-pyrimidinediamines 12 and 14 can be obtained by reacting 2,4-bishalopyrimidine 4 with excess 6 or 10, respectively.

In most situations, the C4 halide is more reactive towards nucleophiles, as illustrated in the Scheme. However, as will be recognized by skilled artisans, the identity of the $R^5$ substituent may alter this reactivity. For example, when $R^5$ is trifluoromethyl, a 50:50 mixture of 4N-substituted-4-pyrimidineamine 8 and the corresponding 2N-substituted-

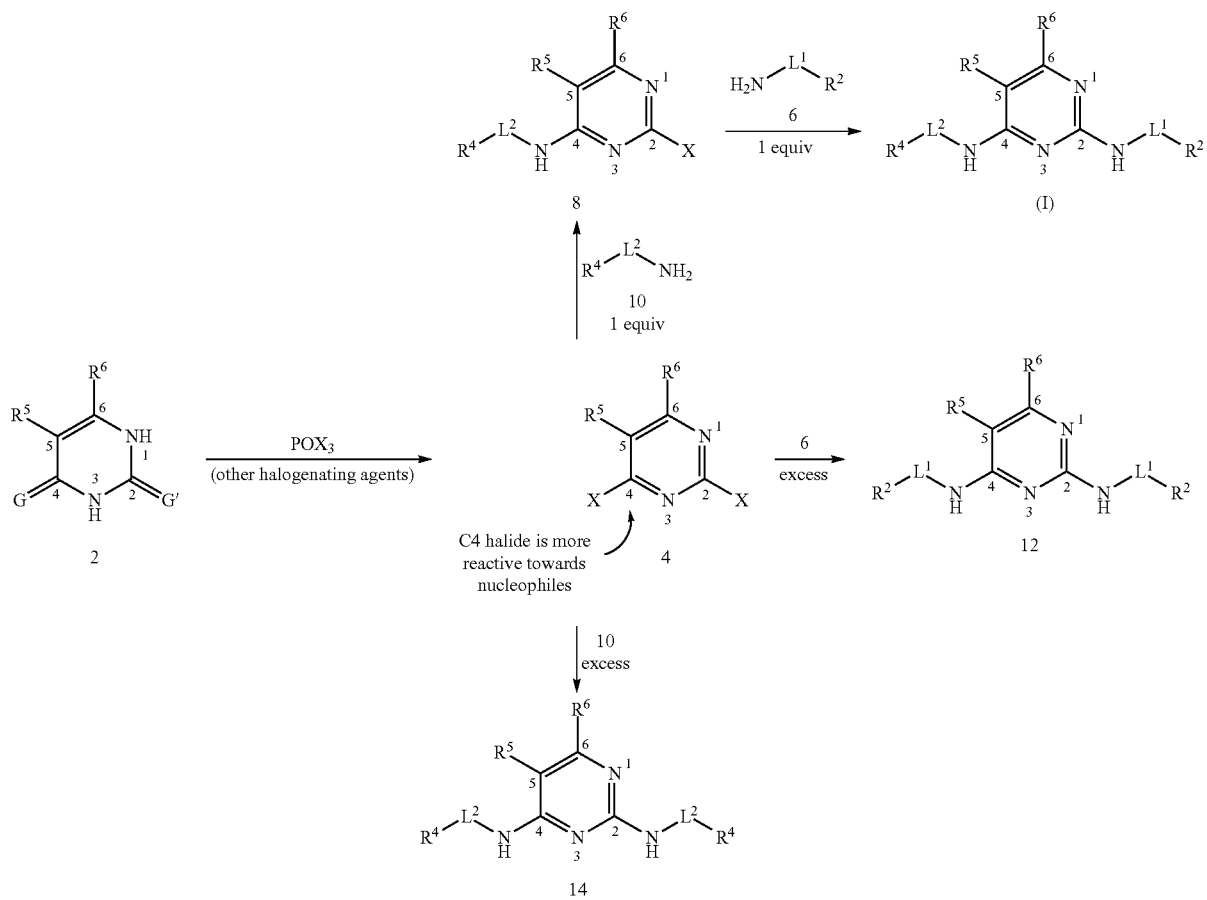

Scheme (I)

In Scheme (I), $R^2$, $R^4$, $R^5$, $R^6$, $L^1$ and $L^2$ are as previously defined for structural formulae (I), X is a halogen (e.g., F, Cl, Br or I) and G and G' are each, independently of one another, selected from the group consisting of O and S. Referring to Scheme (I), uracil or thiouracil 2 is dihalogenated at the 2- and 4-positions using standard halogenating agent $POX_3$ (or other standard halogenating agent) under standard condi- 2-pyrimidineamine is obtained. Regardless of the identity of the $R^5$ substituent, the regioselectivity of the reaction can be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions may be used: heat to 175° C. in ethanol for 5-20 min. in a Smith Reactor (Personal Chemistry) in a sealed tube (at 20 bar pressure).

The uracil or thiouracil 2 starting materials may be purchased from commercial sources or prepared using standard techniques of organic chemistry. Commercially available uracils and thiouracils that can be used as starting materials in Scheme (I) include, by way of example and not limitation, uracil (Aldrich #13,078-8; CAS Registry 66-22-8); 2-thio-uracil (Aldrich #11,558-4; CAS Registry 141-90-2); 2,4-dithiouracil (Aldrich #15,846-1; CAS Registry 2001-93-6); 5-bromouracil (Aldrich #85,247-3; CAS Registry 51-20-7); 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); 5-(trifluoromethyl)-uracil (Aldrich #22,327-1; CAS Registry 54-20-6). Additional 5-substituted uracils and/or thiouracils are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Amines 6 and 10 may be purchased from commercial sources or, alternatively, may be synthesized utilizing standard techniques. For example, suitable amines may be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances, amines 6 and 10 and/or substituents $R^5$ and/or $R^6$ on uracil or thiouracil 2 may include functional groups that require protection during synthesis. The exact identity of any protecting group(s) used will depend upon the identity of the functional group being protected, and will be apparent to these of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

A specific embodiment of Scheme (I) utilizing 5-fluorouracil (Aldrich #32,937-1) as a starting material is illustrated in Scheme (II), below:

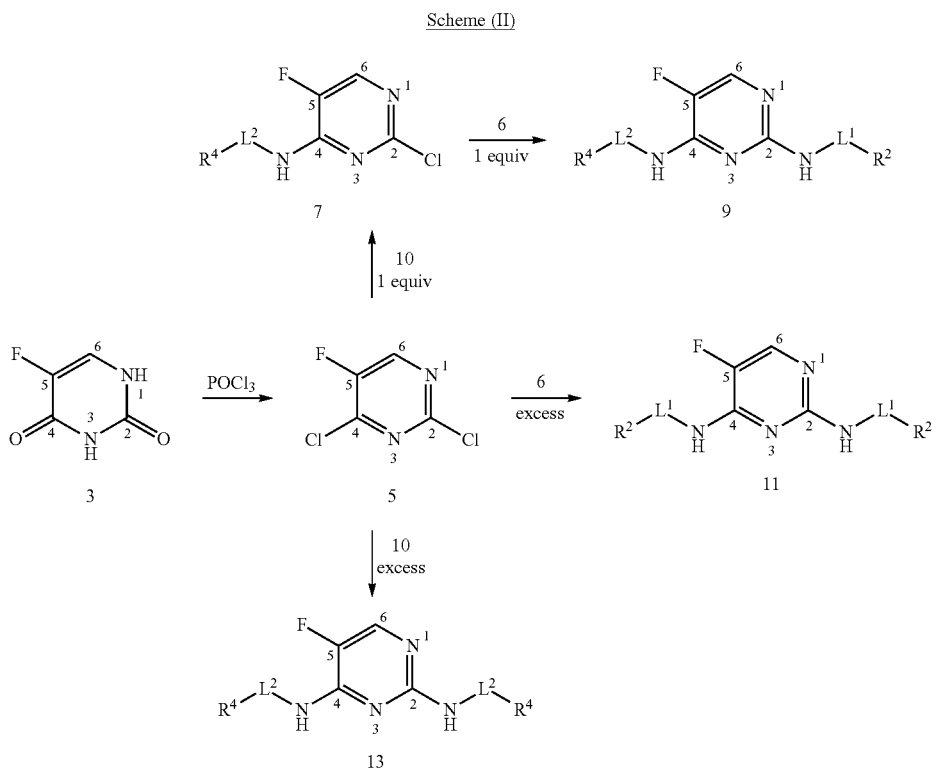

Scheme (II)

In Scheme (II), $R^2$, $R^4$, $L^1$ and $L^2$ are as previously defined for Scheme (I). According to Scheme (II), 5-fluorouracil 3 is halogenated with $POCl_3$ to yield 2,4-dichloro-5-fluoropyrimidine 5, which is then reacted with excess amine 6 or 10 to yield N2,N4-bis substituted 5-fluoro-2,4-pyrimidinediamine 11 or 13, respectively. Alternatively, non-bis-2N,4N-disubstituted-5-fluoro-2,4-pyrimidinediamine 9 may be obtained by reacting 2,4-dichloro-5-fluoropyrimidine 5 with one equivalent of amine 10 (to yield 2-chloro-N4-substituted-5-fluoro-4-pyrimidineamine 7) followed by one or more equivalents of amine 6.

In another exemplary embodiment, the 2,4-pyrimidinediamine compounds of the invention may be synthesized from substituted or unsubstituted cytosines as illustrated in Schemes (IIa) and (IIb), below:

Scheme (IIa)

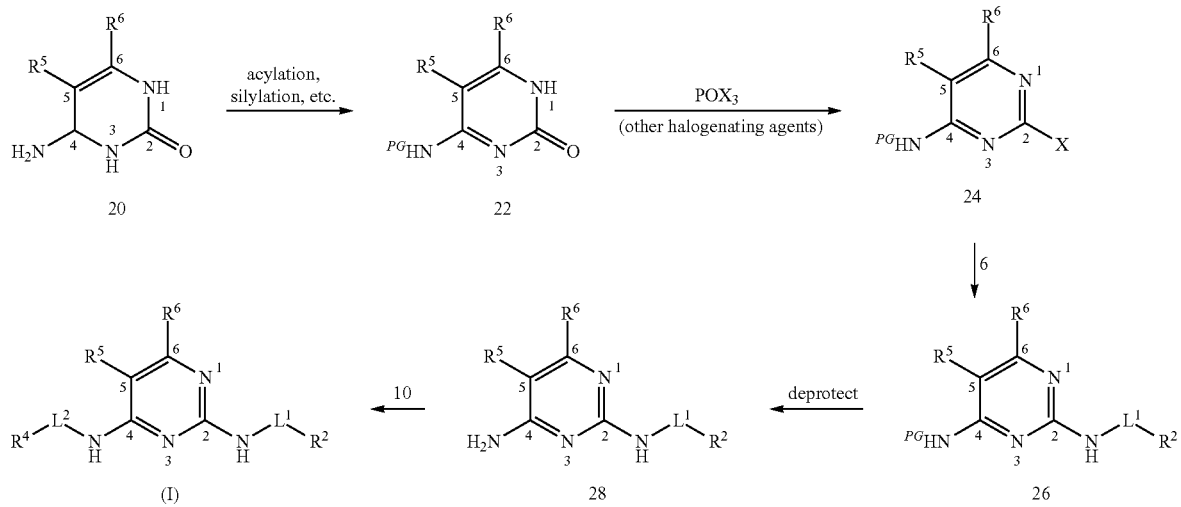

Scheme (IIb)

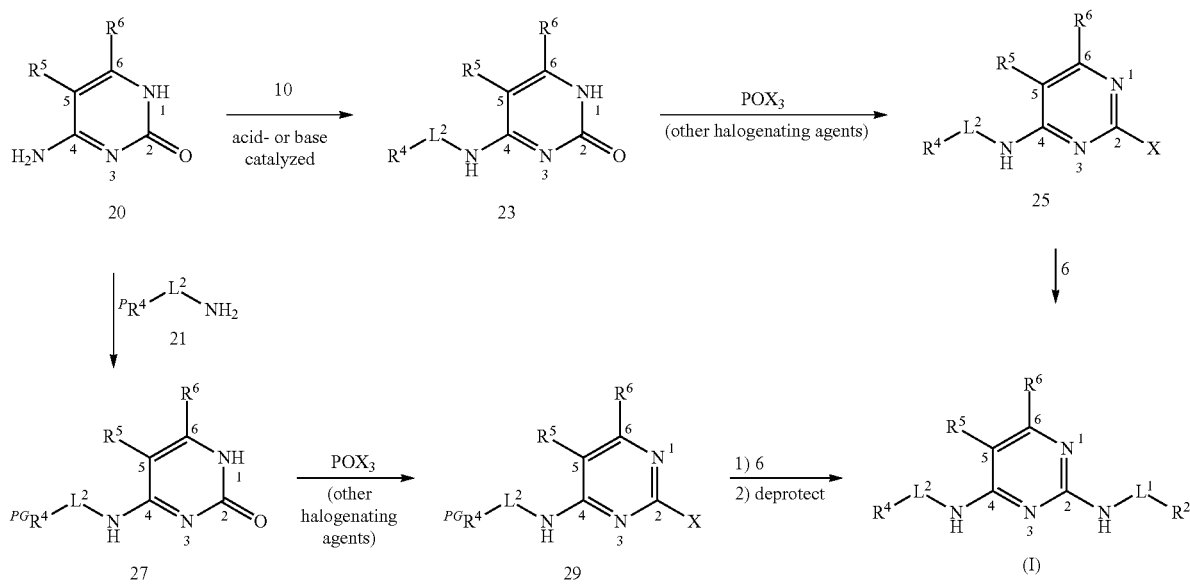

In Schemes (IIa) and (IIb), $R^2$, $R^4$, $R^5$, $R^6$, $L^1$, $L^2$ and X are as previously defined for Scheme (I) and PG represents a protecting group. Referring to Scheme (IIa), the C4 exocyclic amine of cytosine 20 is first protected with a suitable protecting group PG to yield N4-protected cytosine 22. For specific guidance regarding protecting groups useful in this context, see Vorbrüggen and Ruh-Pohlenz, 2001, *Handbook of Nucleoside Synthesis*, John Wiley & Sons, NY, pp. 1-631 ("Vorbrüggen"). Protected cytosine 22 is halogenated at the C2 position using a standard halogenation reagent under standard conditions to yield 2-chloro-4N-protected-4-pyrimidineamine 24. Reaction with amine 6 followed by deprotection of the C4 exocyclic amine and reaction with amine 10 yields a 2,4-pyrimidinediamine according to structural formulae (I).

Alternatively, referring to Scheme (IIb), cytosine 20 may be reacted with amine 10 or protected amine 21 to yield N4-substituted cytosine 23 or 27, respectively. These substituted cytosines may then be halogenated as previously described, deprotected (in the case of N4-substituted cytosine 27) and reacted with amine 6 to yield a 2,4-pyrimidinediamine according to structural formulae (I).

Commercially-available cytosines that may be used as starting materials in Schemes (IIa) and (IIb) include, but are not limited to, cytosine (Aldrich #14,201-8; CAS Registry 71-30-7); $N^4$-acetylcytosine (Aldrich #37,791-0; CAS Registry 14631-20-0); 5-fluorocytosine (Aldrich #27,159-4; CAS Registry 2022-85-7); and 5-(trifluoromethyl)-cytosine. Other suitable cytosines useful as starting materials in Schemes (IIa) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

In still another exemplary embodiment, the 2,4-pyrimidinediamine compounds may be synthesized from substituted or unsubstituted 2-amino-4-pyrimidinols as illustrated in Scheme (III), below:

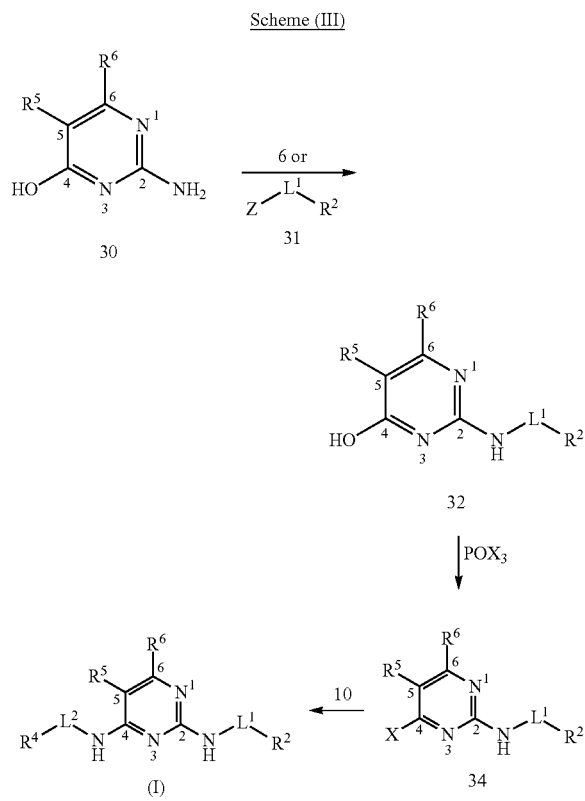

Alternatively, the 2,4-pyrimidinediamine compounds may be prepared from substituted or unsubstituted 4-amino-2-pyrimidinols as illustrated in Scheme (IV), below:

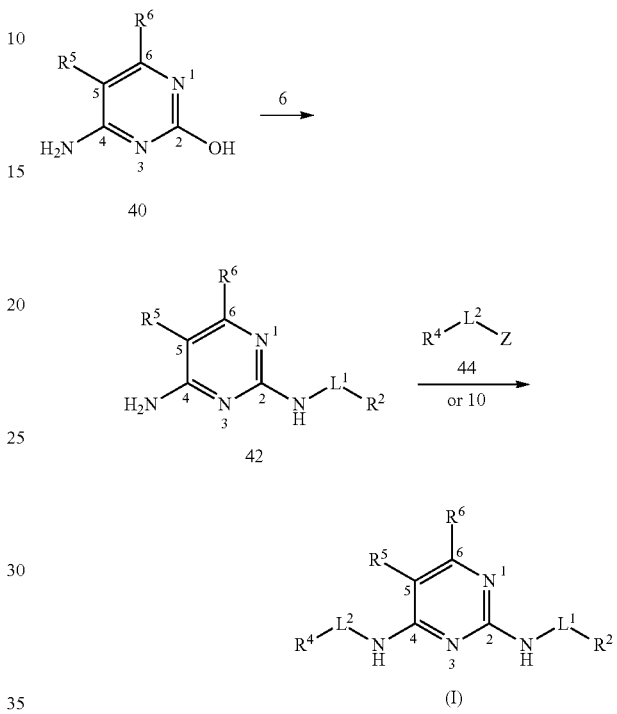

In Scheme (III), $R^2$, $R^4$, $R^5$, $R^6$, $L^1$, $L^2$ and X are as previously defined for Scheme (I) and Z is a leaving group as discussed in more detail in connection with Scheme IV, infra. Referring to Scheme (III), 2-amino-4-pyrimidinol 30 is reacted with amine 6 (or optionally protected amine 21) to yield N2-substituted-4-pyrimidinol 32, which is then halogenated as previously described to yield N2-substituted-4-halo-2-pyrimidineamine 34. Optional deprotection (for example if protected amine 21 was used in the first step) followed by reaction with amine 10 affords a 2,4-pyrimidinediamine according to structural formulae (I). Alternatively, pyrimidinol 30 can be reacted with acylating agent 31.

Suitable commercially-available 2-amino-4-pyrimidinols 30 that can be used as starting materials in Scheme (III) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

In Scheme (IV), $R^2$, $R^4$, $R^5$, $R^6$, $L^1$ and $L^2$ are as previously defined for Scheme (I) and Z represents a leaving group. Referring to Scheme (IV), the C2-hydroxyl of 4-amino-2-pyrimidinol 40 is more reactive towards nucleophiles than the C4-amino such that reaction with amine 6 yields N2-substituted-2,4-pyrimidinediamine 42. Subsequent reaction with compound 44, which includes a good leaving group Z, or amine 10 yields a 2,4-pyrimidinediamine according to structural formulae (I). Compound 44 may include virtually any leaving group that can be displaced by the C4-amino of N2-substituted-2,4-pyrimidinediamine 42. Suitable leaving groups Z include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate") and metanitro benzene sulfonyloxy ("nosylate"). Other suitable leaving groups will be apparent to those of skill in the art.

Substituted 4-amino-2-pyrimidinol starting materials may be obtained commercially or synthesized using standard techniques. Myriad textbook references teaching suitable synthetic methods are provided infra.

In still another exemplary embodiment, the 2,4-pyrimidinediamine compounds can be prepared from 2-chloro-4-aminopyrimidines or 2-amino-4-chloropyrimidines as illustrated in Scheme (V), below:

Scheme (V)

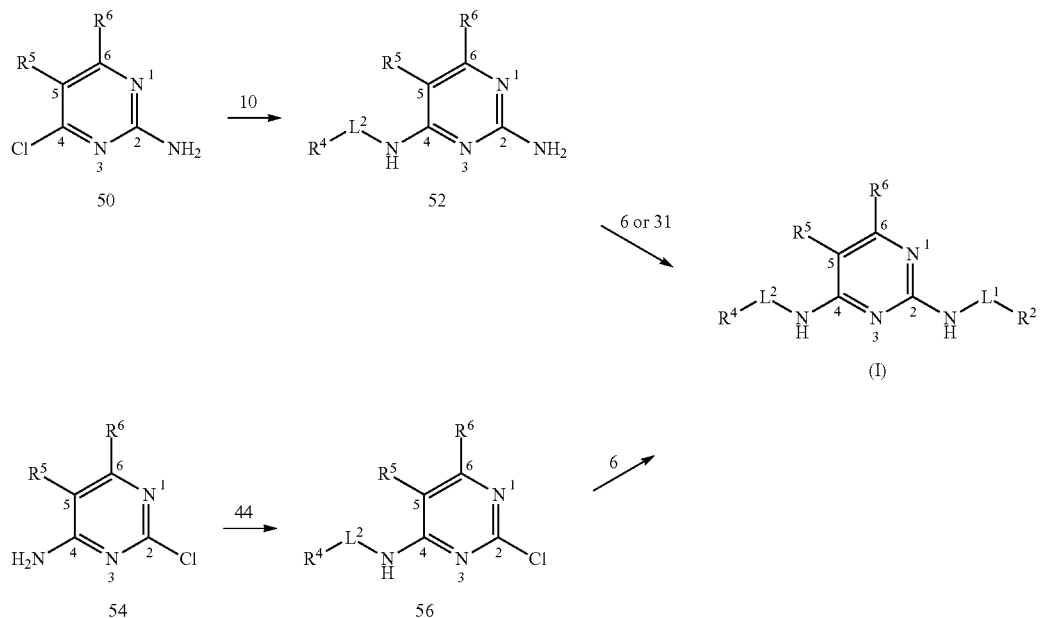

(I)

In Scheme (V), $R^2$, $R^4$, $R^5$, $R^6$, $L^1$, $L^2$ and X are as defined for Scheme (I) and Z is as defined for Scheme (IV). Referring to Scheme (V), 2-amino-4-chloropyrimidine 50 is reacted with amino 10 to yield 4N-substituted-2-pyrimidineamine 52 which, following reaction with compound 31 or amine 6, yields a 2,4-pyrimidinediamine according to structural formulae (I). Alternatively, 2-chloro-4-amino-pyrimidine 54 may be reacted with compound 44 followed by amine 6 to yield a compound according to structural formulae (I).

A variety of pyrimidines 50 and 54 suitable for use as starting materials in Scheme (V) are commercially available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

Alternatively, 4-chloro-2-pyrimidineamines 50 may be prepared as illustrated in Scheme (Va):

Scheme (Va)

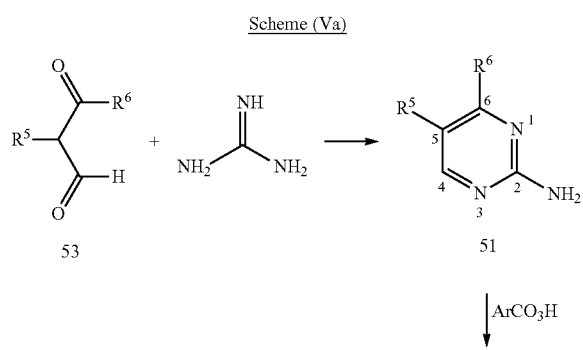

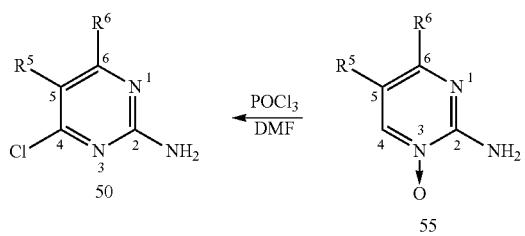

-continued

In Scheme (Va), $R^5$ and $R^6$ are as previously defined for structural formulae (I). In Scheme (Va), dicarbonyl 53 is reacted with guanidine to yield 2-pyrimidineamine 51. Reaction with peracids like m-chloroperbenzoic acid, trifluoroperacetic acid or urea hydrogen peroxide complex yields N-oxide 55, which is then halogenated to give 4-chloro-2-pyrimidineamine 50. The corresponding 4-halo-2-pyrimidineamines may be obtained by using suitable halogenation reagents.

In yet another exemplary embodiment, the 2,4-pyrimidinediamine compounds can be prepared from substituted or unsubstituted uridines as illustrated in Scheme (VI), below:

Scheme (VI)

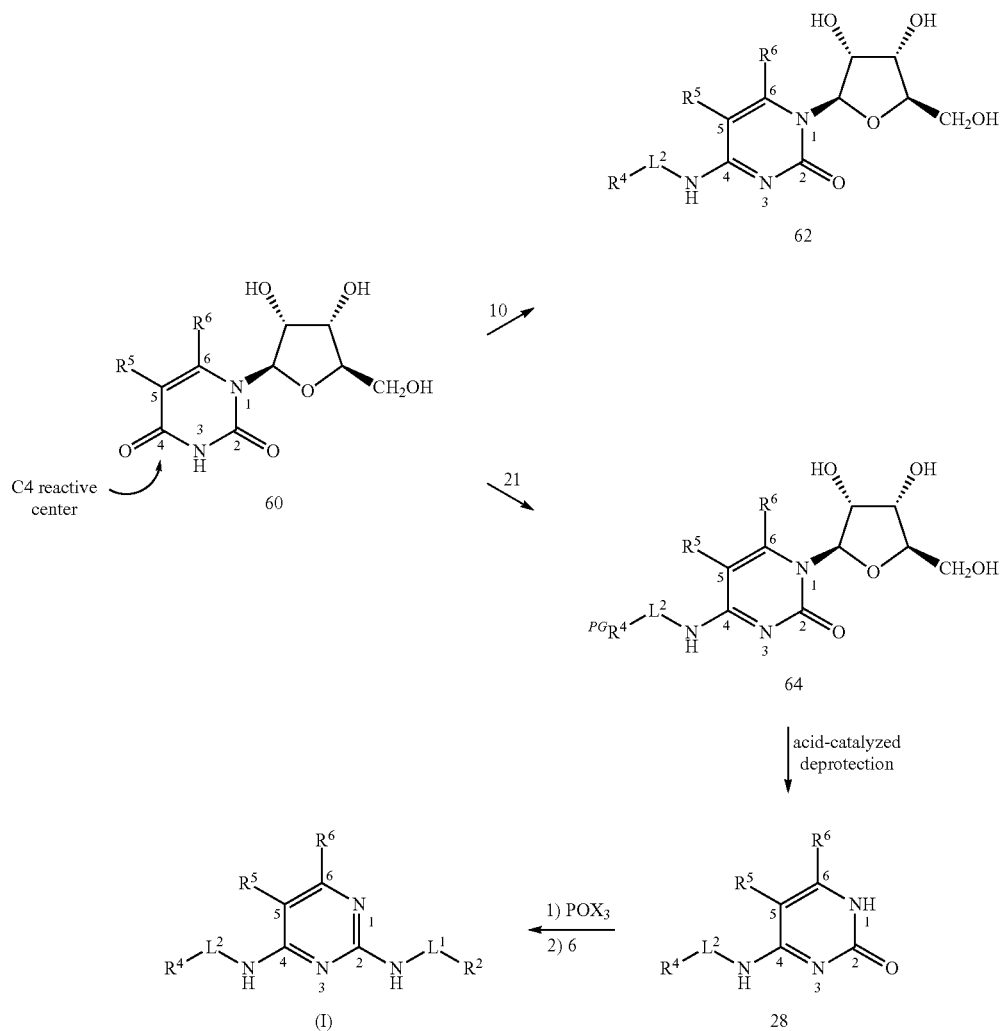

In Scheme (VI), $R^2$, $R^4$, $R^5$, $R^6$, $L^1$, $L^2$ and X are as previously defined for Scheme (I) and the superscript PG represents a protecting group, as discussed in connection with Scheme (IIb). According to Scheme (VI), uridine 60 has a C4 reactive center such that reaction with amine 10 or protected amine 21 yields N4-substituted cytidine 62 or 64, respectively. Acid-catalyzed deprotection of N4-substituted 62 or 64 (when "PG" represents an acid-labile protecting group) yields N4-substituted cytosine 28, which may be subsequently halogenated at the C2-position and reacted with amine 6 to yield a 2,4-pyrimidinediamine according to structural formulae (I).

Cytidines may also be used as starting materials in an analogous manner, as illustrated in Scheme (VII), below:

Scheme (VII)

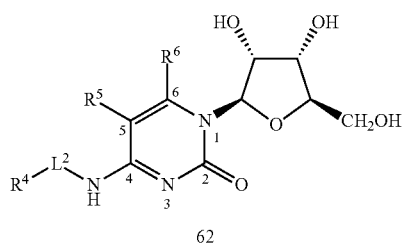

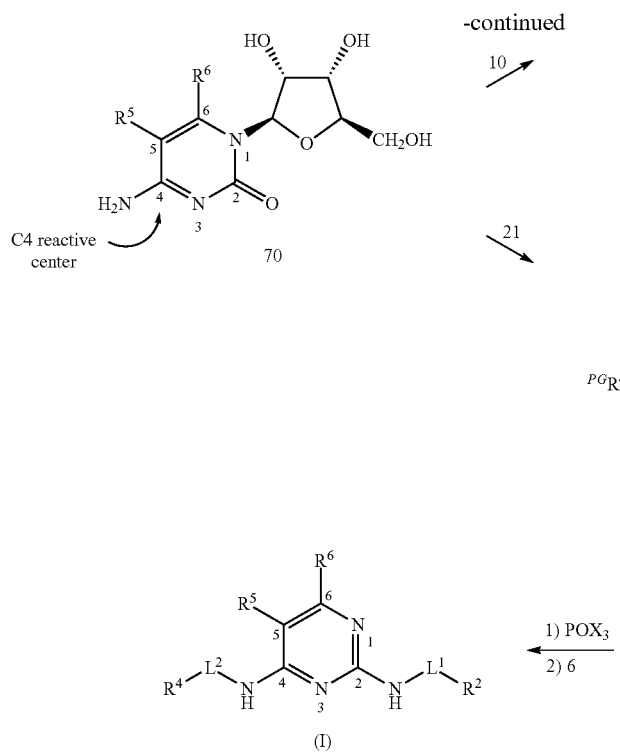

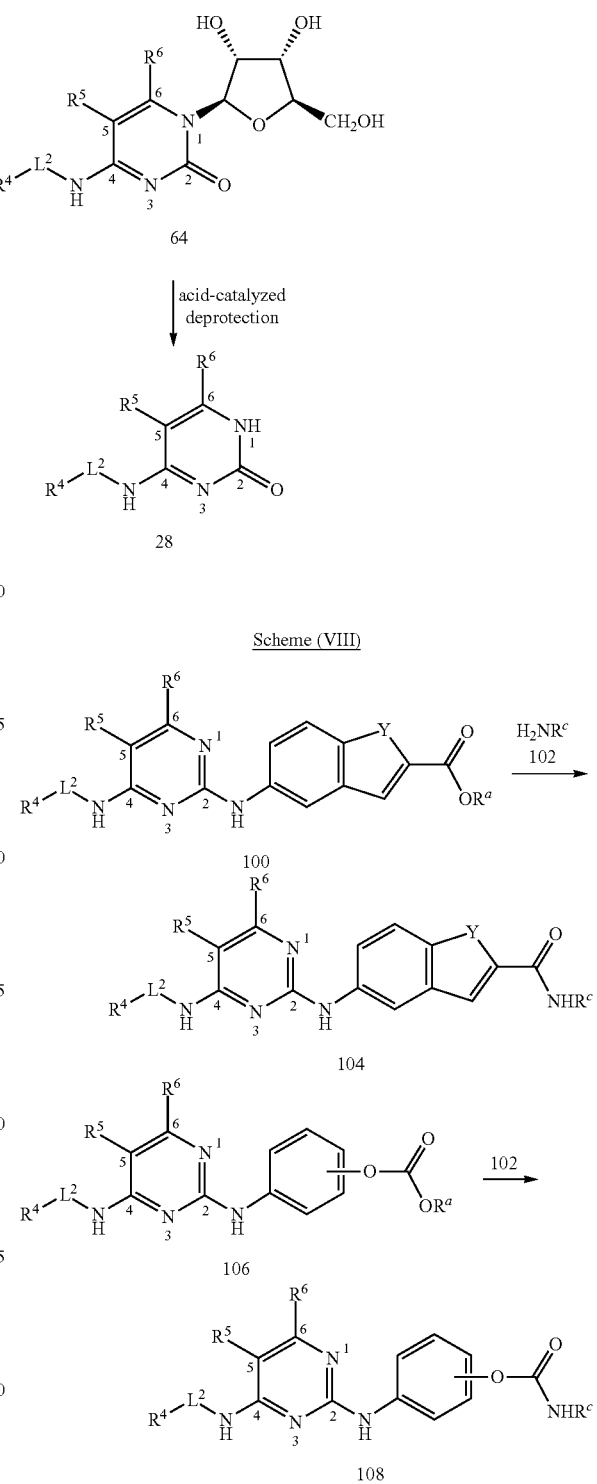

In Scheme (VII), $R^2$, $R^4$, $R^5$, $R^6$, $L^1$, $L^2$ and X are as previously defined in Scheme (I) and the superscript PG represents a protecting group as discussed above. Referring to Scheme (VII), like uridine 60, cytidine 70 has a C4 reactive center such that reaction with amine 10 or protected amine 21 yields N4-substituted cytidine 62 or 64, respectively. These cytidines 62 and 64 are then treated as previously described for Scheme (VI) to yield a 2,4-pyrimidinediamine according to structural formulae (I).

Although Schemes (VI) and (VII) are exemplified with ribosylnucleosides, skilled artisans will appreciate that the corresponding 2'-deoxyribo and 2',3'-dideoxyribo nucleosides, as well as nucleosides including sugars or sugar analogs other than ribose, would also work.

Numerous uridines and cytidines useful as starting materials in Schemes (VI) and (VII) are known in the art, and include, by way of example and not limitation, 5-trifluoromethyl-2'-deoxycytidine (Chem. Sources #ABCR F07669; CAS Registry 66,384-66-5); 5-bromouridine (Chem. Sources Int'l 2000; CAS Registry 957-75-5); 5-iodo-2'-deoxyuridine (Aldrich #1-775-6; CAS Registry 54-42-2); 5-fluorouridine (Aldrich #32,937-1; CAS Registry 316-46-1); 5-iodouridine (Aldrich #85,259-7; CAS Registry 1024-99-3); 5-(trifluoromethyl)uridine (Chem. Sources Int'l 2000; CAS Registry 70-00-8); 5-trifluoromethyl-2'-deoxyuridine (Chem. Sources Int'l 2000; CAS Registry 70-00-8). Additional uridines and cytidines that can be used as starting materials in Schemes (VI) and (VII) are available from General Intermediates of Canada, Inc., Edmonton, Calif. (www.generalintermediates.com) and/or Interchim, Cedex, France (www.interchim.com), or may be prepared using standard techniques. Myriad textbook references teaching suitable synthetic methods are provided infra.

As will be recognized by skilled artisans, certain 2,4-pyrimidinediamines compounds synthesized via the exemplary methods described above, or by other well-known means, may also be utilized as starting materials and/or intermediates to synthesize additional 2,4-pyrimidinediamine compounds. A specific example is illustrated in Scheme (VIII), below:

In Scheme (VIII), $R^4$, $R^5$, $R^6$, $L^2$, Y, $R^a$ and $R^c$ are as previously defined for structural formulae (I). Each $R^{a'}$ is independently an $R^a$, and may be the same or different from the illustrated $R^a$. Referring to Scheme (VIII), carboxylic acid or ester 100 may be converted to amide 104 by reaction with amine 102. In amine 102, $R^{a'}$ may be the same or different than $R^a$ of acid or ester 100. Similarly, carbonate ester 106 may be converted to carbamate 108.

A second specific example is illustrated in Scheme (IX), below:

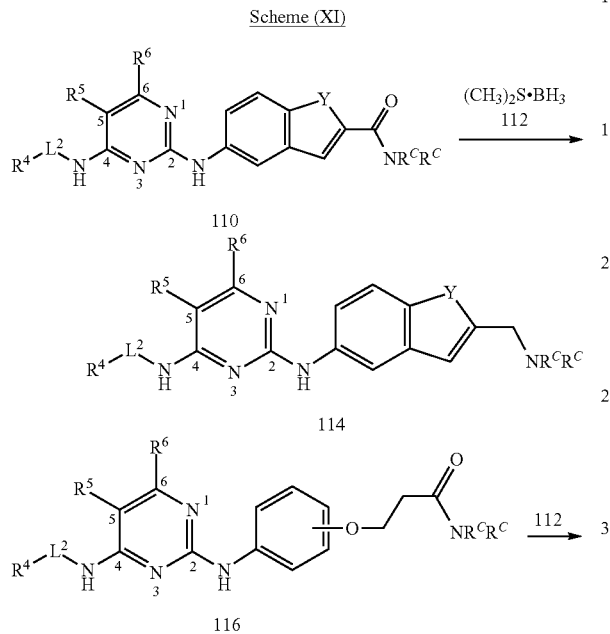

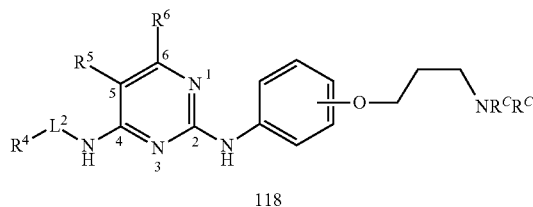

In Scheme (IX) $R^4$, $R^5$, $R^6$, $L^2$, Y and $R^c$ are as previously defined for structural formulae (I). Referring to Scheme (IX), amide 110 or 116 may be converted to amine 114 or 118, respectively, by borane reduction with borane methylsulfide complex 112. Other suitable reactions for synthesizing 2,4-pyrimidinediamine compounds from 2,4-pyrimidinediamine starting materials will be apparent to those of skill in the art.

Compounds including alkyl groups at the amine groups at the 2- and/or 4-position of the 2,4-pyrimidinediamine ring can be prepared using routine alkylation procedures. An exemplary scheme for selectively methylating the amine group at the 4-position of the 2,4-pyrimidinediamine is illustrated in Scheme (XII):

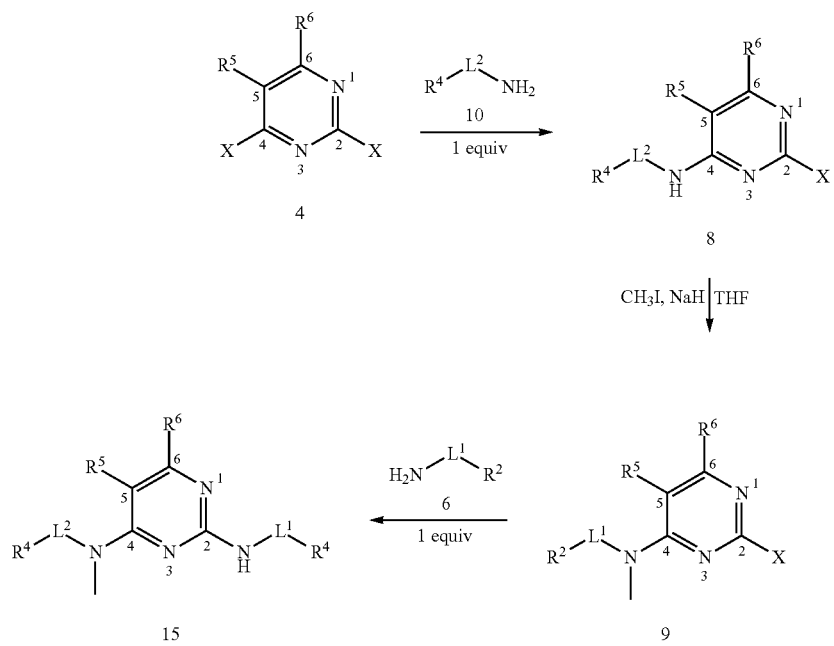

In Scheme (XII), $L^1$, $L^2$, $R^2$, $R^4$, $R^5$ and $R^6$ are as previously defined for structural formula (I). The above Scheme can be routinely adapted to synthesize other N-alkylated compounds.

Compounds that are entiomerically or diasteriomerically pure can be synthesized via chiral-specific syntheses utilizing enantiomerically or diasteriomerically pure starting reagents as is known in the art. Alternatively, specified enantiomers, diastereomers and/or mixtures thereof can be isolated utilizing conventional chiral separation techniques.

Although many of the synthetic schemes discussed above do not illustrate the use of protecting groups, skilled artisans will recognize that in some instances certain substituents, such as, for example, $R^2$ and/or $R^4$, may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups and chemistries for their attachment and removal suitable for a particular application can be found, for example, in Greene & Wuts, supra.

Prodrugs as described herein may be prepared by routine modification of the above-described methods. Alternatively, such prodrugs may be prepared by reacting a suitably protected 2,4-pyrimidinediamine of structural formula (I), (II), (III), (IV) and/or (V) with a suitable progroup. Conditions for carrying out such reactions and for deprotecting the product to yield a prodrugs as described herein are well-known.

Myriad references teaching methods useful for synthesizing pyrimidines generally, as well as starting materials described in Schemes (I)-(IX), are known in the art. For specific guidance, the reader is referred to Brown, D. J., "The Pyrimidines", in *The Chemistry of Heterocyclic Compounds, Volume* 16 (Weissberger, A., Ed.), 1962, Interscience Publishers, (A Division of John Wiley & Sons), New York ("Brown I"); Brown, D. J., "The Pyrimidines", in *The Chemistry of Heterocyclic Compounds, Volume 16, Supplement I* (Weissberger, A. and Taylor, E. C., Ed.), 1970, Wiley-Interscience, (A Division of John Wiley & Sons), New York (Brown II"); Brown, D. J., "The Pyrimidines", in *The Chemistry of Heterocyclic Compounds, Volume 16, Supplement II* (Weissberger, A. and Taylor, E. C., Ed.), 1985, An Interscience Publication (John Wiley & Sons), New York ("Brown III"); Brown, D. J., "The Pyrimidines" in *The Chemistry of Heterocyclic Compounds*, Volume 52 (Weissberger, A. and Taylor, E. C., Ed.), 1994, John Wiley & Sons, Inc., New York, pp. 1-1509 (Brown IV"); Kenner, G. W. and Todd, A., in *Heterocyclic Compounds*, Volume 6, (Elderfield, R. C., Ed.), 1957, John Wiley, New York, Chapter 7 (pyrimidines); Paquette, L. A., *Principles of Modern Heterocyclic Chemistry*, 1968, W. A. Benjamin, Inc., New York, pp. 1-401 (uracil synthesis pp. 313, 315; pyrimidine synthesis pp. 313-316; amino pyrimidine synthesis pp. 315); Joule, J. A., Mills, K. and Smith, G. F., *Heterocyclic Chemistry*, $3^{rd}$ Edition, 1995, Chapman and Hall, London, UK, pp. 1-516; Vorbrüggen, H. and Ruh-Pohlenz, C., *Handbook of Nucleoside Synthesis*, John Wiley & Sons, New York, 2001, pp. 1-631 (protection of pyrimidines by acylation pp. 90-91; silylation of pyrimidines pp. 91-93); Joule, J. A., Mills, K. and Smith, G. F., *Heterocyclic Chemistry*, $4^{th}$ Edition, 2000, Blackwell Science, Ltd, Oxford, UK, pp. 1-589; and *Comprehensive Organic Synthesis*, Volumes 1-9 (Trost, B. M. and Fleming, I., Ed.), 1991, Pergamon Press, Oxford, UK.

5.4 Activity of the Antiproliferative Compounds

Active 2,4-pyrimidinediamine compounds typically inhibit proliferation of desired cells, such as tumor cells, with an $IC_{50}$ in the range of about 1 mM or less, as measured in a standard in vitro cellular proliferation assay. Of course, skilled artisans will appreciate that compounds which exhibit lower $IC_{50}$s, for example on the order of 100 µM, 20 µM, 10 µM, 1 µM, 100 nM, 10 nM, 1 nM, or even lower, may be particularly useful in therapeutic applications. The antiprolierative activity may be cytostatic or it may be cytotoxic. In instances where antiproliferative activity specific to a particular cell type is desired, the compound may be assayed for activity with the desired cell type and counter-screened for a lack of activity against other cell types. The desired degree of "inactivity" in such counter screens, or the desired ratio of activity vs. inactivity may vary for different situations, and may be selected by the user.

5.5 Uses of the Antiproliferative Compounds

The antiproliferative 2,4-pyrimidinediamine compounds, including the various salts, prodrugs, hydrates and N-oxide forms thereof, may be used to inhibit cell proliferation in a variety of contexts. According to some embodiments of the method, a cell or population of cells is contacted with an amount of such a compound effective to inhibit proliferation of the cell or cell population. The compound may act cytotoxically to kill the cell, or cytostatically to inhibit proliferation without killing the cell.

In some embodiments, the methods may be practiced as a therapeutic approach towards the treatment of proliferative disorders. Thus, in a specific embodiment, the 2,4-pyrimidinediamine compounds (and the various forms described herein) may be used to treat proliferative disorders in animal subjects, including humans. The method generally comprises administering to the subject an amount of a compound of the invention, or a salt, prodrug, hydrate or N-oxide thereof, effective to treat the disorder. In one embodiment, the subject is a mammal, including, but not limited to, bovine, horse, feline, canine, rodent, or primate. In another embodiment, the subject is a human.

A variety of cellular proliferative disorders may be treated with the compounds of the present invention. In one embodiment, the compounds are used to treat various cancers in afflicted subjects. Cancers are traditionally classified based on the tissue and cell type from which the cancer cells originate. Carcinomas are considered cancers arising from epithelial cells while sarcomas are considered cancers arising from connective tissues or muscle. Other cancer types include leukemias, which arise from hematopoietic cells, and cancers of nervous system cells, which arise from neural tissue. For non-invasive tumors, adenomas are considered benign epithelial tumors with glandular organization while chondomas are benign tumor arising from cartilage. In the present invention, the described compounds may be used to treat proliferative disorders encompassed by carcinomas, sarcomas, leukemias, neural cell tumors, and non-invasive tumors.

In a specific embodiment, the compounds are used to treat solid tumors arising from various tissue types, including, but not limited to, cancers of the bone, breast, respiratory tract (e.g., bladder), brain reproductive organs, digestive tract, urinary tract, eye, liver, skin, head, neck, thyroid, parathyroid, and mestastatic forms thereof.

Specific proliferative disorders include the following: a) proliferative disorders of the breast include, but are not limited to, invasive ductal carcinoma, invasive lobular carcinoma, ductal carcinoma, lobular carcinoma in situ, and metastatic breast cancer; b) proliferative disorders of the skin include, but are not limited to, basal cell carcinoma, squamous cell carcinoma, malignant melanoma, and Karposi's sarcoma; c) proliferative disorders of the respiratory tract include, but are not limited to, small cell and non-small cell lung carcinoma, bronchial adema, pleuropulmonary blastoma, and malignant mesothelioma; d) proliferative disorders of the brain include, but are not limited to, brain stem and hyptothalamic glioma, cerebellar and cerebral astrocytoma, medullablastoma, ependymal tumors, oligodendroglial, meningiomas, and neuroectodermal and pineal tumors; e) proliferative disorders of the male reproductive organs include, but are not limited to, prostate cancer, testicular cancer, and penile cancer f) proliferative disorders of the female reproductive organs include, but are not limited to, uterine cancer (endometrial), cervical, ovarian, vaginal, vulval cancers, uterine sarcoma, ovarian germ cell tumor; g) proliferative disorders of the digestive tract include, but are not limited to, anal, colon, colorectal, esophageal, gallbladder, stomach (gastric), pancreatic cancer, pancreatic cancer-Islet cell, rectal, small-intestine, and salivary gland cancers; h) proliferative disorders of the liver include, but are not limited to, hepatocellular carcinoma, cholangiocarcinoma, mixed hepatocellular cholangiocarcinoma, and primary liver cancer; i) proliferative disorders of the eye include, but are not limited to, intraocular melanoma, retinoblastoma, and rhabdomyosarcoma; j) proliferative disorders of the head and cancers include, but are not limited to, laryngeal, hypopharyngeal, nasopharyngeal, oropharyngeal cancers, and lip and oral cancer, squamous neck cancer, metastatic paranasal sinus cancer; k) proliferative disorders of the lymphomas include, but are not limited to, various T cell and B cell lymphomas, non-Hodgkins lymphoma, cutaneous T cell lymphoma, Hodgkins disease, and lymphoma of the central nervous system; l) leukemias include, but are not limited to, acute myeloid leukemia, acute lymphoblastic leukemia, chronic lymphocytic leukemia, chronic myelogenous leukemia, and hair cell leukemia, m) proliferative disorders of the thyroid include thyroid cancer, thymoma, and malignant thymoma; n) proliferative disorders of the urinary tract include, but are not limited to, bladder cancer; o) sarcomas include, but are not limited to, sarcoma of the soft tissue, osteosarcoma, malignant fibrous histiocytoma, lymphosarcoma, and rhabdomyosarcoma.

It is to be understood that the descriptions of proliferative disorders is not limited to the conditions described above, but encompasses other disorders characterized by uncontrolled growth and malignancy. It is further understood that proliferative disorders include various metastatic forms of the tumor and cancer types described herein. The compounds of the present invention may be tested for effectiveness against the disorders described herein, and a therapeutically effective regimen established. Effectiveness, as further described below, includes reduction or remission of the tumor, decreases in the rate of cell proliferation, or cytostatic or cytotoxic effect on cell growth.

5.6 Combination Therapies

The compounds of the present invention may be used alone, in combination with one another, or as an adjunct to, or in conjunction with, other established antiproliferative therapies. Thus, the compounds of the present invention may be used with traditional cancer therapies, such as ionization radiation in the form of γ-rays and x-rays, delivered externally or internally by implantation of radioactive compounds, and as a follow-up to surgical removal of tumors.

In another aspect, the compounds of the present invention may be used with other chemotherapeutic agents useful for the disorder or condition being treated. These compounds may be administered simultaneously, sequentially, by the same route of administration, or by a different route.

In one embodiment, the present compounds may be used with other anti-cancer or cytotoxic agents. Various classes of anti-cancer and anti-neoplastic compounds include, but are not limited to, alkylating agents, antimetabolites, vinca alkyloids, taxanes, antibiotics, enzymes, cytokines, platinum coordination complexes, substituted ureas, tyrosine kinase inhibitors, hormones and hormone antagonists. Exemplary alkylating agents include, by way of example and not limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mecaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as anti-neoplastic agents include L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesteron caproate, medroxyprogesterone; and anti-estrogen compound tamoxifen.

These and other useful anti-cancer compounds are described in *Merck Index,* 13th Ed. (O'Neil M. J. et al., ed) Merck Publishing Group (2001) and *Goodman and Gilmans The Pharmacological Basis of Therapeutics,* 10th Edition, Hardman, J. G. and Limbird, L. E. eds., pg. 1381-1287, McGraw Hill, (1996), both of which are incorporated by reference herein.

Additional anti-proliferative compounds useful in combination with the compounds of the present invention include, by way of example and not limitation, antibodies directed against growth factor receptors (e.g., anti-Her2); antibodies for activating T cells (e.g., anti-CTLA-4 antibodies); and cytokines such as interferon-α and interferon-γ, interleukin-2, and GM-CSF.

5.7 Formulations and Administration

When used to treat or prevent such diseases, the active compounds may be administered singly, as mixtures of one or more active compounds or in mixture or combination with other agents useful for treating such diseases and/or the symptoms associated with such diseases. The active compounds may also be administered in mixture or in combination with agents useful to treat other disorders or maladies, such as steroids, membrane stabilizers. The active compounds or prodrugs may be administered per se, or as pharmaceutical compositions, comprising an active compound or prodrug.

Pharmaceutical compositions comprising the active compounds of the invention (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see *Remingtons's Pharmaceutical Sciences*, 15$^{th}$ Ed., Hoover, J. E. ed., Mack Publishing Co. (2003)

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

5.8 Effective Dosages

The active compound(s) or prodrug(s) of the invention, or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," In: *Goodman and Gilman's The Pharmaceutical Basis of Therapeutics*, Chapter 1, pp. 1-46, latest edition, Pagamonon Press, and the references cited therein.

Initial dosages may also be estimated from in vivo data, such as animal models. Animal models useful for testing the efficacy of compounds to treat or prevent the various diseases described above are well-known in the art. Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) $LD_{50}/ED_{50}$ effect is the therapeutic index ($LD_{50}$ is the dose lethal to 50% of the population and $ED_{50}$ is the dose therapeutically effective in 50% of the population). Compounds(s) that exhibit high therapeutic indices are preferred.

5.9 Kits

The compounds and/or prodrugs described herein may be assembled in the form of kits. In some embodiments, the kit provides the compound(s) and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In some embodiments, the therapeutic agents are other anti-cancer and anti-neoplastic compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

6. EXAMPLES

6.1 In Vitro Cellular Experiments

The compounds illustrated in TABLES 1-14, supra, were synthesized using the methods described herein. Salts of the compounds were prepared using standard techniques.

The $IC_{50}$ values of various compounds against a various different tumor cell lines were determined using standard in vitro antiproliferation assays. The tumor cell lines tested were as follows: A549 (lung); H1299 (lung), ACHN (kidney/p53 wt), CAKI (renal cell carcinoma), NCI-H460 (lung); HCT116 (colon/p53wt); HELA (cervix/p53 wt), HUH7 (liver/p53 wt), HUVEC (primary endothelial), LNCAP (prostate), HT-29 (colon); MCF-7 (breast); MCF-7 (breast/ER positive), MDA MB435S (breast); MDA MB231 (breast/ER negative), DU145 (prostate); BxPC-3 (pancreatic); SKOV-3 (ovarian); HepG2 (hepatic), NDHF primary normal human dermal fibroblast), SKMEL28 (breast/p53mut), SKMEL5 (breast/p53 wt), U2OS (bone) and PC3 (prostate). The activity of the compounds against A549 cells and H1299 cells is reported in TABLES 1-14, supra. In the tables, a "+" indicates an $IC_{50}$ of ≤20 μM or less, a "−" indicates an $IC_{50}$ of >20 μM. A value of "−/+" indicates that the specific compound exhibited an $IC_{50}$ of >20 μM in a 3-point assay, but exhibited an $IC_{50}$ of ≤20 μM in a higher-point (e.g., 6-point) assay. A value of "+/−" indicates that the specific compound exhibited an $IC_{50}$ of ≤20 μM in a 3-point assay, but exhibited an $IC_{50}$ of >20 μM in a higher-point (e.g., 6-point) assay. A blank indicates the specified compound was not tested against the specified cell line. Many of the compounds tested exhibited IC50s against A549 and/or H1299 cells in the nanomolar range.

Many of the compounds were tested against other cell lines. Their activity is reported in TABLE 15, below, where "+", "−", "−/+" or "+/−" values are as described for TABLES 1-14. Where the cell line includes a value in a parenthetical, the value indicates the seeding density at which the assay was performed

TABLE 15

| No | ACHN | CAKI | HCT116 | HELA | HUH7 | HUVEC | LNCAP | MCF7(2K) | MCF7(4K) | MDA-MB-231(2K) | MDA-MB-231(4K) | NDHF | PC3 | SKMEL28 | SKMEL5 | U2OS |
|---|---|---|---|---|---|---|---|---|---|---|---|---|---|---|---|---|
| 254 | | | | | | | | | | | | | + | | | |
| 256 | | | | | | | | | | | | | + | | | |
| 300 | | | + | | | | | | | | | | | | | |
| 697 | | | | | | | | | | | | | − | | | |
| 699 | | | | | | | | | | | | | | | | |
| 710 | | | + | | | | | | | | | | | | | |
| 717 | | | − | | | + | | | | | | | | | | |
| 493 | | | −/+ | | | | | | | | | | | | | |
| 494 | | | + | | | | | | | | | | | | | |
| 534 | | | + | | | | | | | | | | | | | |
| 626 | | | + | | | | | | | | | | | | | |
| 495 | | | + | | | | | | | | | | | | | |
| 629 | | | + | | | | | | | | | | | | | |
| 632 | | | + | | | | | | | | | | | | | |
| 633 | | | + | | | | | | | | | | | | | |
| 634 | | | + | | | | | | | | | | | | | |
| 496 | | | − | | | | | | | | | | | | | |
| 497 | | | − | | | | | | | | | | | | | |
| 732 | | | + | | | | | | | | | | | | | |
| 500 | | | + | | | | | | | | | | | | | |
| 636 | | | − | | | | | | | | | | | | | |
| 742 | | | | | | | | | | | | | − | | | |
| 501 | | | | | | | | | | | | | + | | | |
| 502 | | | | | | | | | | | | | − | | | |
| 746 | | | | | | | | | | | | | − | | | |
| 747 | | | | | | | | | | | | | + | | | |
| 642 | | | | | | | | | | | | | + | | | |
| 748 | | | | | | | | | | | | | − | | | |
| 643 | | | | | | | | | | | | | − | | | |
| 749 | | | | | | | | | | | | | + | | | |
| 750 | | | | | | | | | | | | | − | | | |
| 751 | | | | | | | | | | | | | + | | | |
| 752 | | | + | | | | | | | | | | − | | | |
| 503 | | | | | | | | | | | | | − | | | |
| 753 | | | + | | | | | | | | | | − | | | |
| 754 | | | + | | | | | | | | | | | | | |
| 755 | | | − | | | | | | | | | | | | | |
| 504 | | | − | | | | | | | | | | | | | |
| 506 | | | | | | | | | | | | | − | | | |
| 507 | | | | | | | | | | | | | − | | | |
| 508 | | | | | | | | | | | | | − | | | |
| 509 | | | | | | | | | | | | | − | | | |
| 644 | | | + | | | | | | | | | | − | | | |
| 645 | | | + | | | | | | | | | | | | | |
| 510 | | | | | | | | | | | | | − | | | |
| 761 | | | | | | | | | | | | | − | | | |
| 762 | | | | | | | | | | | | | + | | | |
| 763 | | | | | | | | | | | | | − | | | |
| 764 | | | | | | | | | | | | | − | | | |

TABLE 15-continued

| No | ACHN | CAKI | HCT116 | HELA | HUH7 | HUVEC | LNCAP | MCF7(2K) | MCF7(4K) | MDA-MB-231(2K) | MDA-MB-231(4K) | NDHF | PC3 | SKMEL28 | SKMEL5 | U20S |
|---|---|---|---|---|---|---|---|---|---|---|---|---|---|---|---|---|
| 765 | | | | | | | | | | | | | + | | | |
| 511 | + | | − | | | | | | | | | + | − | + | + | + |
| 512 | + | | − | + | + | + | | | | | | + | − | + | + | + |
| 766 | | | + | + | + | + | | | | | | | − | + | + | + |
| 767 | | | − | | | | | | | | | | | | | |
| 646 | + | | + | + | + | + | + | | | | | + | | | | |
| 647 | | | + | | | | | | | | | | | | | |
| 649 | + | | − | + | + | + | + | | | | | | + | + | + | + |
| 516 | | | + | | | | | | | | | | | | | |
| 523 | | | − | | | + | + | | | | | + | | | | |
| 790 | | | | | | | | | | | | | | | | |
| 651 | | | + | | | | | | | | | | | | | |
| 652 | | | − | | | | | | | | | | | | | |
| 305 | | | + | | | | | | | | | | | | | |
| 306 | | | − | | | | | | | | | | | | | |
| 307 | | | + | | | | | | | | | | | | | |
| 835 | | | + | | | + | | | | | | | | | | |
| 309 | | | + | | | | | | | | | | | | | |
| 310 | | | + | | | | | | | | | | | | | |
| 311 | | | + | | | | | | | | | | | | | |
| 312 | | | −/+ | | | | | | | | | | | | | |
| 313 | | | −/+ | | | | | | | | | | | | | |
| 314 | | | + | | | | | | | | | | | | | |
| 838 | | | + | | | | | | | | | | | | | |
| 527 | | | + | | | | | | | | | | | | | |
| 528 | | | + | | | − | | | | | | | | | | |
| 839 | | | + | | | | | | | | | | | | | |
| 841 | | | + | | | | | | | | | | | | | |
| 529 | | | + | | | + | | | | | | | | | | |
| 845 | | | + | | | | | | | | | | | | | |
| 846 | + | + | + | | | | | | | | | | | + | + | |
| 847 | + | + | + | | | | | | | | | | | + | + | |
| 848 | | + | + | | | | | | | | | | | + | + | |
| 654 | | | + | | | | | | | | | | | | | |
| 851 | | | + | + | | | | | | | | | | + | + | |
| 858 | + | | + | + | | | | + | | | | | | + | + | + |
| 868 | + | | + | | | | | | + | + | | | | + | + | + |
| 869 | | | + | | | | | | | | + | | | + | | |
| 933 | | | + | | | | | | | | | | | | | |
| 938 | | | | | | | | | | | | | | | | |
| 940 | | | + | | | | | | | | | | − | | | |
| 580 | | | | | | | | | | | | | + | | | |
| 581 | | | | | | | | | | | | | − | | | |
| 942 | + | | + | | | | | | | | | + | + | + | + | + |
| 947 | | | + | | | | | | | | | | | | | |
| 948 | | | + | | | | | | | | | | + | | | |
| 949 | | | | | | | | | | | | | + | | | |
| 950 | | | | | | | | | | | | | − | | | |
| 954 | | | + | | | | | | | | | | | | | |
| 955 | | | | | | | | | | | | | − | | | |

TABLE 15-continued

| No | ACHN | CAKI | HCT116 | HELA | HUH7 | HUVEC | LNCAP | MCF7(2K) | MCF7(4K) | MDA-MB-231(2K) | MDA-MB-231(4K) | NDHF | PC3 | SKMEL28 | SKMEL5 | U2OS |
|---|---|---|---|---|---|---|---|---|---|---|---|---|---|---|---|---|
| 956 | | | | | | | | | | | | | − | | | |
| 957 | | | | | | | | | | | | | + | | | |
| 958 | | | | | | | | | | | | | − | | | |
| 959 | | | | | | | | | | | | | − | | | |
| 960 | | | | | | | | | | | | | − | | | |
| 961 | | | | | | | | | | | | | − | | | |
| 962 | | | | | | | | | | | | | + | | | |
| 355 | | | − | | + | | | | | | | | | | | |
| 356 | | | − | | | | | | | | | | | | | |
| 676 | | | | | | | | | | | | | + | | | |
| 677 | | | | | | | | | | | | | | | | |
| 358 | | | −/+ | | | | | | | | | | | | | |
| 359 | | | +/− | | + | | | | | | | | | | | |
| 978 | | | | | | | | | | | | | − | | | |
| 979 | | | | | | | | | | | | | − | | | |
| 980 | | | | | | | | | | | | | + | | | |
| 981 | | | + | | | | | | | | | | − | | | |
| 982 | | | | | | | | | | | | | + | | | |
| 983 | | | | | | | | | | | | | − | | | |
| 984 | | | + | | | | | | | | | | − | | | |
| 985 | | | | | | | | | | | | | + | | | |
| 986 | | | | | | | | | | | | | − | | | |
| 987 | | | | | | | | | | | | | + | | | |
| 418 | | | | | | | | | | | | | + | | | |
| 101 | + | + | + | | | | | | | | | | | | | |
| 102 | + | + | + | | | | | | | | | | | | | |
| 103 | + | + | + | | | | | | | | | | | | | |
| 991 | | | − | | | | | | | | | | | | | |
| 104 | | | + | | | | | | | | | | | | | |
| 105 | + | + | + | | | | | | | | | | | | | |
| 106 | + | + | + | | | | | | | | | | | + | + | |
| 107 | | | + | + | | + | + | + | + | + | + | + | | + | + | + |
| 419 | | | − | | | | | | | | | | | + | + | |
| 420 | | | + | | | | | | | | | | | | | |
| 110 | | | + | | | | | | | | | | | | | |
| 111 | | | + | | | | | | | | | | | | | |
| 112 | | | + | | | | | | | | | | | | | |
| 113 | | | + | | | | | | | | | | | | | |
| 114 | | | + | | | | | | | | | | | | | |
| 432 | | | + | | | | | | | | | | | | | |
| 435 | | | + | | | | | | | | | | | | | |
| 436 | | | + | | | | | | | | | | | | | |
| 211 | | | | + | | | + | + | + | + | | | | | | |
| 125 | | | | + | | | + | + | + | + | | | | | | |
| 141 | | | | + | | | + | + | + | + | | | | | | |
| 1006 | | | | | | + | | | | | | | | | | |
| 1007 | | | | | | − | | | | | | | | | | |
| 1009 | | | | | | + | | | | | | | | | | |

6.2 In Vivo Xenograft Experiments

Compounds 107, 858, 164, 211 and 156 were tested for their ability to shrink tumors generated from A549 cells in standard xenograft experiments. Compounds 141 and 211 were tested against H1299 tumors. When palpable tumors appeared and were of a preselected volume (approximately 40-150 mm$^3$), the mice were administered test compounds as specified in TABLE 16, below. Preliminary results are reported in TABLE 16.

TABLE 16

| Test Compound | Cell Type | Dose | Dose Schedule | Formulation | Comments | Preliminary Results |
|---|---|---|---|---|---|---|
| 107 | A549 | 40 mg/kg | 3x a day for 4 days followed by 5 days rest. | Liposome Vehicle (DMPC) | No precipitation was noted | No significant reduction in tumor size |
| 107 | A549 | 25 mg/kg and 50 mg/kg | Bid, daily And Bid 4 days w/8 days rest | 16% Cremophor/ 16% EtOH/ 68% Saline | Compound crashed out of solution when saline was added | No significant reduction in tumor size seen with either dose |
| 858 | A549 | 25 mg/kg | Bid, daily | 5% EtOH/ 15% Cremophor/ 80% Saline | No precipitation was noted | No significant reduction in tumor size seen |
| 164, 211 | A549 | 25 mg/kg | R563-5 days bid with 2 days of rest R565-bid, daily | 100% DMSO | No precipitation was noted | 23.2% reduction in tumor size in mice treated with 211. Compound 164 showed no significant reduction in tumor size. |
| 141, 211 | H1299 | 25 mg/kg | Bid, daily | 100% DMSO | Compound 141 precipitated out on day 2. Compound was prepared fresh for days 3, 4, and 5. No precipitation was noted for Compound 211 | No significant reduction in tumor size was seen with either compound. |
| 156 | A549 | 25 mg/kg and 50 mg/kg | Bid, daily | 0.9% Saline | No precipitation was noted | 60.4% reduction in tumor size was observed in mice treated with 50 mg/kg. No significant reduction was seen at the lower dose. |

Although the foregoing inventions have been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

It is to be understood that when ranges of integers are described herein, the description is intended to include the endpoints and each intervening integer as though each integer were explicitly delineated. As a specific example, the description "an integer from 1 to 6," is intended to explicitly describe 1, 2, 3, 4, 5 and 6.

All literature and patent references cited throughout the application are incorporated by reference into the application for all purposes.

What is claimed is:

1. A method of inhibiting proliferation of a cancer cell, comprising contacting the cancer cell with an effective amount of a 2,4-pyrimidinediamine compound according to structural formula (I):

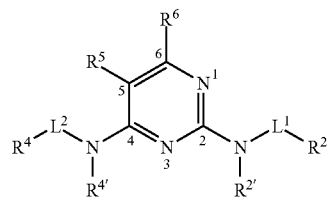

or a prodrug, salt, hydrate, solvate or N-oxides thereof, wherein:

L$^1$ and L$^2$ are each, independently of one another, selected from a lower alkyldiyl linker, a lower alkylene linker and a covalent bond;

R² is selected from the group consisting of lower alkyl optionally substituted with an R^b group,

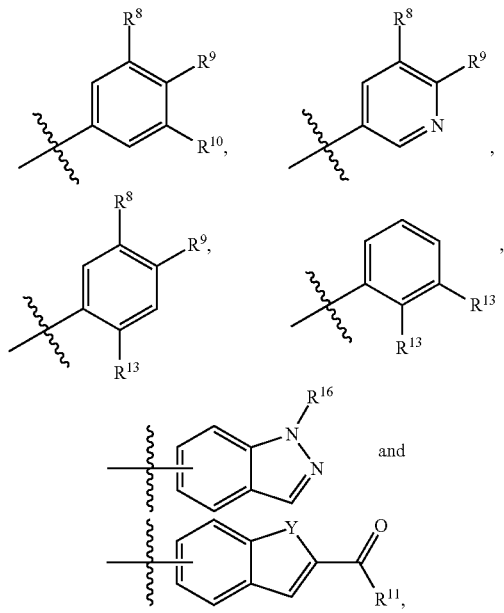

where Y is NH, O or CH₂;
R²' is hydrogen, methyl or lower alkyl;
R⁴' is hydrogen, methyl or lower alkyl;
R⁴ is

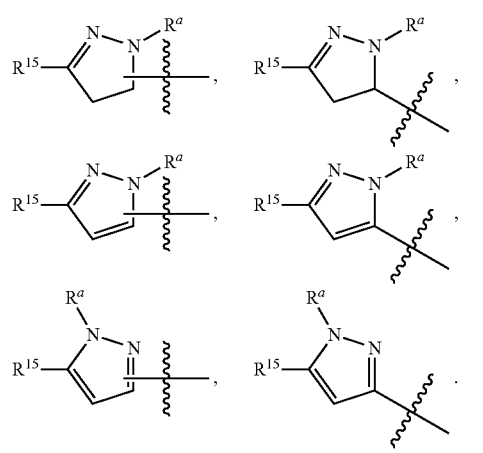

R⁵ is selected from the group consisting of halo, fluoro and —CF₃;
R⁶ is hydrogen;
each R⁸ is independently selected from the group consisting of hydrogen, lower alkyl, —(CH₂)$_n$—OH, —OR$^a$, —(CH₂)$_n$—NR$^c$R$^c$, —O(CH₂)$_n$—R$^a$, —O(CH₂)$_n$—R$^b$, —C(O)OR$^a$, —C(S)O R$^a$, halo, —CF₃ and —OCF₃;
each R⁹ is independently selected from the group consisting of hydrogen, lower alkyl, —OR$^a$, —(CH₂)$_n$—NR$^c$R$^c$, —O(CH₂)$_n$—R$^a$, —O(CH₂)$_n$—R$^b$, —C(O)—NR$^c$R$^c$, —C(S)—NR$^c$R$^c$, —S(O)₂—NR$^c$R$^c$, —NHC(O)R$^a$, —NHC(S)R$^a$, —C(O)—NH—(CH₂)$_n$—NR$^c$R$^c$, —C(S)—NH—(CH₂)$_n$—NR$^c$R$^c$, halo, —CF₃, —OCF₃,

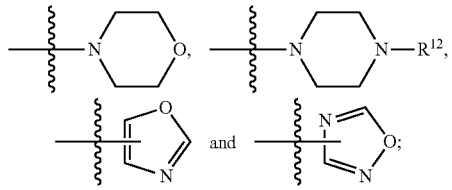

each R¹⁰ is independently selected from the group consisting of hydrogen, lower alkyl, —(CH₂)$_n$—OH, —(CH₂)$_n$—NR$^c$R$^c$, —OR$^a$, —O(CH₂)$_n$—R$^a$, —O(CH₂)$_n$—R$^b$, halo, —CF₃, —OCF₃, $$\text{(morpholine, piperazine-R}^{12}\text{, oxazole, isoxazole structures)}$$

each R¹¹ is independently selected from the group consisting of —OR$^a$, —NR$^c$R$^c$ and —NR$^a$R$^d$;
each R¹² is independently selected from the group consisting of lower alkyl, arylalkyl, —OR$^a$, —NR$^c$R$^c$, —C(O)R$^a$, —C(O)OR$^a$ and —C(O) NR$^c$R$^c$;
each R¹³ is independently selected from the group consisting of lower alkyl, hydroxy, lower alkoxy, methoxy, —C(O)NR$^c$R$^c$ and —C(O)NH₂;
each R¹⁵ is independently selected from the group consisting of hydrogen, lower alkyl, lower cycloakyl and phenyl;
each R¹⁶ is independently selected from the group consisting of hydrogen, methyl, lower alkyl, lower cycloalkyl, lower branched alkyl and lower cycloalkylmethyl;
each m is independently an integer from 1 to 3;
each n is independently an integer from 1 to 3;
each R$^a$ is independently selected from the group consisting of hydrogen, lower alkyl, lower cycloalkyl, lower cycloalkylalkyl, phenyl and benzyl;
each R$^b$ is independently selected from the group consisting of —OR$^a$, —CF₃, —OCF₃, —NR$^c$R$^c$, —C(O)R$^a$, —C(S)R$^a$, —C(O)OR$^a$, —C(S)OR$^a$, —C(O)NR$^c$R$^c$, —C(S)NR$^c$R$^c$, —S(O)₂NR$^c$R$^c$, —C(O)NR$^a$R$^d$, —C(S)NR$^a$R$^d$ and —S(O)₂NR$^a$R$^d$;
each R$^c$ is independently selected from the group consisting of hydrogen, lower alkyl and lower cycloalkyl, or, alternatively, two R$^c$s may be taken together with the nitrogen atom to which they are bonded to form a 5-7 membered saturated ring which optionally includes 1-2 additional heteroatomic groups selected from O, NR$^a$, NR$^a$—C(O)R$^a$, NR$^a$—C(O)OR$^a$ and NR$^a$—C(O)NR$^a$; and
each R$^d$ is independently selected from lower mono-hydroxyalkyl and lower di-hydroxyalkyl,
with the provisos that:
(i) when R² is

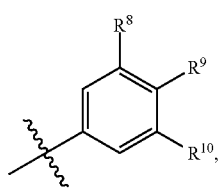

then $R^9$ and $R^{10}$ are not both simultaneously lower alkoxy or methoxy;

(ii) $R^2$ is not 3,4,5-trimethoxyphenyl or 3,4,5-tri(loweralkoxy)phenyl;

(iii) $R^2$ is not lower alkyl;

(iv) when $R^4$ is

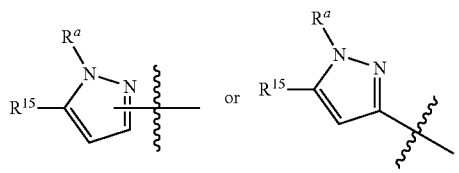

where $R^{15}$ is t-butyl and $R^2$ is

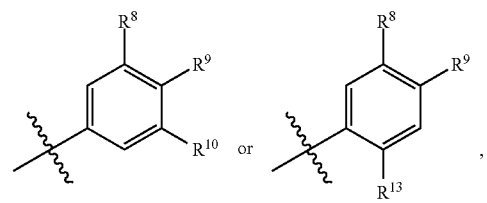

then at least two of $R^8$, $R^9$ and $R^{10}$ or $R^8$, $R^9$ and $R^{13}$ are other than hydrogen;

and (v) when $R^4$ is

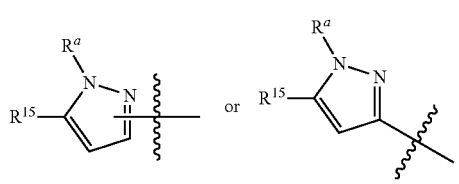

where $R^{15}$ is t-butyl and $R^2$ is

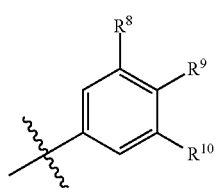

where $R^8$ and $R^9$ are each hydrogen, then $R^{10}$ is other than $-(CH_2)_n-OH$ or $-O(CH_2)_n-R^b$ where $R^b$ is selected from $-NR^cR^c$, $-C(O)R^a$, $-C(O)NR^cR^c$ and $-C(O)NR^aR^d$.

2. The method of claim 1 in which $L^1$ and $L^2$ are each a covalent bond.

3. The method of claim 2 in which $R^5$ is fluoro.

4. The method of claim 3 in which $R^{2'}$ and $R^{4'}$ are each hydrogen.

5. The method of claim 3 in which $R^{2'}$ is hydrogen and $R^{4'}$ is methyl.

6. The method of claim 3 in which $R^2$ is

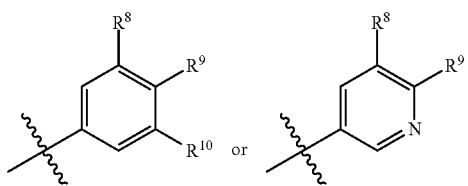

7. The method of claim 3 in which $R^4$ is

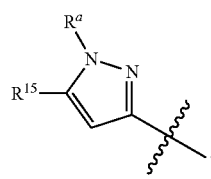

8. The method of claim 7 in which $R^a$ is hydrogen and $R^{15}$ is selected from lower branched alkyl and lower cycloalkyl.

9. The method of claim 7 in which $R^{15}$ is t-butyl or cyclopropyl.

10. The method of claim 7 in which $R^2$ is

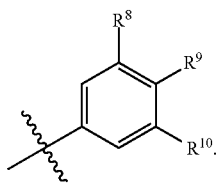

11. The method of claim 10 in which $R^8$ is hydrogen; $R^9$ is selected from

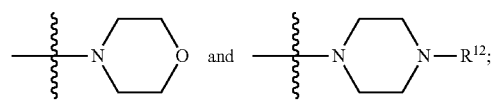

and $R^{10}$ is other than

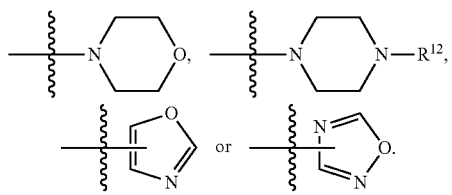

12. The method of claim 10 in which $R^{10}$ is selected from methyl, trifluoromethyl and chloro.

13. The method of claim 10 in which $R^{12}$ of $R^9$ is selected from methyl, $-C(O)CH_3$, $-C(O)OCH_3$ and $-C(O)CH_2CH_3$.

14. The method of claim 13 in which $R^9$ is selected from hydrogen, methyl, trifluoromethyl and chloro.

15. The method of claim 13 in which $R^{12}$ of $R^{10}$ is selected from methyl, $-C(O)CH_3$, $-C(O)OCH_3$ and $-C(O)CH_2CH_3$.

16. The method of claim 10 in which $R^8$ is hydrogen; $R^9$ is other than
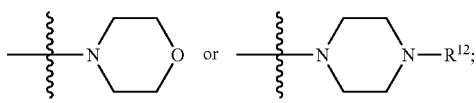
and $R^{10}$ is selected from
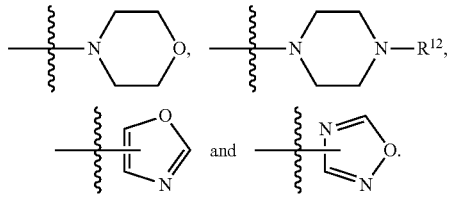
17. The method of claim 1 wherein the compound is
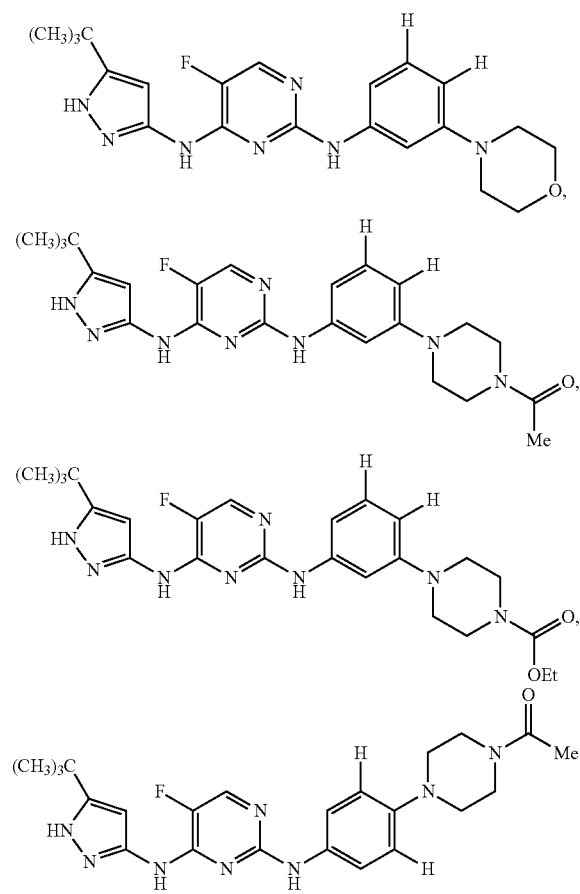
-continued
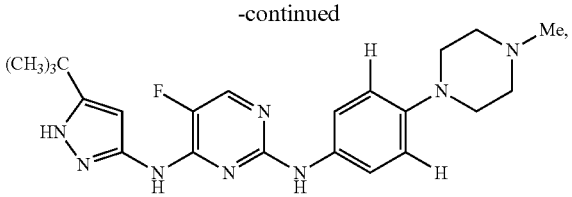
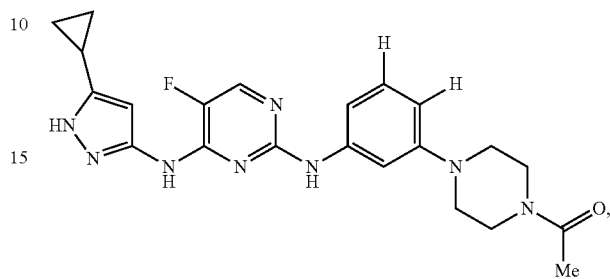
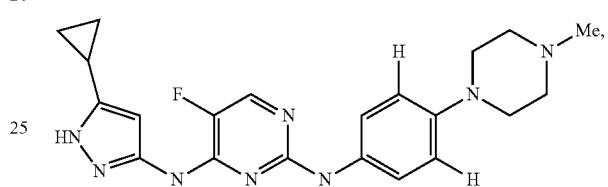
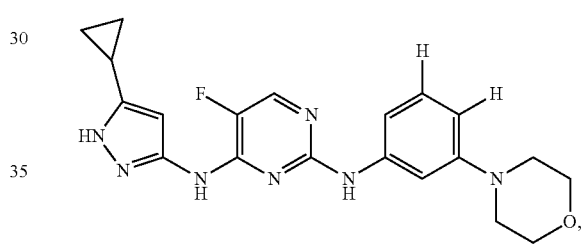
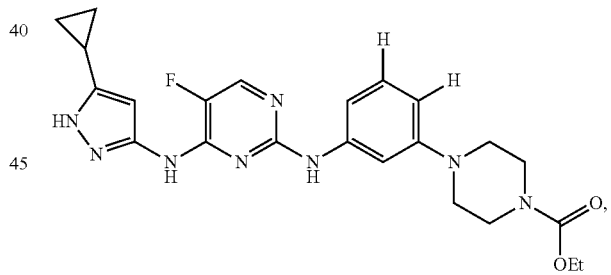
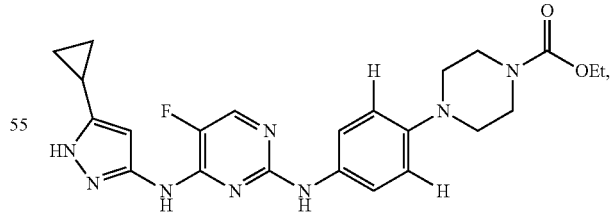
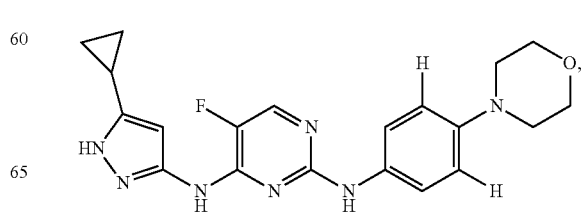

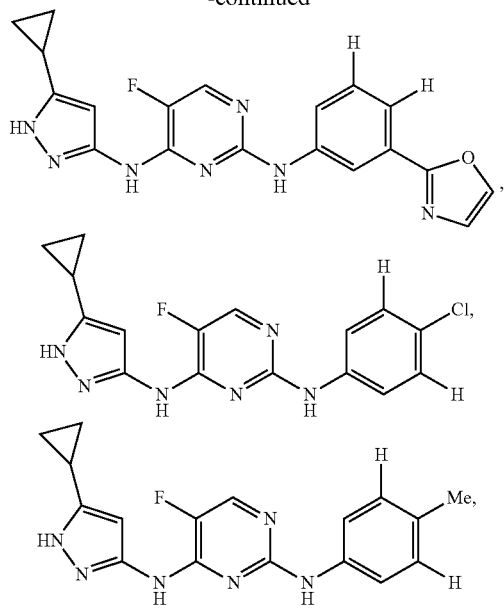
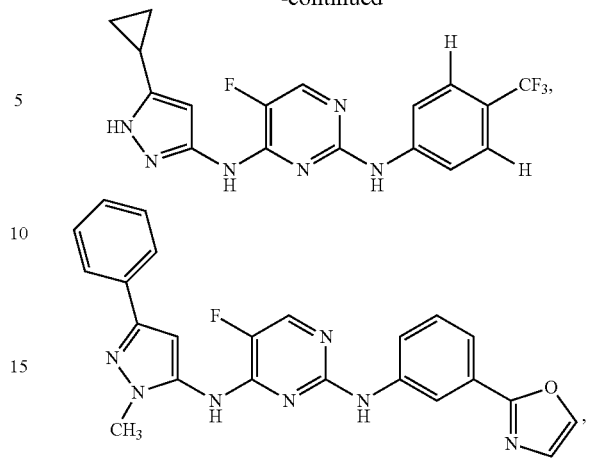
or a pharmaceutically acceptable salt of any of the foregoing.
* * * * *